(12) United States Patent
Torii et al.

(10) Patent No.: US 8,247,491 B2
(45) Date of Patent: Aug. 21, 2012

(54) WATER-ABSORBENT RESIN COMPOSITION AND ITS PRODUCTION PROCESS

(75) Inventors: Kazushi Torii, Himeji (JP); Yoshiro Mitsukami, Himeji (JP); Motohiro Imura, Akashi (JP); Taku Iwamura, Himeji (JP); Toshimasa Kitayama, Himeji (JP); Kenji Kadonaga, Kakogawa (JP); Hiroki Inoue, Kyoto (JP); Koji Miyake, Okayama (JP); Kozo Nogi, Kakogawa (JP); Masatoshi Nakamura, Himeji (JP); Shigeru Sakamoto, Himeji (JP); Sayaka Machida, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 879 days.

(21) Appl. No.: 10/544,348

(22) PCT Filed: Feb. 6, 2004

(86) PCT No.: PCT/JP2004/001294
§ 371 (c)(1),
(2), (4) Date: Aug. 3, 2005

(87) PCT Pub. No.: WO2004/069293
PCT Pub. Date: Aug. 19, 2004

(65) Prior Publication Data
US 2006/0073969 A1    Apr. 6, 2006

(30) Foreign Application Priority Data

Feb. 10, 2003 (JP) .................. 2003-032698
Mar. 10, 2003 (JP) .................. 2003-063548
Sep. 2, 2003 (JP) .................. 2003-310386
Sep. 12, 2003 (JP) .................. 2003-322031

(51) Int. Cl.
*C08L 33/02* (2006.01)
*C08L 31/00* (2006.01)
*C08L 29/04* (2006.01)
*C08F 20/06* (2006.01)
*C08K 3/22* (2006.01)

(52) U.S. Cl. ........ 524/556; 524/557; 524/503; 524/437; 526/317.1

(58) Field of Classification Search .................. 524/556, 524/557, 502, 503, 437; 526/317.1
See application file for complete search history.

(56) References Cited

U.S. PATENT DOCUMENTS

| | | | |
|---|---|---|---|
| 3,935,099 A | 1/1976 | Weaver et al. | |
| 3,959,569 A | 5/1976 | Burkholder, Jr. | |
| 4,076,663 A | 2/1978 | Masuda et al. | |
| 4,093,776 A | 6/1978 | Aoki et al. | |
| 4,124,748 A | 11/1978 | Fujimoto et al. | |
| 4,367,323 A | 1/1983 | Kitamura et al. | |
| 4,389,513 A | 6/1983 | Miyazaki | |
| 4,446,261 A | 5/1984 | Yamasaki et al. | |
| 4,587,308 A | 5/1986 | Makita et al. | |
| 4,625,001 A | 11/1986 | Tsubakimoto et al. | |
| 4,654,039 A | 3/1987 | Brandt et al. | |
| 4,683,274 A | 7/1987 | Nakamura et al. | |
| 4,690,996 A | 9/1987 | Shih et al. | |
| 4,693,713 A | 9/1987 | Chmelir et al. | |
| 4,721,647 A | 1/1988 | Nakanishi et al. | |
| 4,738,867 A | 4/1988 | Itoh et al. | |
| 4,748,076 A | 5/1988 | Saotome | |
| 4,769,427 A | 9/1988 | Nowakowsky et al. | |
| 4,771,105 A | 9/1988 | Shirai et al. | |
| 4,876,299 A | 10/1989 | Avar | |
| 4,950,692 A | 8/1990 | Lewis et al. | |
| 5,002,986 A | 3/1991 | Fujiura et al. | |
| 5,051,259 A | 9/1991 | Olsen et al. | |
| 5,112,902 A | 5/1992 | Moriya et al. | |
| 5,250,640 A | 10/1993 | Irie et al. | |
| 5,264,495 A | 11/1993 | Irie et al. | |
| 5,275,773 A | 1/1994 | Irie et al. | |
| 5,382,610 A | 1/1995 | Harada et al. | |
| 5,429,591 A * | 7/1995 | Yamamoto et al. | ............. 602/54 |
| 5,478,879 A | 12/1995 | Kajikawa et al. | |
| 5,610,208 A | 3/1997 | Dairoku et al. | |
| 5,633,316 A | 5/1997 | Gartner et al. | |
| 5,672,419 A | 9/1997 | Mukaida et al. | |
| 5,716,707 A | 2/1998 | Mukaida et al. | |
| 5,797,893 A * | 8/1998 | Wada et al. | ............. 604/372 |
| 6,071,976 A | 6/2000 | Dairoku et al. | |
| 6,087,450 A | 7/2000 | Breitbach et al. | |
| 6,228,930 B1 | 5/2001 | Dairoku et al. | |
| 6,359,049 B1 * | 3/2002 | Carrico et al. | ............. 524/414 |
| 6,414,214 B1 | 7/2002 | Engelhardt et al. | |
| 6,605,673 B1 * | 8/2003 | Mertens et al. | ............. 525/329.5 |
| 6,620,889 B1 * | 9/2003 | Mertens et al. | ............. 525/221 |
| 2002/0034911 A1 * | 3/2002 | Tsuchiya et al. | ............. 442/381 |

(Continued)

FOREIGN PATENT DOCUMENTS

EP    0 349 240    1/1990
(Continued)

OTHER PUBLICATIONS

Office Action in JP 2007-340689 dated Sep. 1, 2011.

*Primary Examiner* — Karuna P Reddy
(74) *Attorney, Agent, or Firm* — Roylance, Abrams, Berdo & Goodman, L.L.P.

(57) ABSTRACT

There are disclosed a water-absorbent resin composition and its production process, wherein the water-absorbent resin composition causes little gel-blocking and is excellent in the liquid permeability and liquid diffusibility and is high also in the absorption performances and further is strong also against the physical damage; and there are further disclosed a water-absorbent resin composition and its production process, wherein the water-absorbent resin composition has the following further advantages, in addition to the above, of involving little segregation of the metal compound and further having a dust prevention effect. One of water-absorbent resin compositions according to the present invention is a water-absorbent resin composition comprising water-absorbent resin particles obtained by polymerizing a monomer including acrylic acid and/or its salt, with the composition having a mass-average particle diameter of 100 to 600 μm and comprising water-soluble polyvalent metal salt particles and the water-absorbent resin particles that have been surface-crosslinked.

24 Claims, 6 Drawing Sheets

U.S. PATENT DOCUMENTS

2002/0128618 A1    9/2002  Frenz et al.
2002/0165288 A1*  11/2002  Frenz et al. .................. 521/50

FOREIGN PATENT DOCUMENTS

| | | |
|---|---|---|
| EP | 0 456 136 | 11/1991 |
| EP | 0 509 708 A | 10/1992 |
| EP | 0 640 330 | 3/1993 |
| EP | 0 612 533 A | 8/1994 |
| EP | 0 629 411 | 12/1994 |
| EP | 0 668 080 | 2/1995 |
| EP | 0 668 080 | 8/1995 |
| EP | 0 844 270 | 5/1998 |
| EP | 0 579 764 | 8/1999 |
| EP | 0 951 913 | 10/1999 |
| EP | 1 029 886 | 8/2000 |
| EP | 1 178 059 | 2/2002 |
| GB | 2 267 094 | 11/1993 |
| JP | 61-257235 | 11/1986 |
| JP | 62-7745 | 1/1987 |
| JP | 63-270741 | 11/1988 |
| JP | 64-56707 | 3/1989 |
| JP | 01-172457 | 7/1989 |
| JP | 4-4667 | 1/1992 |
| JP | 6-57010 | 3/1994 |
| JP | 6-248187 | 9/1994 |
| JP | 9-124879 | 5/1997 |
| JP | 9-235378 | 9/1997 |
| JP | 9-509591 | 9/1997 |
| JP | 9-290000 | 11/1997 |
| JP | 10-147724 | 6/1998 |
| JP | 2001-89527 | 4/2001 |
| JP | 2001-252307 | 9/2001 |
| JP | 2001-523287 | 11/2001 |
| JP | 2001-523289 | 11/2001 |
| JP | 2002-45395 | 2/2002 |
| JP | 2002-513043 | 5/2002 |
| JP | 2002-513059 | 5/2002 |
| JP | 2002-285021 | 10/2002 |
| JP | 2002-538275 | 11/2002 |
| JP | 2002-539281 | 11/2002 |
| WO | WO 91/18042 A | 11/1991 |
| WO | WO 95/22356 | 8/1995 |
| WO | WO 95/26209 | 10/1995 |
| WO | WO 96/01608 | 1/1996 |
| WO | WO 97/12575 | 4/1997 |
| WO | WO 97/24394 | 7/1997 |
| WO | WO 97/25013 | 7/1997 |
| WO | WO 97/34558 | 9/1997 |
| WO | WO 98/06364 | 2/1998 |
| WO | WO 98/37149 | 8/1998 |
| WO | WO 98/47454 | 10/1998 |
| WO | WO 98/48857 | 11/1998 |
| WO | WO 98/49221 | 11/1998 |
| WO | WO 99/55393 | 11/1999 |
| WO | WO 00/53644 | 9/2000 |
| WO | WO 00/53664 | 9/2000 |
| WO | WO 01/25290 | 4/2001 |
| WO | WO 01/66056 | 9/2001 |
| WO | 02/053199 | 7/2002 |

* cited by examiner (a)

(b)

(a)

(b)

WATER-ABSORBENT RESIN COMPOSITION AND ITS PRODUCTION PROCESS

TECHNICAL FIELD

The present invention relates to a water-absorbent resin composition and its production process, wherein the water-absorbent resin composition is used for sanitary materials such as disposable diapers, sanitary napkins, and so-called incontinent pads.

BACKGROUND ART

For sanitary materials such as disposable diapers, sanitary napkins, and incontinent pads, there are widely utilized absorbent structures comprising hydrophilic fibers (e.g. pulp) and water-absorbent resins as constituent materials for the purpose of absorption of body fluids.

In recent years, as to these sanitary materials, their high functionalization and thinning are making progress, so there is a tendency toward increases in the amount of the water-absorbent resin as used per piece of sanitary material and in the ratio of the water-absorbent resin relative to a whole absorbent structure comprising the water-absorbent resin and the hydrophilic fibers. Specifically, the ratio of the water-absorbent resin in the absorbent structure is raised by decreasing the amount of the hydrophilic fibers (which have a small bulk density) and increasing the amount of the water-absorbent resin (which has excellent water absorbency and a large bulk density) as used. Thereby the thinning of the sanitary materials is aimed at without lowering the water absorption quantity.

However, the sanitary materials, in which the ratio of the hydrophilic fibers has been decreased and that of the water-absorbent resin has been increased in the above way, are favorable from the viewpoint of simple storage of liquids, but rather involve problems in the case of consideration of distribution and diffusion of the liquids under circumstances of actual use as such as diapers. For example, the large amount of water-absorbent resin becomes a soft gel due to water absorption to cause a phenomenon "gel-blocking", thus dramatically deteriorating the ability to diffuse the liquids in the sanitary materials. In order to avoid such problems to maintain absorption properties of the absorbent structure, the ratios of the hydrophilic fibers and the water-absorbent resin have axiomatically been limited, so a limit has occurred also to the thinning of the sanitary materials.

As means for preventing the gel-blocking to thus obtain the water-absorbent resin excellent in the liquid permeability and liquid diffusibility, there are known the following arts in which metal compounds (e.g. metal salts, metal cations) are added to water-absorbent resins.

There is known a water-insoluble water-absorbent resin composition obtained by adding water, containing a salt and/or hydroxide of a polyvalent metal, to a water-absorbent resin (patent document 1).

There is known a process for production of a water-absorbent resin in which a water-absorbent resin is treated with an aluminum compound in the presence of a polyhydric alcohol and water, wherein the aluminum compound is reactable with the water-absorbent resin (patent document 2).

There is known a process for production of a water-absorbent resin in which a water-absorbent resin is treated with an aluminum compound and a crosslinking agent in the presence of a polyhydric alcohol and water, wherein: the aluminum compound is reactable with the water-absorbent resin, and the crosslinking agent has not fewer than two functional groups reactable with the water-absorbent resin (patent document 3).

There is known a process for production of water-absorbent resin particles having the modified particulate brittleness, in which process, to water-absorbent resin particles obtained by heat-crosslinking of surfaces and their neighborhood of particles of a water-absorbent resin, there are added, after this heat-crosslinking, water in which an inorganic salt is dissolved in a concentration of 5 to 50 weight % relative to water and/or water in which an inorganic hydroxide is dissolved in a concentration of 5 to 50 weight % relative to water, thereby adjusting the water content to 3-9% (patent document 4).

There is known a polymer produced by a process in which a water-absorbent resin is treated with a polyol and a cation which is in a state of an aqueous solution and then surface-crosslinked at 150-300° C. (patent document 5).

There is known a polymer produced by a process in which a water-absorbent resin is treated with an organic surface-secondary-crosslinking agent (except polyols) and a cation which is in a state of an aqueous solution and then surface-crosslinked (patent document 6).

There is known a composition comprising aqueous-fluid-absorbent polymer particles having been heat-treated at a temperature higher than 170° C. for more than 10 minutes, wherein the composition is remoisturized with an aqueous additive solution in the absence of an organic solvent or a water-insoluble and non-water-swellable powder after the heat-treatment and has a water content of 1-10 weight % based on the total weight of the composition and displays an absorption capacity of more than 20 g/g under 0.3 psi in 60 minutes (patent document 7).

These (patent documents 1 to 7) are arts in which the metal compounds (e.g. metal salts, metal cations) are added in aqueous solution states. As to these arts, because the metal compounds (e.g. metal salts, metal cations) are added in aqueous solution states, the metal components unfavorably permeate the inside of the water-absorbent resins, thus resulting in insufficiency of the effect of enhancing the liquid permeability and liquid diffusibility to a degree corresponding to the addition amount. In addition, because the metal components permeate the inside of the water-absorbent resins, there have unfavorably occurred deteriorations of such as absorption capacity without load and absorption capacity under load.

There is known a modified water-insoluble water-absorbent resin composition obtained by adding water to a mixture of a water-absorbent resin and a salt and/or hydroxide of a polyvalent metal (patent document 8).

There is known a method in which: a water-absorbent resin and a polyvalent metal salt are mixed together, and then the resultant mixture is brought into close contact with a binder in the absence of a volatile alcohol (patent document 9).

As to these arts (patent documents 8 to 9), there have been problems such that: the dissolved metal salt causes binding between particles to thus easily form a strong agglomerate and, in the case where this agglomerate is crushed by physical damage such as during the actual production or practical use, the absorption capacity under load is deteriorated. In addition, there have also been problems such that: the dissolved metal salt unfavorably goes so far as permeating into particles of the water-absorbent resin. The case where particles of the polyvalent metal salt having small particle diameters are used has been remarkable for the aforementioned permeation. Because of this permeation, there have been the same problems as the aforementioned. Specifically, the effect of enhancing the liquid permeability and liquid diffusibility to a degree corresponding to the addition amount has been insufficient or, because the metal components permeate the inside of the water-absorbent resins, there have unfavorably occurred deteriorations of such as absorption capacity without load and absorption capacity under load. In addition, as to particles of the polyvalent metal salt having comparatively large particle diameters, no sufficient binding force between particles can be obtained with the binder, and therefore such as release or elimination unfavorably occurs, so that problems of such as segregation of the metal compounds (e.g. metal salts) have also been caused.

As to other than these methods, for example, as to a method in which a water-absorbent resin and a metal compound (e.g. metal salt) are dry-blended together, particles are mixed with each other. Therefore, there is a possibility of occurrence of problems such that the segregation occurs to thus result in unstable performances of the water-absorbent resin.

As means for preventing the gel-blocking to thus obtain the water-absorbent resin excellent in the liquid permeability and liquid diffusibility, there are known some other arts besides the above arts as follows.

For example, there are proposed such as: a method in which two kinds of water-absorbent resins different as to water absorption performance are used (patent document 10); a method in which a composition containing a cationic ion-exchange hydrogel-forming polymer and an anionic ion-exchange hydrogel-forming polymer is used (patent document 11); and a method in which a water-absorbent resin having a high surface-crosslinking density is used (patent document 12). However, they have problems such that the absorption properties are unsatisfactory as the absorbent structure having a high water-absorbent resin concentration or that the cost is high.

In addition, a water-absorbent resin which contains a large amount of fine powder due to such as abrasion in processes for production of the water-absorbent resin has a tendency to cause the gel-blocking. Therefore, there is proposed a method in which the water-absorbent resin is made to contain water in an amount of not smaller than 3%, thereby improving the brittleness (patent document 13). However, there are problems such that the absorption capacity is deteriorated, and that, when water is added to the water-absorbent resin, this resin swells to thus form particles having too large particle diameters. In addition, it is also proposed that a special stirring apparatus is used to reduce the formation of the fine powder in processes for production of the water-absorbent resin (patent document 14).

In addition, there are known such as: a method in which a water-absorbent resin is mixed with a powder of an organic or inorganic water-soluble salt (specific salt such as thiourea, saccharide, or carboxylate salt), thereby enhancing the absorption of blood (patent document 15); a method in which a water-absorbent resin and a permeability-retaining agent (e.g. silica, alumina, titania, clay, emulsion-polymerized material, precipitation-polymerized material) are mixed together by a Vortex Mixer and then subjected to mechanical stress by such as Osterizer blender (patent document 16); a method in which a water-insoluble and water-swellable hydrogel is coated with steric or electrostatic spacers (patent document 17); a method in which a water-absorbent resin having been crosslinked with a specific metal ion is used (patent documents 18 and 19); and a super-water-absorbent resin composition comprising a super-water-absorbent resin and a fine powder of an aggregate of a hydro-oxide which contains two kinds of metals M1 and M2 at least partially having an -M1-O-M2- bond (patent document 20).

As to these publicly known methods (patent documents 15 to 20), the gel-blocking can be prevented, but there have occurred problems such that the durability of the performance to diffuse liquids in diapers, particularly, the Saline Flow Conductivity (hereinafter abbreviated to SFC), is low. Or, even if the performance to diffuse the liquids is enough, there is not taken into consideration various performance deteriorations due to such as mechanical impact or friction which the water-absorbent resin undergoes when it is produced or used to produce absorbent articles, and therefore no sufficient performance can be maintained in the actual production. For example, as the case may be, even if improvement effects are seen in laboratories, those effects are not seen or are deteriorated when the production is carried out with a production machine involving the step in which physical energy works against the powder such as stirring or pneumatic transportation.

There is known a water-absorbing agent comprising 100 weight parts of water-absorbent resin particles and 1 to 30 weight parts of a heat-fusible resin powder having a melting point in the range of 50 to 160° C. (patent document 21).

In this art (patent document 21), there is disclosed a method in which the water-absorbent resin particles and the heat-fusible resin powder having a melting point in the range of 50 to 160° C. are heat-treated after or during their mixing, whereby the heat-fusible resin powder is fixed to the water-absorbent resin particles. Such a heat-fusible resin powder is used for the purpose of enhancing the fixability to fibers such as pulp, in other words, as a binder for the fibers and the water-absorbent resin particles. However, such a heat-fusible resin powder enhances the fixability of the water-absorbent resin particles to the fibers, but has no interactions with a carboxyl group. Therefore, it has been impossible to obtain the effect of enhancing the liquid permeability and liquid diffusibility of the water-absorbent resin. In addition, in the case where the heat-fusible resin powder has strong hydrophobicity, it may cause such as deterioration of the capillary suction force of the resultant water-absorbent resin composition. Therefore, the resultant water-absorbent resin composition has not necessarily been a water-absorbent resin composition having sufficient performances.

[Patent document 1] JP-A-007745/1987 (Kokai)
[Patent document 2] JP-A-270741/1988 (Kokai)
[Patent document 3] JP-A-056707/1989 (Kokai)
[Patent document 4] JP-A-124879/1997 (Kokai)
[Patent document 5] JP-A-539281/2002 (Kohyo)
[Patent document 6] JP-A-538275/2002 (Kohyo)
[Patent document 7] JP-A-523287/2001 (Kohyo)
[Patent document 8] JP-A-257235/1986 (Kokai)
[Patent document 9] JP-A-523289/2001 (Kohyo)
[Patent document 10] JP-A-252307/2001 (Kokai)
[Patent document 11] pamphlet of WO 98/037149
[Patent document 12] JP-A-057010/1994 (Kokai)
[Patent document 13] pamphlet of WO 01/25290
[Patent document 14] pamphlet of WO 97/24394
[Patent document 15] U.S. Pat. No. 4,693,713
[Patent document 16] pamphlet of WO 01/66056
[Patent document 17] US 2002/0128618A1
[Patent document 18] JP-A-513043/2002 (Kohyo)
[Patent document 19] JP-A-513059/2002 (Kohyo)
[Patent document 20] JP-A-147724/1998 (Kokai)
[Patent document 21] JP-A-248187/1994 (Kokai)

DISCLOSURE OF THE INVENTION

Objects of the Invention

An object of the present invention is to provide a water-absorbent resin composition and its production process, wherein the water-absorbent resin composition causes little gel-blocking and is excellent in the liquid permeability and liquid diffusibility and is high also in the absorption performances (e.g. absorption capacity without load, absorption capacity under load, capillary absorption capacity) and further is strong also against the physical damage such as during the actual production or practical use.

Also, another object of the present invention is to provide a water-absorbent resin composition and its production process, wherein the water-absorbent resin composition has the following further advantages, in addition to the above, of involving little segregation of the metal compound (e.g. metal salt), and being excellent also in the handling property during the moisture absorption, and further having a dust prevention effect.

SUMMARY OF THE INVENTION

The present inventors diligently studied to solve the aforementioned problems. As a result, they have found out that: if there is constructed a water-absorbent resin composition which comprises water-absorbent resin particles and water-soluble polyvalent metal salt particles, wherein the water-absorbent resin particles are obtained by polymerizing a monomer including acrylic acid and/or its salt, and wherein the water-absorbent resin particles are surface-crosslinked ones, and wherein the water-absorbent resin composition has a mass-average particle diameter of 100 to 600 µm, then the above problems can successfully be solved, because the resultant water-absorbent resin composition causes little gel-blocking and is excellent in the liquid permeability and liquid diffusibility and is high also in the absorption performances (e.g. absorption capacity without load, absorption capacity under load, capillary absorption capacity) and further is strong also against the physical damage such as during the actual production or practical use. At the same time, the present inventors have found out also that: such a water-absorbent resin composition is a water-absorbent resin composition which displays a high saline flow conductivity (SFC) and is excellent in the retention ratio of the saline flow conductivity (SFC) after a paint shaker test and in the retention ratio of the saline flow conductivity (SFC) after a long-term liquid absorption.

In addition, the present inventors have further found out that: if, in a process for production of a water-absorbent resin composition in which a polyvalent metal is fixed to surfaces of water-absorbent resin particles, there are involved a step in which a binder (e.g. water) is beforehand added to the water-absorbent resin particles to thus put them in a state where the binder is permeated across surfaces of the water-absorbent resin particles and a step in which they are thereafter mixed with water-soluble polyvalent metal salt particles, then the above problems can successfully be solved, because: the permeation of the polyvalent metal into the water-absorbent resin particles can effectively be prevented, and further, the polyvalent metal is fixed all over the surfaces of the water-absorbent resin particles uniformly and moderately (i.e. in a state where the fixation is incomplete, but is not so weak as to enable free migration), and consequently, the gel-blocking can sufficiently be prevented, and therefore excellent liquid permeability and liquid diffusibility can be displayed and also excellent absorption performances can be displayed, and further, the resultant water-absorbent resin composition comes into a state which is strong also against the physical damage such as during the actual production or practical use.

Moreover, the present inventors have further found out that: if at least a part of a metal compound is fused to surfaces of water-absorbent resin particles in a water-absorbent resin composition comprising the water-absorbent resin particles and the metal compound wherein the water-absorbent resin particles are obtained by polymerizing a monomer including acrylic acid and/or its salt, then surprisingly the gel-blocking can sufficiently be prevented, and therefore excellent liquid permeability and liquid diffusibility can be displayed and also excellent absorption performances can be displayed, and further, the resultant water-absorbent resin composition comes into a state which is strong also against the physical damage such as during the actual production or practical use, and besides, this composition involves little segregation of the metal compound (e.g. metal salt), and is excellent also in the handling property during the moisture absorption, and further has a dust prevention effect.

That is to say, a first water-absorbent resin composition according to the present invention (which may hereinafter be referred to as water-absorbent resin composition (1)) is a water-absorbent resin composition comprising water-absorbent resin particles obtained by polymerizing a monomer including acrylic acid and/or its salt, with the composition having a mass-average particle diameter of 100 to 600 µm and comprising water-soluble polyvalent metal salt particles and the water-absorbent resin particles that have been surface-crosslinked.

As to the first water-absorbent resin composition according to the present invention, it is favorable that at least a part of the water-absorbent resin particles are agglomerates.

As to the first water-absorbent resin composition according to the present invention, it is favorable that the water-soluble polyvalent metal salt particles are particles of an aluminum salt having water of crystallization.

As to the first water-absorbent resin composition according to the present invention, it is favorable that the water-absorbent resin particles are those which have been surface-crosslinked with a polyhydric alcohol.

Also, the first water-absorbent resin composition according to the present invention is a water-absorbent resin composition comprising water-absorbent resin particles and water-soluble polyvalent metal salt particles, wherein the water-absorbent resin particles are obtained by polymerizing a monomer including acrylic acid and/or its salt, with the composition of which the saline flow conductivity is at least 50 ($\times 10^{-7} \cdot cm^3 \cdot s \cdot g^{-1}$) and of which the retention ratio of the saline flow conductivity is not less than 40%.

As to the first water-absorbent resin composition according to the present invention, favorably, its retention ratio of the saline flow conductivity after a paint shaker test is not less than 70%.

A first process according to the present invention for production of a water-absorbent resin composition (which may hereinafter be referred to as production process (1)) is characterized by comprising the steps of:

adding a binder to water-absorbent resin particles obtained by polymerizing a monomer including acrylic acid and/or its salt; and then mixing the binder and the water-absorbent resin particles with water-soluble polyvalent metal salt particles.

As to the first process according to the present invention for production of a water-absorbent resin composition, it is favorable that the water-absorbent resin particles are surface-crosslinked ones.

As to the first process according to the present invention for production of a water-absorbent resin composition, it is favorable that the binder contains a surface-crosslinking agent.

As to the first process according to the present invention for production of a water-absorbent resin composition, it is favorable that the binder includes water and/or a polyhydric alcohol.

As to the first process according to the present invention for production of a water-absorbent resin composition, it is favorable that, when the binder is added to the water-absorbent resin particles, the temperature of the water-absorbent resin particles is in the range of 40 to 100° C.

A second water-absorbent resin composition according to the present invention (which may hereinafter be referred to as water-absorbent resin composition (2)) comprises water-absorbent resin particles and a metal compound, wherein the water-absorbent resin particles are obtained by polymerizing a monomer including acrylic acid and/or its salt, and wherein:

the metal compound is one or not fewer than two members selected from among alkaline metal salts and polyvalent metal salts (except polyvalent metal salts of organic acids having not fewer than 7 carbon atoms per molecule); and at least a part of the metal compound is fused to surfaces of the water-absorbent resin particles.

As to the second water-absorbent resin composition according to the present invention, it is favorable that the water-absorbent resin particles are materials having been surface-crosslinked with a compound having at least two functional groups which make a dehydration reaction or transesterification reaction with a carboxyl group.

As to the second water-absorbent resin composition according to the present invention, it is favorable that at least a part of the metal compound is fused in the form of coating at least a part of surfaces of the water-absorbent resin particles in a layered state As to the second water-absorbent resin composition according to the present invention, it is favorable that the metal compound has a melting point of not higher than 250° C.

As to the second water-absorbent resin composition according to the present invention, it is favorable that the metal compound is a water-soluble polyvalent metal salt.

As to the second water-absorbent resin composition according to the present invention, it is favorable that the metal compound is a water-soluble polyvalent metal salt having water of hydration and containing aluminum.

As to the second water-absorbent resin composition according to the present invention, favorably, it displays an absorption capacity of not less than 20 g/g under load.

As to the second water-absorbent resin composition according to the present invention, favorably, it displays a saline flow conductivity of not less than 30 ($\times 10^{-7} \cdot cm^3 \cdot s \cdot g^{-1}$) for a 0.69 mass % physiological saline solution.

A second process according to the present invention for production of a water-absorbent resin composition (which may hereinafter be referred to as production process (2)) is a process for production of a water-absorbent resin composition which includes water-absorbent resin particles and a metal compound, wherein the water-absorbent resin particles are obtained by polymerizing a monomer including acrylic acid and/or its salt, and wherein:

the metal compound is one or not fewer than two members selected from among alkaline metal salts and polyvalent metal salts (except polyvalent metal salts of organic acids having not fewer than 7 carbon atoms per molecule);

with the process comprising the steps of:

heating the water-absorbent resin particles and/or the metal compound to a temperature of not lower than the melting point of the metal compound; and thereby fusing at least a part of the metal compound to surfaces of the water-absorbent resin particles.

As to the second process according to the present invention for production of a water-absorbent resin composition, it is favorable that the fusion is carried out under stirring of the water-absorbent resin particles and/or the metal compound.

As to the second process according to the present invention for production of a water-absorbent resin composition, it is favorable that the fusion is carried out after a surface-crosslinking treatment of the water-absorbent resin particles.

As to the second process according to the present invention for production of a water-absorbent resin composition, it is favorable that the metal compound has a melting point of not higher than 250° C.

As to the second process according to the present invention for production of a water-absorbent resin composition, it is favorable that the metal compound is a water-soluble polyvalent metal salt having water of hydration and containing aluminum.

Effects of the Invention

The present invention can provide a water-absorbent resin composition and its production process, wherein the water-absorbent resin composition causes little gel-blocking and is excellent in the liquid permeability and liquid diffusibility and is high also in the absorption performances (e.g. absorption capacity without load, absorption capacity under load, capillary absorption capacity) and further is strong also against the physical damage such as during the actual production or practical use. Also, the present invention can further provide a water-absorbent resin composition and its production process, wherein the water-absorbent resin composition has the following further effects, in addition to the above, of involving little segregation of the metal compound (e.g. metal salt), and being excellent also in the handling property during the moisture absorption, and further having a dust prevention effect.

EXPLANATION OF THE SYMBOLS

Figure 1:
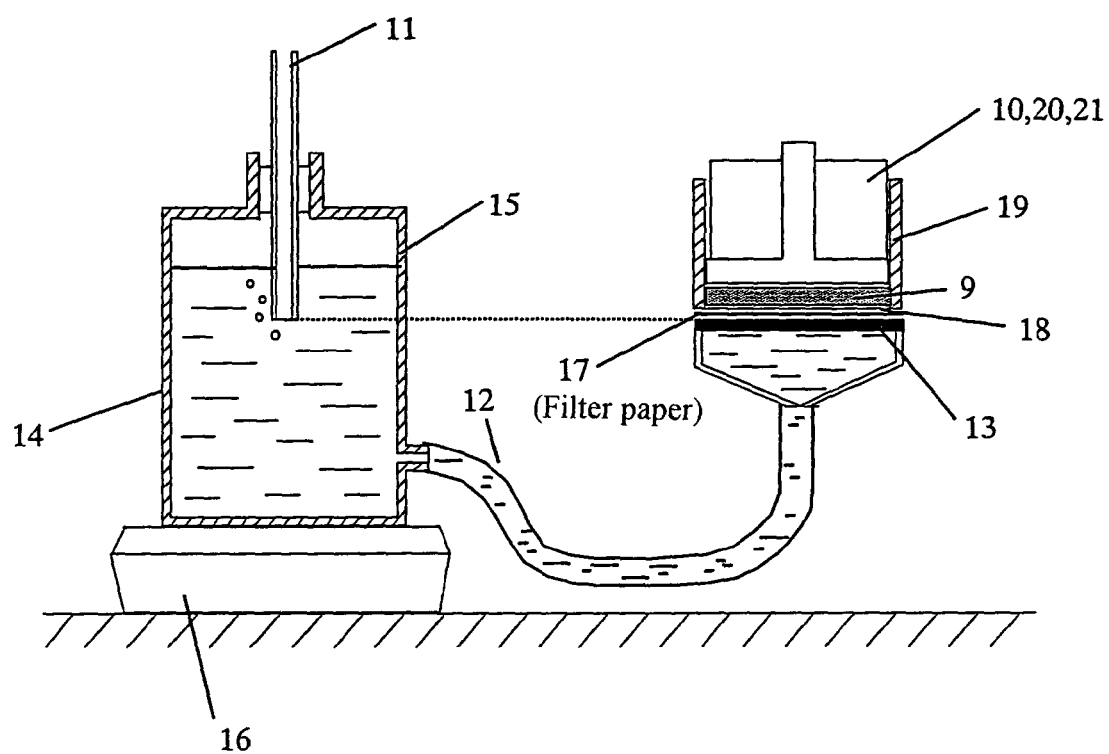
FIG. 1 is a schematic sectional view of a measurement apparatus as used for measuring the AAP (method A).

| | |
|---|---|
| 1: | Porous glass plate |
| 2: | Glass filter |
| 3: | Conduit |
| 4: | Liquid storage container |
| 5: | Supporting ring |
| 6: | 0.90 mass % physiological saline solution |
| 7: | Balance |
| 8: | Stand |
| 9: | Specimen to be measured (e.g. water-absorbent resin particles or water-absorbent resin composition) |
| 10: | Load (0.41 kPa (0.06 psi)) |
| 11: | Air-intake pipe |
| 12: | Conduit |
| 13: | Glass filter |
| 14: | 0.90 mass % physiological saline solution |
| 15: | Liquid storage container |
| 16: | Balance |
| 17: | Filter paper |
| 18: | Metal gauze |
| 19: | Plastic cylinder |
| 20: | Load (2.07 kPa (0.3 psi)) |
| 21: | Load (4.83 kPa (0.7 psi)) |
| 31: | Tank |
| 32: | Glass tube |
| 33: | 0.69 mass % aqueous sodium chloride solution |
| 34: | L-tube having cock |
| 35: | Cock |
| 40: | Receptacle |
| 41: | Cell |
| 42: | Stainless metal gauze |
| 43: | Stainless metal gauze |
| 44: | Swollen gel |
| 45: | Glass filter |
| 46: | Piston |
| 47: | Holes in piston |
| 48: | Collecting receptacle |
| 49: | Balance |
| 100: | Plastic supporting cylinder |
| 101: | Stainless metal gauze of 400 meshes |
| 102: | Swollen gel |
| 103: | Piston |
| 104: | Load (weight) |
| 105: | Petri dish |
| 106: | Glass filter plate |
| 107: | Filter paper |
| 108: | 0.90 mass % physiological saline solution |

DETAILED DESCRIPTION OF THE INVENTION

Hereinafter, the present invention is described in detail. Incidentally, the water-absorbent resin composition according to the present invention is a composition comprising a water-absorbent resin (water-absorbent resin particles) as the main component, and is a particulate composition comprising the water-absorbent resin in an amount of favorably 80 to 100 mass % (or weight %: in the present invention, the weight and the mass have the same meaning, and their uses herein are unified into the mass), more favorably 90 to 100 mass %, and is used favorably for sanitary materials (e.g. disposable diapers, sanitary napkins, incontinent pads, and medical pads).

[Water-Absorbent Resin Particles]:

The water-absorbent resin particles, as used in the present invention, are particles of a water-insoluble, water-swellable, and hydrogel-formable polymer (which may hereinafter be referred to as water-absorbent resin) obtainable by a process including the step of polymerizing a hydrophilic monomer, and has an absorption capacity of at least not less than 10 times for a physiological saline solution, and is the shape of spherical or irregular particles. Incidentally, in the present invention, the water-absorbent resin particles may be referred to simply as water-absorbent resin.

Specific examples of the water-insoluble, water-swellable, and hydrogel-formable polymer include: partially-neutralized and crosslinked polymers of poly(acrylic acids) (e.g. U.S. Pat. No. 4,625,001, U.S. Pat. No. 4,654,039, U.S. Pat. No. 5,250,640, U.S. Pat. No. 5,275,773, EP 0456136); crosslinked and partially-neutralized graft polymers of starch-acrylic acid (U.S. Pat. No. 4,076,663); copolymers of isobutylene-maleic acid (U.S. Pat. No. 4,389,513); saponified copolymers of vinyl acetate-acrylic acid (U.S. Pat. No. 4,124,748); hydrolyzed (co)polymers of acrylamide (U.S. Pat. No. 3,959,569); and hydrolyzed polymers of acrylonitrile (U.S. Pat. No. 3,935,099). The water-absorbent resin, as used in the present invention, is favorably a water-absorbent resin including a crosslinked poly(acrylic acid) (salt) polymer obtained by a process including the step of polymerizing a monomer including acrylic acid and/or its salt. The crosslinked poly(acrylic acid) (salt) polymer in the present invention is a crosslinked polymer obtained by a process including the step of polymerizing a monomer including acrylic acid and/or its salt in an amount of not smaller than 50 mol %, favorably not smaller than 70 mol %, more favorably not smaller than 90 mol %. In addition, it is favorable that 50 to 90 mol %, preferably 60 to 80 mol %, of acid groups in the polymer are neutralized. As examples of the salt, there can be cited such as: alkaline metal (e.g. sodium, potassium, lithium) salts, ammonium salts, and amine salts. The neutralization of the water-absorbent resin for forming the salt may be carried out in a monomer state before the polymerization, or may be carried out in a polymer state on the way of or after the polymerization, or may be carried out both in these states.

The crosslinked poly(acrylic acid) (salt) polymer, which is a water-absorbent resin as favorably used in the present invention, may be a copolymer obtained by copolymerizing another monomer jointly with the monomer used as the main component (acrylic acid and/or its salt), if necessary. Specific examples of the above other monomer include: anionic unsaturated monomers (e.g. methacrylic acid, maleic acid, vinylsulfonic acid, styrenesulfonic acid, 2-(meth)acrylamido-2-methylpropanesulfonic acid, 2-(meth)acryloylethanesulfonic acid, 2-(meth)acryloylpropanesulfonic acid) and their salts; nonionic-hydrophilic-group-containing unsaturated monomers (e.g. acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, N-acryloylpyrrolidine, N-vinylacetamide); and cationic unsaturated monomers (e.g. N,N-dimethylaminoethyl (meth)acrylate, N,N-diethylaminoethyl (meth)acrylate, N,N-dimethylaminopropyl (meth)acrylate, N,N-dimethylaminopropyl(meth)acrylamide, and their quaternary salts). The amount of these monomers used as monomers other than acrylic acid and/or its salt is favorably in the range of 0 to 30 mol %, more favorably 0 to 10 mol %, of the entire monomers.

The water-absorbent resin, as used in the present invention, is a crosslinked polymer having a internal crosslinked structure.

As to methods for introducing the internal crosslinked structure into the water-absorbent resin as used in the present invention, examples thereof include: a method in which the introduction is carried out by self-crosslinking without any crosslinking agent; and a method in which the introduction is carried out by copolymerization or reaction with an internal-crosslinking agent having at least two polymerizable unsaturated groups and/or at least two reactive groups per molecule. A favorable example is the method in which the introduction is carried out by copolymerization or reaction with the internal-crosslinking agent.

Specific examples of these internal-crosslinking agents include: N,N'-methylenebis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerol tri(meth)acrylate, glycerol acrylate methacrylate, ethylene-oxide-modified trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, polyethylenimine, and glycidyl (meth)acrylate. These internal-crosslinking agents may be used either alone respectively or in combinations with each other. Above all, from the viewpoint of such as water absorption properties of the obtained water-absorbent resin, it is favorable that a compound having at least two polymerizable unsaturated groups is essentially used as the internal-crosslinking agent. The amount of the above internal-crosslinking agent as used is favorably in the range of 0.005 to 3 mol %, more favorably 0.01 to 1.5 mol %, relative to the entire monomers.

When the polymerization is carried out, there can be added such as: hydrophilic polymers (e.g. starch, cellulose, starch derivatives, cellulose derivatives, polyvinyl alcohol, poly(acrylic acid) (salts), and crosslinked poly(acrylic acid) (salts)); and chain transfer agents such as hypophosphorous acid (salts).

When the above monomer including acrylic acid and/or its salt as the major component is polymerized to obtain the water-absorbent resin used in the present invention, then bulk polymerization, reversed-phase suspension polymerization, or precipitation polymerization may be carried out, but, from the viewpoint of the performance or the easiness in controlling the polymerization, it is favorable to carry out aqueous solution polymerization in which the monomer is used in the form of an aqueous solution. Such polymerization methods are disclosed in such as U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683,274, U.S. Pat. No. 4,690,996, U.S. Pat. No. 4,721,647, U.S. Pat. No. 4,738,867, U.S. Pat. No. 4,748,076, and EP 1178059.

When the polymerization is carried out, there may, for example, be used the following: radical polymerization initiators such as potassium persulfate, ammonium persulfate, sodium persulfate, t-butyl hydroperoxide, hydrogen peroxide, and 2,2'-azobis(2-amidinopropane) dihydrochloride; and active energy rays such as ultraviolet rays and electron beams. In addition, in the case where the radical polymerization initiators are used, they may be used jointly with reducing agents such as sodium sulfite, sodium hydrogensulfite, ferrous sulfate, and L-ascorbic acid to carry out redox polymerization. The amount of these polymerization initiators as used is favorably in the range of 0.001 to 2 mol %, more favorably 0.01 to 0.5 mol %, relative to the entire monomers.

The shape of the water-absorbent resin, obtained by the above polymerization, is generally such as irregularly pulverized shape, spherical shape, fibrous shape, bar shape, approximately spherical shape, or flat shape. However, the water-absorbent resin as used in the present invention is, desirably, particulate. If a water-absorbent resin of the irregularly pulverized shape as obtained by pulverization after drying is used, there are advantages in that the effects of the present invention are more enhanced.

The water-absorbent resin, as used in the present invention, is favorably that of which the surfaces and their neighborhood have further been crosslinked with a surface-crosslinking agent.

Examples of the surface-crosslinking agent usable for the surface-crosslinking treatment include: organic surface-crosslinking agents which have at least two functional groups reactable with a functional group (particularly, a carboxyl group) of the water-absorbent resin; and polyvalent metal compounds. Examples thereof include: polyhydric alcohol compounds (e.g. ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol); epoxy compounds (e.g. ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol); polyamine compounds (e.g. ethylenediamine, diethylenetriamine, triethylenetetramine, tetraethylenepentamine, pentaethylenehexamine, and polyethylenimine) and their inorganic or organic salts (e.g. azetidinium salts); polyisocyanate compounds (e.g. 2,4-tolylene diisocyanate and hexamethylene diisocyanate); polyoxazoline compounds (e.g. 1,2-ethylenebisoxazoline); carbonic acid derivatives (e.g. urea, thiourea, guanidine, dicyandiamide, 2-oxazolidinone); alkylene carbonate compounds (e.g. 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, and 1,3-dioxopan-2-one); haloepoxy compounds (e.g. epichlorohydrin, epibromohydrin, and (α-methylepichlorohydrin) and their polyamine-added products (e.g. Kymene (registered trademark) produced by Hercules); silane coupling agents (e.g. γ-glycidoxypropyltrimethoxysilane and γ-aminopropyltriethoxysilane); oxetane compounds (e.g. 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, 3-butyl-3-oxetaneethanol, 3-chloromethyl-3-methyloxetane, 3-chloromethyl-3-ethyloxetane, and polyoxetane compounds); and polyvalent metallic compounds (e.g. hydroxides and chlorides of such as zinc, calcium, magnesium, aluminum, iron and zirconium). These surface-crosslinking agents may be used either alone respectively or in combinations with each other. Above all, the polyhydric alcohols are favorable, because they are high in safety and can enhance the hydrophilicity of water-absorbent resin particle surfaces. In addition, the use of the polyhydric alcohols enhance the affinity of water-absorbent resin particle surfaces to the polyvalent metal particles, so that interactions between the polyhydric alcohol residue and the polyvalent metal surface enables more uniform existence of the polyvalent metal particles on surfaces of the water-absorbent resin particles.

The amount of the surface-crosslinking agent, as used, is favorably in the range of 0.001 to 5 mass parts, per 100 mass parts of the solid content of the water-absorbent resin.

When the surface-crosslinking agent and the water-absorbent resin are mixed together, water may be used. The amount of water, as used, is favorably larger than 0.5 but not larger than 10 mass parts, more favorably in the range of 1 to 5 mass parts, per 100 mass parts of the solid content of the water-absorbent resin.

When the surface-crosslinking agent and/or its aqueous solution is mixed, a hydrophilic organic solvent and/or a third substance may be used as a mixing assistant.

In the case where the hydrophilic organic solvent is used, its examples include: lower alcohols (e.g. methyl alcohol, ethyl alcohol, n-propyl alcohol, isopropyl alcohol, n-butyl alcohol, isobutyl alcohol, and t-butyl alcohol); ketones (e.g. acetone); ethers (e.g. dioxane, tetrahydrofuran, and methoxy (poly)ethylene glycol); amides (e.g. ε-caprolactam and N,N-dimethylformamide); sulfoxides (e.g. dimethyl sulfoxide); and polyhydric alcohols (e.g. ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol). Though depending on such as kind, particle diameters, and water content of the water-absorbent resin, the amount of the hydrophilic organic solvent as used is favorably not larger than 10 mass parts, more favorably in the range of 0.1 to 5 mass parts, per 100 mass parts of the solid content of the water-absorbent resin. In addition, as the third substance, there may be caused to coexist those which are disclosed in EP 0668080, such as inorganic acids, organic acids, and polyamino acids. These mixing assistants may act as surface-crosslinking agents, but are favorably those which do not give a surface-crosslinked water-absorbent resin having low water absorption performance. Particularly, volatile alcohols having boiling points of lower than 150° C. are desirable in that they volatilize during the surface-crosslinking treatment and thus their residues do not remain.

When the water-absorbent resin and the surface-crosslinking agent are mixed together, there may be caused to coexist a noncrosslinkable water-soluble inorganic base (favorably: alkaline metal salts, ammonium salts, alkaline metal hydroxides, and ammonia or its hydroxide) and/or an irreducible alkaline-metal-salt pH buffer (favorably such as hydrogencarbonates, dihydrogenphosphates, and hydrogenphosphates) for the purpose of more uniformly mixing the water-absorbent resin and the surface-crosslinking agent together. The amount of these materials, as used, depends upon such as type or particle diameters of the water-absorbent resin, but is favorably in the range of 0.005 to 10 mass parts, more favorably 0.05 to 5 mass parts, per 100 mass parts of the solid content of the water-absorbent resin.

Although not especially limited, the method for mixing the water-absorbent resin and the surface-crosslinking agent together can be exemplified by such as: a method in which the water-absorbent resin is immersed into the hydrophilic organic solvent and then mixed with the surface-crosslinking agent that is, if necessary, dissolved in water and/or a hydrophilic organic solvent; and a method in which the surface-crosslinking agent that is dissolved in water and/or the hydrophilic organic solvent is spraywise or dropwise added directly to the water-absorbent resin to mix them together.

After the mixing of the water-absorbent resin and the surface-crosslinking agent, usually, a heating treatment is carried out to conduct the crosslinking reaction. Though depending on the surface-crosslinking agent as used, the temperature of the above heating treatment is favorably in the range of 40 to 250° C., more favorably 150 to 250° C. In the case where the treatment temperature is lower than 40° C., the absorption properties such as absorption capacity under a load are sometimes not sufficiently improved. In the case where the treatment temperature is higher than 250° C., the deterioration of the water-absorbent resin is sometimes caused, so that the performance is lowered, therefore caution is needed. The duration of the heating treatment is favorably in the range of 1 minute to 2 hours, more favorably 5 minutes to 1 hour.

There is no especial limitation on the particle diameters and particle diameter distribution of the water-absorbent resin as used in the present invention. However, if there is used a water-absorbent resin having comparatively small particle diameters and a particle diameter distribution such that the content of components having small particle diameters is high, then there are advantages in that the water absorption performances such as water absorption rate and capillary absorption capacity are greatly enhanced.

As to the water-absorbent resin as used in the present invention, it is favorable for enhancing the performances such as water absorption rate and capillary absorption capacity that the mass-average particle diameter is not larger than 500 μm, more favorably not larger than 400 μm. In addition, the ratio of particles having particle diameters of smaller than 300 μm in the water-absorbent resin is favorably not less than 10 mass %, more favorably not less than 30 mass %, still more favorably not less than 50 mass %, relative to the water-absorbent resin. A water-absorbent resin having such particle diameters either is that which is obtained by pulverizing a water-absorbent resin obtained by the aqueous solution polymerization, or can favorably be obtained by sieving the pulverized water-absorbent resin to thus regulate its particle diameters. In addition, it is also possible to use a water-absorbent resin obtained by a process including the steps of: agglomerating a fine powder of a water-absorbent resin having particle diameters of not larger than 300 μm; and then regulating the particle diameters of the agglomerated water-absorbent resin. Furthermore, it is also possible to use a water-absorbent resin obtained by a process in which irregularly pulverized particles which are primary particles obtained by pulverization are partially mixed with the agglomerated material of the fine powder. In the case of having been partially mixed with the agglomerated material of the water-absorbent resin, there can be obtained a water-absorbent resin composition according to the present invention which is still more excellent in the absorption properties such as water absorption rate and capillary absorption capacity. The amount of the agglomerated material of the fine powder, which is mixed, is favorably not smaller than 5 mass %, more favorably not smaller than 10 mass %, still more favorably not smaller than 15 mass %.

As methods for preparing the agglomerated material of the fine powder, it is possible to use publicly known arts to regenerate a fine powder. Examples of such usable arts include methods in which: warm water and a fine powder of a water-absorbent resin are mixed together and then dried (U.S. Pat. No. 6,228,930); a fine powder of a water-absorbent resin is mixed with an aqueous monomer solution, and then the resultant mixture is polymerized (U.S. Pat. No. 5,264,495); water is added to a fine powder of a water-absorbent resin, and then the resultant mixture is agglomerated under not less than a specific face pressure (EP 0844270); a fine powder of a water-absorbent resin is sufficiently wetted to thus form an amorphous gel, and then this gel is dried and pulverized (U.S. Pat. No. 4,950,692); and a fine powder of a water-absorbent resin and a polymer gel are mixed together (U.S. Pat. No. 5,478,879). However, there is favorably used the aforementioned method in which warm water and a fine powder of a water-absorbent resin are mixed together and then dried. Incidentally, the particle diameter is indicated by the sieve mesh opening size of the classification.

[Water-Soluble Polyvalent Metal Salt Particles]:

It has already been commonly known that a certain kind of inorganic compound particles prevent the gel-blocking to thus provide a water-absorbent resin with high distributing and diffusing abilities. However, the present inventors studied about a water-absorbent resin composition which displays high performance even in the case where, as is aforementioned, a water-absorbent resin has been damaged by such as pneumatic transportation which is usually included in processes for production of water-absorbent resins. As a result, the present inventors have found out that: unexpectedly, in the case where the water-soluble polyvalent metal salt particles are used as the inorganic compound particles, the effect of enhancing the liquid permeation rate under load is great and further, only in the case where the water-soluble polyvalent metal salt is not added to a water-absorbent resin in a state of an aqueous solution, but the water-soluble polyvalent metal salt is added to water-absorbent resin particles in a state of particles, there is obtained a water-absorbent resin composition which is excellent both in a performance of retaining the liquid permeation rate under load for a long time and in the physical damage resistance. In addition, the present inventors have found out also that: in the case where the water-soluble polyvalent metal salt particles are hydrous salt crystals, particularly the effects are great. As to the reason why the water-absorbent resin composition obtained by the dry mixing displays such effects, it is inferred (from great deterioration of the effects of the present invention as to a composition being in a state where the water-soluble polyvalent metal salt particles are dissolved to thus be in a non-particulate state by adding the water-soluble polyvalent metal salt to a water-absorbent resin in the form of an aqueous solution or adding water to a dry wise mixture of the water-absorbent resin particles and the water-soluble polyvalent metal salt particles) that: if the water-soluble polyvalent metal salt is intermingled with the water-absorbent resin particles in the form of particles, then, when the physical damage such as impact is done to the water-absorbent resin composition, the water-soluble polyvalent metal salt particles absorb the impact energy to thus reduce the damage to the water-absorbent resin. Hereupon, the impact energy can be considered as being consumed by pulverization of the water-soluble polyvalent metal salt particles and by uniformization due to rearrangement of the water-soluble polyvalent metal salt particles. Therefore, it can be considered as desirable that the water-soluble polyvalent metal salt particles are in a state of the dry wise mixture which can move with some degree of freedom rather than are entirely fixed on surfaces of the water-absorbent resin.

In addition to the above, the water-soluble polyvalent metal salt has an action of hydrophilizing the surfaces of the water-absorbent resin particles and, when the water-absorbent resin composition absorbs an aqueous liquid, the water-soluble polyvalent metal salt particles dissolve to thus make actions of ion-crosslinking the surfaces of the water-absorbent resin and keeping the spaces between water-absorbent resins wide. These actions have the effect of enhancing the liquid permeation rate under load. Hereupon, this effect is greater when the polyvalent metal exists in the periphery of and/or near the surfaces of the water-absorbent resin particles than when the polyvalent metal exists inside the water-absorbent resin particles. As to the water-absorbent resin composition as produced by adding the water-soluble polyvalent metal salt to a water-absorbent resin in the form of an aqueous solution or adding water to a dry wise mixture of the water-absorbent resin particles and the water-soluble polyvalent metal salt particles, much of the polyvalent metal salt has already permeated the inside of the water-absorbent resin, and therefore the effects of the polyvalent metal salt upon water-absorbent resin surfaces are low during the absorption of an aqueous liquid such as urine. As a result, the above water-absorbent resin composition is low in performance, particularly, in the liquid permeation rate under load, and its durability is also bad. In addition, because the permeated polyvalent metal salt reacts with the carboxyl group to thus form a crosslinked structure, the liquid permeability is deteriorated due to the damage done by the process. In comparison, because the water-soluble polyvalent metal salt usable in the present invention is mixed with the water-absorbent resin particles in the form of particles, the water-soluble polyvalent metal salt does not dissolve to act on the water-absorbent resin surfaces until the water-absorbent resin composition absorbs urine or an aqueous liquid. This action can more efficiently make the effects of the polyvalent metal salt upon the water-absorbent resin surfaces endure for a long time. In addition, the water-absorbent resin composition according to the present invention, in which the water-soluble polyvalent metal salt particles exist on surfaces of the water-absorbent resin particles, is excellent in the liquid permeability still after having been damaged by the process, because the water-soluble polyvalent metal salt particles exist on surfaces of the water-absorbent resin particles still after the composition has been damaged by the process. That it to say, the water-absorbent resin composition according to the present invention can be said to have a structure which effectively exercises the effects of the polyvalent metal without deteriorating the liquid absorption performance of the water-absorbent resin itself.

The water-soluble polyvalent metal salt particles, usable in the present invention, are particles of a salt of a metal having a valence of not less than 2 and are powdery. Taking it into consideration that the water-absorbent resin composition according to the present invention is utilized for absorbent structures for sanitary materials such as diapers, then it is favorable to select a water-soluble polyvalent metal salt which does not color the water-absorbent resin composition and which is low poisonous to human bodies.

For the purpose of more efficiently making the effects of the polyvalent metal salt endure for a long time during the liquid absorption, there is favorably selected and used the polyvalent metal salt which can dissolve in a concentration of not less than 5 mass %, more favorably not less than 10 mass %, still more favorably not less than 20 mass %, in pure water of normal temperature.

Examples of the water-soluble polyvalent metal salt particles, usable in the present invention, include aluminum chloride, poly(aluminum chloride), aluminum sulfate, aluminum nitrate, potassium aluminum bis(sulfate), sodium aluminum bis(sulfate), calcium chloride, calcium nitrate, magnesium chloride, magnesium sulfate, magnesium nitrate, zinc chloride, zinc sulfate, zinc nitrate, zirconium chloride, zirconium sulfate, and zirconium nitrate. In addition, also from the viewpoint of solubility into a liquid being absorbed such as urine, it is favorable to use these salts having water of crystallization. Particularly favorable are the aluminum compounds, above all, aluminum sulfate. Powders of hydrous crystals such as aluminum sulfate octadecahydrate and aluminum sulfate tetradeca- to octadecahydrates can most favorably be used.

From the viewpoint of mixability, it is favorable that the particle diameters of the water-soluble polyvalent metal salt particles, usable in the present invention, are smaller than those of the water-absorbent resin. The mass-average particle diameter is favorably not larger than 500 μm, more favorably not larger than 400 μm. From the viewpoint of performance, the water-soluble polyvalent metal salt particles include particles having particle diameters of not larger than 150 μm in an amount of more favorably not smaller than 20 mass %, most favorably not smaller than 30 mass %, relative to the water-soluble polyvalent metal salt particles.

As the behavior and state of the water-soluble polyvalent metal salt particles usable in the present invention, it is favorable from the viewpoint of damage mitigation that the particles are such as agglomerates. The bulk density is favorably not less than 0.5 g/cm$^3$, more favorably not less than 0.7 g/cm$^3$.

[Water-Absorbent Resin Composition (1)]:

The water-absorbent resin composition (1) according to the present invention is a water-absorbent resin composition comprising water-absorbent resin particles obtained by polymerizing a monomer including acrylic acid and/or its salt, with the composition having a mass-average particle diameter of 100 to 600 μm and comprising water-soluble polyvalent metal salt particles and the water-absorbent resin particles that have been surface-crosslinked.

Also, the water-absorbent resin composition (1) according to the present invention is a water-absorbent resin composition comprising water-absorbent resin particles and water-soluble polyvalent metal salt particles, wherein the water-absorbent resin particles are obtained by polymerizing a monomer including acrylic acid and/or its salt, with the composition of which the saline flow conductivity (SFC) is at least 50 ($\times 10^{-7} \cdot cm^3 \cdot s \cdot g^{-1}$) and of which the retention ratio of the saline flow conductivity (SFC) is not less than 40%.

The water-absorbent resin composition (1) according to the present invention comprises the water-absorbent resin particles as the main component and further comprises the water-soluble polyvalent metal salt particles, and is usually particulate and can be used favorably as an absorbent material for sanitary materials for absorption of urine, menstrual blood, sweat, and other body fluids.

Because the water-soluble polyvalent metal salt particles in the water-absorbent resin composition (1) according to the present invention are merely mixed with the water-absorbent resin particles in the form of particles, the water-soluble polyvalent metal salt particles exist on surfaces of the water-absorbent resin particles while still keeping their particulate shape, or exist in the periphery of the water-absorbent resin particles, for example, between particles of the water-absorbent resin, while still keeping their particulate shape. A favorable mode is a state where the water-soluble polyvalent metal salt particles substantially coexist uniformly with the water-absorbent resin particles. If the water-soluble polyvalent metal salt particles can maintain the particle shape in order to form such a state, then the mode may be that the water-soluble polyvalent metal salt particles are made to adhere weakly to the water-absorbent resin particles with such as a binder. It may be possible to observe these states from photographs taken with such as electron microscopes. However, they can be confirmed by dispersing and stirring the water-absorbent resin composition into an appropriate organic solvent or an appropriate gas and then separating the water-absorbent resin particles and the water-soluble polyvalent metal salt particles from each other by utilizing the difference between their specific gravities.

The water-absorbent resin composition (1) according to the present invention, favorably, includes the water-absorbent resin particles and the water-soluble polyvalent metal salt particles. At least a part of the aforementioned water-soluble polyvalent metal salt particles adhere weakly to water-absorbent resin particle surfaces by the binder. Therefore, the permeation of the polyvalent metal into the water-absorbent resin particles is effectively prevented, and further, the polyvalent metal is fixed all over the surfaces of the water-absorbent resin particles uniformly and moderately (i.e. in a state where the fixation is incomplete, but is not so weak as to enable free migration). Consequently, the gel-blocking can sufficiently be prevented, and therefore excellent liquid permeability and liquid diffusibility can be displayed and also excellent absorption performances can be displayed. Furthermore, the water-absorbent resin composition comes into a state which is strong also against the physical damage such as during the actual production or practical use. These states can also be observed from photographs taken with such as electron microscopes.

The water-absorbent resin particles, which are included in the water-absorbent resin composition (1) according to the present invention, are, favorably, surface-crosslink-treated ones.

The water-absorbent resin composition (1), according to the present invention, is in the form of particles having a mass-average particle diameter in the range of favorably 100 to 600 μm, more favorably 200 to 500 μm. In the case where the mass-average particle diameter is smaller than 100 μm, then, even if the water-soluble polyvalent metal salt particles are added, there is a possibility that it may be difficult to obtain the effects of the present invention. In the case where the mass-average particle diameter is larger than 600 μm, then there is a possibility that the water-soluble polyvalent metal salt particles may segregate to deteriorate the uniform mixability. In addition, the ratio of particles having particle diameters of smaller than 300 μm in the water-absorbent resin composition (1) is favorably not less than 10 mass %, more favorably not less than 30 mass %, still more favorably not less than 50 mass %, relative to the water-absorbent resin composition (1).

The water-absorbent resin composition (1), according to the present invention, favorably displays an absorption capacity without load (CRC) of not less than 20 (g/g), more favorably not less than 22 (g/g), still more favorably not less than 24 (g/g), yet still more favorably not less than 25 (g/g), particularly favorably not less than 27 (g/g). In the case where the absorption capacity without load (CRC) is less than 20 (g/g), the absorption efficiency is bad on an occasion of the use for sanitary materials such as diapers.

The water-absorbent resin composition (1), according to the present invention, favorably displays an absorption capacity under load (AAP) of not less than 16 (g/g), more favorably not less than 18 (g/g), still more favorably not less than 20 (g/g), yet still more favorably not less than 22 (g/g), particularly favorably not less than 24 (g/g), under a load of 0.7 psi. In the case where the absorption capacity under load (AAP) is less than 16 (g/g), the absorption efficiency is bad on an occasion of the use for sanitary materials such as diapers.

The water-absorbent resin composition (1), according to the present invention, favorably displays a saline flow conductivity (SFC) of not less than 50 ($\times 10^{-7} \cdot cm^3 \cdot s \cdot g^{-1}$), more favorably not less than 100 ($\times 10^{-7} \cdot cm^3 \cdot s \cdot g^{-1}$), still more favorably not less than 120 ($\times 10^{-7} \cdot cm^3 \cdot s \cdot g^{-1}$), particularly favorably not less than 150 ($\times 10^{-7} \cdot cm^3 \cdot s \cdot g^{-1}$). The saline flow conductivity (SFC) depends on the content of the water-absorbent resin composition in the sanitary material. The higher content needs the higher saline flow conductivity (SFC).

As to the water-absorbent resin composition (1) according to the present invention, it is desirable that the deterioration of the absorption capacity under load (AAP) of this water-absorbent resin composition, as compared with an absorption capacity under load (AAP) (under the same load) of the water-absorbent resin particles to which the water-soluble polyvalent metal salt particles have not yet been added, is small. The water-absorbent resin composition favorably maintains an absorption capacity under load of not less than 0.85 time, more favorably not less than 0.90 time, still more favorably not less than 0.95 time, in comparison with the absorption capacity under load (AAP) of the water-absorbent resin particles.

The water-absorbent resin composition (1), according to the present invention, displays an effect such that the deterioration of absorption performances is small even if it undergoes various physical energy (damage) during the production or practical use. That is to say, the water-absorbent resin composition (1), according to the present invention, is a water-absorbent resin composition which has the following absorption performances after physical energy has worked against the composition.

The water-absorbent resin composition (1), according to the present invention, favorably displays an absorption capacity without load after the paint shaker test (shaking at 800 cycles/min for 30 minutes) (CRC after PS) of not less than 20 (g/g), more favorably not less than 22 (g/g), still more favorably not less than 24 (g/g), yet still more favorably not less than 25 (g/g), particularly favorably not less than 27 (g/g). In the case where the absorption capacity without load after the paint shaker test (CRC after PS) is less than 20 (g/g), the absorption efficiency is bad on an occasion of the use for sanitary materials such as diapers.

The water-absorbent resin composition (1), according to the present invention, favorably displays a saline flow conductivity after the paint shaker test (SFC after PS) of not less than 50 ($\times 10^{-7} \cdot cm^3 \cdot s \cdot g^{-1}$), more favorably not less than 100 ($\times 10^{-7} \cdot cm^3 \cdot s \cdot g^{-}$), still more favorably not less than 120 ($\times 10^{-7} \cdot cm^3 \cdot s \cdot g^{-1}$), particularly favorably not less than 150 ($\times 10^{-7} \cdot cm^3 \cdot s \cdot g^{-1}$). The saline flow conductivity after the paint shaker test (SFC after PS) depends on the content of the water-absorbent resin composition in the sanitary material. The higher content needs the higher saline flow conductivity (SFC).

As to the water-absorbent resin composition (1) according to the present invention, the ratio of a saline flow conductivity (SFC) after the paint shaker test to an SFC before the PS test, namely, the retention ratio of the saline flow conductivity after the paint shaker test (retention ratio of SFC after PS), is favorably not less than 70%, more favorably not less than 80%, still more favorably not less than 90%, particularly favorably not less than 100%.

The water-absorbent resin composition (1), according to the present invention, can maintain a high saline flow conductivity (SFC) even when used in sanitary materials for a long time.

As to the water-absorbent resin composition (1) according to the present invention, the ratio of a saline flow conductivity (SFC) after a swelling time of 120 minutes to a saline flow conductivity (SFC) after a swelling time of 60 minutes, namely, the retention ratio of the saline flow conductivity (retention ratio of SFC), is favorably not less than 40%, more favorably not less than 50%, still more favorably not less than 60%. As to conventional water-absorbent resins (or water-absorbent resin compositions) to which metal particles have been added, if they are measured for a swelling duration of more than 60 minutes in the test for the saline flow conductivity (SFC), then a rapid fall of the liquid permeation rate is seen.

The water-absorbent resin composition (1), according to the present invention, further has a feature of generating little dust. As to the water-absorbent resin composition (1) according to the present invention, the dust generation degree is favorably not more than 0.25 ($mg/m^3$), more favorably not more than 0.23 ($mg/m^3$), still more favorably not more than 0.20 ($mg/m^3$), yet still more favorably not more than 0.17 ($mg/m^3$), particularly favorably not more than 0.15 ($mg/m^3$).

The water-absorbent resin composition (1) according to the present invention is excellent in the wettability to aqueous liquids. Particularly above all, a water-absorbent resin composition including water-absorbent resin particles which have been surface-crosslinked with the polyhydric alcohol is excellent in the wettability and contributes to the enhancement of the absorption performances. The wettability of the water-absorbent resin composition to aqueous liquids can be evaluated by measuring the contact angle. It is not easy to precisely measure the contact angle of a liquid with a liquid-absorbent powder like the water-absorbent resin composition. However, the apparent contact angle can be measured by the below-mentioned method. The water-absorbent resin composition according to the present invention displays a contact angle of favorably not more than 45 degrees, more favorably not more than 30 degrees, particularly favorably not more than 20 degrees.

The water-absorbent resin composition (1) according to the present invention may possess such functions as given or enhanced by causing this composition to, besides the water-absorbent resin particles and the water-soluble polyvalent metal salt particles, further contain additives such as: water-insoluble finely-particulate inorganic powders (e.g. silicon dioxide, titanium dioxide, aluminum oxide, magnesium oxide, zinc oxide, talc, calcium phosphate, barium phosphate, silicic acid or its salts, clay, diatomite, zeolite, bentonite, kaolin, hydrotalcite, and salts (e.g. activated clay)); deodorants, perfumes, antibacterial agents, cationic polymer compounds (e.g. polyamines), foaming agents, pigments, dyes, manures, oxidizing agents, and reducing agents. The ratio of the additives as used is less than 10 mass %, favorably less than 5 mass %, more favorably less than 1 mass %, relative to the total of the water-absorbent resin particles and the water-soluble polyvalent metal salt particles.

[Process (1) for Production of Water-Absorbent Resin Composition]:

A favorable process for production of the composition (1) according to the present invention is a dry mixing process. The dry mixing process is a process in which the water-absorbent resin particles (favorably, surface-crosslinked ones) and the water-soluble polyvalent metal salt particles are mixed together in a state where the water-soluble polyvalent metal salt particles substantially keep their dry state. Hereupon, the water-soluble polyvalent metal salt particles are mixed under conditions where they can exist as independent particles.

When the water-absorbent resin composition (1) according to the present invention is produced or preserved, it must be avoided adding or mixing water in such an amount that the water-soluble polyvalent metal salt particles may dissolve, or putting the composition under high humidity. If the water-soluble polyvalent metal salt particles contact with the water-absorbent resin in a state dissolved in such as water, then the water-soluble polyvalent metal salt falls into a state coated to water-absorbent resin particle surfaces or permeated inside the resin to thus exist as particles no longer, so that the effects of the present invention are not sufficiently displayed. For example, in JP-A-523289/2001 (Kohyo) (WO 98/48857), there is disclosed a process for preparation of a super-water-absorbent polymer which process is characterized by including the steps of mixing a super-water-absorbent polymer with a polyvalent metal salt and then bringing the resultant mixture into close contact with a binder. Water or a water-soluble liquid is stated therein as the aforementioned binder. However, the present invention entirely differs from conventional processes in that, when the water-absorbent resin composition (1) according to the present invention is produced, an aqueous liquid (e.g. water, water-soluble liquid) does not need to be added after the mixing of the water-absorbent resin particles and the water-soluble polyvalent metal salt particles. Therefore, the water-soluble polyvalent metal salt particles which are contained in the water-absorbent resin composition (1) according to the present invention are not dissolved in a liquid, but exist substantially as dry particles along with the water-absorbent resin. It is an important method according to the present invention that the water-soluble polyvalent metal salt particles are caused to exist in a state of dry particles. Thereby there can be obtained the water-absorbent resin composition (1) which is excellent in water absorption performances such as after-damage liquid permeability.

The specific mixing method is free of especial limitation if it is a dry mixing method. For example, publicly known methods for addition and mixing of powders are used to carry out the addition in a lump or divisionally or continuously. The addition and mixing of the water-soluble polyvalent metal salt particles may be carried out while the water-absorbent resin particles are stirred. Or the stirring operation may be carried out after the addition of the water-soluble polyvalent metal salt particles. Usable as stirring apparatuses or mixing apparatuses are such as paddle blenders, ribbon mixers, rotary blenders, jar tumblers, plowshare mixers, cylinder type mixers, V-character-shaped mixers, ribbon type mixers, screw type mixers, twin-arm mixers, pulverizing type kneaders, channel type mixers, and plow type mixers.

The ratio between the water-soluble polyvalent metal salt particles and the water-absorbent resin particles as used is favorably in the range of 0.01 to 5 mass parts, more favorably 0.1 to 2 mass parts, per 100 mass parts of the solid content of the water-absorbent resin particles. In the case where the water-soluble polyvalent metal salt particles are added too much, the performance deterioration of the water-absorbent resin is brought about. In the case where the amount of the water-soluble polyvalent metal salt particles is too small, the water-soluble polyvalent metal salt particles do not take effect.

A more favorable mode of the dry mixing processes, which are favorable processes for production of the composition (1) according to the present invention, is a mode comprising the steps of:

adding a binder to water-absorbent resin particles obtained by polymerizing a monomer including acrylic acid and/or its salt; and then mixing the binder and the water-absorbent resin particles with water-soluble polyvalent metal salt particles.

Its feature is that: the binder is beforehand added to the water-absorbent resin particles to thus put them in a state where the binder is permeated across surfaces of the water-absorbent resin particles, and then they are mixed with the water-soluble polyvalent metal salt particles.

As to the modes as reported in JP-A-523287/2001 (Kohyo), JP-A-124879/1997 (Kokai), JP-A-270741/1988 (Kokai), and JP-A-538275/2002 (Kohyo) aforementioned as background arts, namely, as to the modes that a metal salt is formed into its aqueous solution and then added to a water-absorbent resin, there have been problems such that: the metal unfavorably goes so far as permeating into particles of the water-absorbent resin, so that there occur the following: the deterioration of the absorption capacity without load by influence of the metal inside the water-absorbent resin; and the deterioration of the absorption capacity under load, the gel-blocking, and the deteriorations of the liquid permeability and liquid diffusibility, due to insufficient presence of the metal on surfaces of the water-absorbent resin.

In addition, as to the modes as reported in JP-A-257235/1986 (Kokai) and JP-A-523289/2001 (Kohyo) aforementioned as background arts, namely, as to the modes that a water-absorbent resin is dry-blended with a metal salt and then water is added to them, there have been problems such that: the dissolved metal salt causes binding between particles to thus easily form a strong agglomerate and, in the case where this agglomerate is crushed by physical damage such as during the actual production or practical use, the absorption capacity under load is deteriorated. In addition, there have also been problems such that: the dissolved metal salt unfavorably goes so far as permeating into particles of the water-absorbent resin.

On the other hand, as to the above more favorable mode, because the water-soluble polyvalent metal salt particles being in a state of a powder is mixed with the water-absorbent resin particles in a state where the binder is permeated across surfaces of the water-absorbent resin particles, the permeation of the polyvalent metal into the water-absorbent resin particles can effectively be prevented, and further, the polyvalent metal is fixed all over the surfaces of the water-absorbent resin particles uniformly and moderately (i.e. in a state where the fixation is incomplete, but is not so weak as to enable free migration). Thereby consequently, the gel-blocking can sufficiently be prevented, and therefore excellent liquid permeability and liquid diffusibility can be displayed and also excellent absorption performances can be displayed. Furthermore, the resultant water-absorbent resin composition comes into a state which is strong also against the physical damage such as during the actual production or practical use.

The binder usable in the present invention has a role as a binder for fixing the polyvalent metal to surfaces of the water-absorbent resin particles, and is beforehand added to the water-absorbent resin particles before the water-absorbent resin particles is mixed with the water-soluble polyvalent metal salt particles.

The binder usable in the present invention is free of especial limitation if it includes a material which can play the above role. However, for example, there can be cited those which include such as water, polyhydric alcohols, water-soluble polymers, thermoplastic resins, pressure-sensitive adhesives, and adhesives. Favorable are those which include water and/or polyhydric alcohols.

The binder usable in the present invention may contain the aforementioned surface-crosslinking agent. Particularly, as is mentioned below, if the binder is made to contain the surface-crosslinking agent in the case where not yet surface-crosslinked water-absorbent resin particles are used as the water-absorbent resin particles, then it becomes possible to carry out the surface-crosslinking treatment in the process for production of the water-absorbent resin composition (1).

The amount of the binder usable in the present invention is favorably in the range of 0.1 to 10 mass %, more favorably 0.1 to 5 mass %, still more favorably 0.2 to 3 mass %, relative to the solid content of the water-absorbent resin particles. In the case where the amount of the binder is smaller than 0.1 mass %, there is a possibility that the moderate fixation of the polyvalent metal cannot be realized. In the case where the amount of the binder is larger than 10 mass %, there is a possibility that the properties of the resultant water-absorbent resin composition (1) may be deteriorated.

The method for adding the binder to the water-absorbent resin particles is not especially limited. However, there is preferred a method which enables uniform addition of the binder to the water-absorbent resin particles to mix them together. For instance, it can be exemplified by such as a method in which the binder is spraywise or dropwise added directly to the water-absorbent resin particles to mix them together. Examples of apparatuses for the mixing include cylinder type mixers, V-character-shaped mixers, ribbon type mixers, screw type mixers, twin-arm mixers, pulverizing type kneaders, channel type mixers, and plow type mixers.

When the binder is added to the water-absorbent resin particles, it is favorable to beforehand adjust the temperature of the water-absorbent resin particles in the range of 40 to 100° C., more favorably 50 to 90° C., still more favorably 60 to 80° C. In the case of deviating from the above temperature ranges, it is difficult that the binder is uniformly added to the water-absorbent resin particles to mix them together.

In the above more favorable mode, either surface-crosslinked water-absorbent resin particles or not yet surface-crosslinked water-absorbent resin particles may be used as the water-absorbent resin particles. If the binder is made to contain the surface-crosslinking agent in the case where the not yet surface-crosslinked water-absorbent resin particles are used as the water-absorbent resin particles, then it becomes possible to carry out the surface-crosslinking treatment in the process for production of the water-absorbent resin composition (1).

In the above more favorable mode, the water-absorbent resin particles to which the binder has been added is mixed with the water-soluble polyvalent metal salt particles.

The method for mixing the water-absorbent resin particles with the water-soluble polyvalent metal salt particles is the same as the aforementioned.

In the process (1) according to the present invention for production of a water-absorbent resin composition, the stirring operation is not necessarily needed when the water-soluble polyvalent metal salt particles are added to the water-absorbent resin particles. After the water-soluble polyvalent metal salt particles have been added to the water-absorbent resin particles, the step in which physical energy such as impact works against water-absorbent resins (which step is usually included in processes for production of the water-absorbent resins) may be utilized still in a state of non-uniform mixing, thus carrying out the mixing.

A favorable mode for carrying out the present invention is a process which utilizes energy that works against the water-absorbent resin when, as often adopted in processes for production of water-absorbent resins, the water-absorbent resin particles (powder) are pneumatically transported. That is to say, if the water-soluble polyvalent metal salt particles are added in a step as carried out before the step of pneumatically transporting the water-absorbent resin powder and if thereafter the pneumatic transportation is carried out, then the water-absorbent resin composition which is excellent in such as absorption performances can be obtained without needing to be processed with any special mixer or pulverizer.

The pneumatic transportation of the water-absorbent resin particles (powder) in the process for production of the water-absorbent resin is usually carried out over a transportation distance of 10 to 200 m and at a transportation speed of 0.1 to 15 m/second. By passing through the pneumatic transportation step, the water-absorbent resin particles and the water-soluble polyvalent metal salt particles are pulverized and mixed together due to contact and collision between particles or due to collision of particles with walls of the transportation course, so that the water-absorbent resin composition according to the present invention can be obtained.

The energy which the water-absorbent resin particles and the water-soluble polyvalent metal salt particles undergo during the pneumatic transportation corresponds to energy which they undergo when being shaken with a paint shaker in a state where they are placed in a container together with glass beads. Therefore, the energy to be actually applied can be reproduced with the paint shaker in a laboratory (paint shaker test, which may hereinafter be abbreviated as PS). The paint shaker test (PS) is carried out as follows: a glass container of 6 cm in diameter and 11 cm in height is charged with 10 g of glass beads of 6 mm in diameter and 30 g of the water-absorbent resin composition, and then attached to a paint shaker (product No. 488, produced by Toyo Seiki Seisakusho K.K.), and then shaken at 800 cycles/min (CPM) for 30 minutes. The details of the apparatus are disclosed in JP-A-235378/1997 (Kokai). The energy which is applied to the water-absorbent resin particles and the water-soluble polyvalent metal salt particles is energy corresponding to the range of 5 to 60 minutes, preferably 5 to 30 minutes, as the duration of the aforementioned shaking with the paint shaker, and almost conforms to the aforementioned energy as applied during the pneumatic transportation. It is also possible to make design of the pneumatic transportation step, such as pneumatic transportation distance and pneumatic transportation speed, by changing the shaking duration of the PS in the above range to thus find out the optimum point for performances of the water-absorbent resin composition. In addition, it is also possible to determine the selection or amount of the water-soluble polyvalent metal salt particles being used, by carrying out a test of mixing the water-absorbent resin particles and the water-soluble polyvalent metal salt particles together for the shaking duration of the PS corresponding to energy of the already designed pneumatic transportation step. If such force is applied, a part of the water-soluble polyvalent metal salt particles as used in the present invention become extremely fine particles to come into a state where they adhere uniformly to water-absorbent resin particle surfaces.

That is to say, in a favorable process for production of the water-absorbent resin composition (1) according to the present invention, it is favorable that, for the water-absorbent resin particles, there are used the water-soluble polyvalent metal salt particles which are in itself so brittle as to be pulverized due to the above physical energy, such as being in the form of: a powder of crystals; or an agglomerate or agglomerated material of fine particles; so that a mixture in which fine particles of the water-soluble polyvalent metal salt particles adhere uniformly to the water-absorbent resin particles (powder) can be obtained even if no special pulverization apparatus is used.

[Water-Absorbent Resin Composition (2)]:

The water-absorbent resin composition (2) according to the present invention comprises water-absorbent resin particles and a metal compound, wherein the water-absorbent resin particles are obtained by polymerizing a monomer including acrylic acid and/or its salt, and wherein:

the metal compound is one or not fewer than two members selected from among alkaline metal salts and polyvalent metal salts (except polyvalent metal salts of organic acids having not fewer than 7 carbon atoms per molecule); and at least a part of the metal compound is fused to surfaces of the water-absorbent resin particles.

As to the metal compound as used in the present invention, taking it into consideration that the water-absorbent resin composition (2) according to the present invention is utilized as a water-absorbing agent for sanitary materials such as disposable diapers, then it is favorable to select a metal compound which does not color the water-absorbent resin composition (2) and which is low poisonous to human bodies.

The metal compound, as used in the present invention, is favorably one or not fewer than two members selected from among alkaline metal salts and polyvalent metal salts (except polyvalent metal salts of organic acids having not fewer than 7 carbon atoms per molecule). Because the polyvalent metal salts of organic acids having not fewer than 7 carbon atoms per molecule have such high hydrophobicity as to deteriorate the capillary suction force of the water-absorbent resin composition, such polyvalent metal salts are not used as the polyvalent metal salts in the present invention.

Favorable as the alkaline metal salts are salts of Li, Na, and K.

The polyvalent metal salts except the polyvalent metal salts of organic acids having not fewer than 7 carbon atoms per molecule are favorably those which contain one or not fewer than two polyvalent metals selected from among Be, Mg, Ca, Sc, Y, Ti, Zr, V, Nb, Cr, Mo, Mn, Fe, Ru, Co, Rh, Ni, Pd, Cu, Zn, Ga, Ge, and Al, and more favorably those which contain one or not fewer than two polyvalent metals selected from among Ca, Mg, Fe, Ti, Zr, Zn, and Al, and most favorably those which contain Al. In addition, the aforementioned water-soluble polyvalent metal salt particles may be used.

The metal compound, as used in the present invention, is favorably a metal compound having a melting point of not higher than 250° C. In addition, the melting point of the metal compound is favorably in the range of 30 to 250° C., more favorably 40 to 200° C., still more favorably 50 to 150° C., most favorably 60 to 100° C. In the case where the melting point is higher than 250° C., there is a possibility that, when the metal compound is fused to the water-absorbent resin particles, damage may be done thereto, thus resulting in failure to obtain the objective properties. In addition, in the case where the melting point is lower than 30° C., there is a possibility that the metal compound may unfavorably permeate the inside of the water-absorbent resin particles, thus resulting in failure to obtain the objective properties.

The metal compound, as used in the present invention, is favorably hydrophilic and/or water-soluble. Therefore, the polyvalent metal salts of organic acids having not fewer than 7 carbon atoms per molecule are unfavorable. In addition, in the case where the polyvalent metal salts of organic acids having not fewer than 7 carbon atoms per molecule are used, their hydrophobicity is too high, and therefore there is a possibility that they may cause such as deterioration of the surface tension of the water-absorbent resin particles, thus resulting in failure to obtain the objective properties. In the present invention, the water solubility refers to a compound of which not less than 1 g, favorably not less than 10 g, dissolves into 100 g of water at 25° C.

The metal compound, as used in the present invention, favorably has water of hydration in its molecule. The metal compound having the water of hydration is usually hydrophilic and easily takes effect when the water-absorbent resin composition (2) according to the present invention absorbs water.

The metal compound, as used in the present invention, is favorably a solid, more favorably a powder, at normal temperature. In the case where the metal compound is a powder, then, the finer its particle diameters are, the more easily it fuses with the water-absorbent resin particles. Therefore, its mass-average particle diameter (D50) is favorably not larger than 1,000 μm, more favorably not larger than 600 μm, still more favorably not larger than 300 μm, most favorably not larger than 150 μm.

Specific examples of the metal compound, as used in the present invention, include one or not fewer than two members selected from among alkaline metal salts and polyvalent metal salts having not more than 6 carbon atoms which are recorded as of Sep. 10, 2003 in a GMELIN file provided by Gmelin Institute Varrentrappstr. and/or a BEILSTEIN file provided by Beilstein Chemiedaten und Software GmbH (each of them is usable as a search file of STN INTERNATIONAL, and their agency in Japan is the Scientific Information Society of Japan). As favorable ones among them, there can be cited those which have melting points of not higher than 250° C. As more favorable ones among them, there can be cited one or not fewer than two members selected from among inorganic acid salts or salts of organic acids having not more than 6 carbon atoms per molecule, such as sulfates, nitrates, phosphates, halides, oxalates, and acetates. As still more favorable ones among them, there can be cited those which have water of hydration. Being exemplified more specifically, there are favorably used one or not fewer than two members selected from among $Al_2(SO_4)_3 \cdot 14\text{-}18H_2O$, $KAl(SO_4)_2 \cdot 12H_2O$, $(NH_4)Al(SO_4)_2 \cdot 12H_2O$, $NaAl(SO_4)_2 \cdot 12H_2O$, $AlCl_3 \cdot 6H_2O$, $Na_2B_4O_7 \cdot 5\text{-}10H_2O$, $FeSO_4 \cdot 7H_2O$, and $K_2SO_4 \cdot Fe_2(SO_4)_3 \cdot 24H_2O$. The most favorable is one or not fewer than two members selected from among $Al_2(SO_4)_3 \cdot 14\text{-}18H_2O$ and $KAl(SO_4)_2 \cdot 12H_2O$.

The water-absorbent resin composition (2) according to the present invention comprises the water-absorbent resin particles and the metal compound, and is usually particulate and can be used favorably as an absorbent material for sanitary materials for absorption of urine, menstrual blood, sweat, and other body fluids.

The water-absorbent resin composition (2), according to the present invention, is a water-absorbent resin composition which comprises the water-absorbent resin particles and the metal compound, wherein the water-absorbent resin particles are obtained by polymerizing a monomer including acrylic acid and/or its salt, and wherein: the metal compound is one or not fewer than two members selected from among alkaline metal salts and polyvalent metal salts having not more than 6 carbon atoms; and at least a part of the metal compound is fused to surfaces of the water-absorbent resin particles.

In the present invention, the term "fusion" refers to a state where at least a part of the metal compound is made to adhere strongly to surfaces of the water-absorbent resin particles in a melted state.

In the present invention, favorably, the water-absorbent resin particles are surface-crosslinked ones. In addition, more favorably, the water-absorbent resin particles are materials having been surface-crosslinked with a polyhydric alcohol. Even if a small amount of surface-treating agent remains on surfaces, the metal compound is not bound to surfaces of the water-absorbent resin particles merely by mixing the remaining-surface-treating-agent-containing water-absorbent resin particles and the metal compound together. Therefore, the remaining surface-treating agent is not usable as the binder.

The water-absorbent resin composition (2), according to the present invention, is favorably free from binder as used to bind the water-absorbent resin particles and the metal compound to each other. The binder has a possibility of causing the deteriorations of the surface tension, the capillary absorption capacity (CSF), and other properties. For obtaining the water-absorbent resin composition (2) according to the present invention, it is not necessary to bind the water-absorbent resin particles and the metal compound to each other with the binder. The fusion of the metal compound to surfaces of the water-absorbent resin particles can strongly bind them together. As the case may be, the use of the binder rather hinders the fusion of the metal compound to the water-absorbent resin particles.

In the water-absorbent resin composition (2) according to the present invention, favorably, at least a part of the aforementioned metal compound is fused in the form of coating a part of surfaces of the water-absorbent resin particles in a layered state. The layered state refers to a state where the aforementioned metal compound thinly coats surfaces of the water-absorbent resin particles. The fusion in the form of the coating in the layered state prevents the metal compound from permeating the inside of the water-absorbent resin particles and also increases the surface area, and therefore makes it possible to easily obtain the objective performances. In addition, a form such that the surfaces of the water-absorbent resin particles are all coated with the metal compound has a possibility of bringing about deterioration of properties. Therefore, it is favorable that the metal compound forms a discontinuous layer on surfaces of the water-absorbent resin particles. In addition, there is also preferred a form such that inter-particular binding between the aforementioned water-absorbent resin particles and the aforementioned metal compound is formed by the fusion. It may be possible to observe these states from photographs taken with such as electron microscopes.

The water-absorbent resin composition (2), according to the present invention, is in the form of particles having a mass-average particle diameter in the range of favorably 100 to 600 μm, more favorably 200 to 500 μm. In the case where the mass-average particle diameter is smaller than 100 μm, then there is a possibility that: the handling property may be bad, and also much dust may be contained, and the liquid permeability and the liquid diffusibility may be bad. In the case where the mass-average particle diameter is larger than 600 μm, then there is a possibility that damage nay be easily done, thus resulting in deterioration of properties.

As to the water-absorbent resin composition (2) according to the present invention, the logarithmic standard deviation ($\sigma\zeta$) of the particle diameter distribution is favorably in the range of 0.25 to 0.45, more favorably 0.27 to 0.47, still more favorably 0.30 to 0.40. The logarithmic standard deviation ($\sigma\zeta$) of the particle diameter distribution is a numerical value indicating the broadness of the particle diameter distribution. The smaller this value is, the narrower particle diameter distribution it shows. That is to say, in the case where the logarithmic standard deviation ($\sigma\zeta$) is more than 0.45, there is a possibility that the width of the particle diameter distribution may be too broad, thus resulting in bad handling property or in failure to obtain the objective properties. In the case where the logarithmic standard deviation ($\sigma\zeta$) is less than 0.25, there is a possibility that the productivity may greatly be deteriorated, thus resulting in failure to obtain the effects corresponding to the cost.

As to the water-absorbent resin composition (2) according to the present invention, because at least a part of the metal compound is fused to surfaces of the water-absorbent resin particles, segregation of the metal compound occurs little. As an index for knowing the tendency for this segregation to occur, there is a metal compound segregation index. Specifically, the metal compound segregation index of the water-absorbent resin composition (2) according to the present invention is favorably in the range of 0.0 to 2.0, more favorably 0.0 to 1.7, most favorably 0.0 to 1.5. The metal compound segregation index is determined by the below-mentioned method.

As to the water-absorbent resin composition (2) according to the present invention, when at least a part of the metal compound fuses to surfaces of the water-absorbent resin particles, fine particles also fuse as the case may be. Therefore, the dust prevention effect is high.

It has been found out by the present inventors that the water-absorbent resin composition (2) according to the present invention is, surprisingly, more excellent in the handling property during the moisture absorption when compared with other methods for adding the metal compound to the water-absorbent resin particles (e.g. dry mixing, aqueous solution addition, addition of a binder after dry mixing). In the case where the metal compound is fused to surfaces of the water-absorbent resin particles, the metal compound coats a part of surfaces of the water-absorbent resin particles, whereby the binding between the water-absorbent resin particles during the moisture absorption is inhibited, so that there is provided an effect of preventing the agglomeration between particles. This effect works more effectively by the fusion. For example, in the case where the metal compound is added in the form of an aqueous solution, the metal compound unfavorably permeates the inside of the particles, and it is therefore difficult to obtain the effect of preventing the agglomeration between particles. In addition, in the case of the dry mixing, the water-absorbent resin particles and the metal compound contact with each other at points, thus still resulting in failure to obtain so much effect as that in the case of the fusion.

As to the water-absorbent resin composition (2) according to the present invention, the blocking ratio (BR) when having been put at 25° C. and a relative humidity of 70% for 1 hour is favorably not more than 20%, more favorably not more than 10%, still more favorably not more than 5%.

The water-absorbent resin composition (2), according to the present invention, favorably displays an absorption capacity without load (CRC) in the range of 15 to 45 g/g, more favorably 20 to 37 g/g, still more favorably 24 to 32 g/g. In the case where the absorption capacity without load is low, there is a possibility that the efficiency may be bad on an occasion of the use for sanitary materials such as diapers. In the case where the absorption capacity without load is too high, there is a possibility that the performance deterioration may occur due to such as deterioration of gel strength.

The water-absorbent resin composition (2), according to the present invention, favorably displays an absorption capacity under load (AAP) of not less than 16 g/g, more favorably not less than 20 g/g, still more favorably not less than 24 g/g. In addition, it is desirable that the deterioration of the absorption capacity under load (AAP) of the water-absorbent resin composition (2), as compared with an absorption capacity under load (AAP) of the water-absorbent resin particles to which the metal compound has not yet been added, is small. The water-absorbent resin composition (2) favorably maintains an absorption capacity under load (AAP) of not less than 0.85 time, more favorably not less than 0.90 time, most favorably not less than 0.95 time, in comparison with the absorption capacity under load (AAP) of the water-absorbent resin particles.

The water-absorbent resin composition (2), according to the present invention, favorably displays a saline flow conductivity (SFC) of not less than 30 ($\times 10^{-7} \cdot cm^3 \cdot s \cdot g^{-1}$), more favorably not less than 50 ($\times 10^{-7} \cdot cm^3 \cdot s \cdot g^{-1}$), still more favorably not less than 80 ($\times 10^{-7} \cdot cm^3 \cdot s \cdot g^{-1}$), most favorably not less than 100 ($\times 10^{-7} \cdot cm^3 \cdot s \cdot g^{-1}$). The saline flow conductivity (SFC) is a numerical value indicating the liquid permeability and the liquid diffusibility. The higher this value is, the more excellent in the liquid permeability and the liquid diffusibility the water-absorbent resin composition is. The saline flow conductivity (SFC) depends on the content of the water-absorbent resin composition in the sanitary material. The higher content needs the higher value of the saline flow conductivity (SFC).

The water-absorbent resin composition (2), according to the present invention, favorably displays a capillary absorption capacity (CSF) of not less than 15 g/g, more favorably not less than 18 g/g, most favorably not less than 20 g/g, at a height of 20 cm. The capillary absorption capacity (CSF) is a value indicating the strength of the capillary suction force. The higher capillary absorption capacity (CSF) can more diffuse an absorbed liquid also in a height direction and is therefore more desirable.

As the water-absorbent resin composition (2) according to the present invention, there are used those of which the water-extractable component content is favorably not higher than 20 mass %, more favorably not higher than 15 mass %, most favorably not higher than 10 mass %. In the case where the water-extractable component content is higher than 20 mass % in the present invention, there is a possibility not only that no effects of the present invention may be obtained, but also that the performance may be deteriorated in the use for water-absorbent structures for sanitary materials such as diapers. In addition, such a water-extractable component content is unfavorable also from the viewpoint of safety. As a cause of the performance deterioration, it can be cited that, when the water-absorbent resin composition absorbs water to swell, a high-molecular component elutes from the inside of the water-absorbent resin to thereby hinder the liquid permeation. The eluted high-molecular component can be considered to resist when a liquid flows across surfaces of water-absorbent resin particles. In addition, similarly, the elution of the high-molecular component has a possibility of increasing the viscosity of an absorbed solution to thus deteriorate the capillary suction force. The water-extractable component content of the water-absorbent resin composition is measured by the below-mentioned method.

Although not especially limited, the water content of the water-absorbent resin composition (2) according to the present invention is favorably in the range of 0 to 100 mass %, more favorably 0.01 to 40 mass %, still more favorably 0.1 to 10 mass %.

Although not especially limited, the bulk density of the water-absorbent resin composition (2) according to the present invention is favorably in the range of 0.40 to 0.90 g/ml, more favorably 0.50 to 0.80 g/ml (the method for measuring the bulk density is specified in JIS K-3362). In the case of water-absorbent resin compositions which have a bulk density of less than 0.40 g/ml or more than 0.90 g/ml, there is a possibility that they may be damaged easily by the process and may accordingly be deteriorated in property.

The water-absorbent resin composition (2) according to the present invention may possess such functions as given or enhanced by causing this composition to, besides the water-absorbent resin particles and the metal compound, further contain additives such as: water-insoluble finely-particulate inorganic powders (e.g. silicon dioxide, titanium dioxide, aluminum oxide, magnesium oxide, zinc oxide, talc, boric acid, silicic acid, clay, diatomite, zeolite, bentonite, kaolin, hydrotalcite, and salts (e.g. activated clay)); deodorants, perfumes, antibacterial agents, cationic polymer compounds (e.g. polyamines), foaming agents, pigments, dyes, manures, oxidizing agents, and reducing agents. The ratio of the additives as used is favorably less than 10 mass %, more favorably less than 5 mass %, still more favorably less than 1 mass %, relative to the mass of the water-absorbent resin composition.

In the case where the water-absorbent resin composition (2) according to the present invention is used for the sanitary materials, if the metal compound is fused to the surface-crosslinked water-absorbent resin particles, then the wettability to aqueous liquids is good, and further, a liquid-absorbed gel little causes what is called gel-blocking, and spaces between gel particles are not clogged up due to close cohesion of the gel, either. Therefore, even in the case where the water-absorbent resin composition is used in a high concentration in absorbent structures such as diapers, it is possible that, at the second time or thereafter, urine or body fluids diffuse into the absorbent structures, without losing a place to go on surfaces of the absorbent structures, so that the urine or body fluids can be distributed to the inside water-absorbent resin particles. Furthermore, a mixture of the water-absorbent resin of the water-absorbent resin composition and an agglomerated material of this water-absorbent resin composition has spaces of the appropriate size between particles and therefore combines a property of sucking a liquid by the capillary force and therefore can diffuse an absorbed liquid into the entire absorbent structure also by the capillary suction force.

[Process (2) for Production of Water-Absorbent Resin Composition]:

The water-absorbent resin particles and the metal compound, which are used for the production of the water-absorbent resin composition (2) according to the present invention, are as previously explained.

The process for production of the water-absorbent resin composition (2) according to the present invention is a process comprising the steps of: heating the water-absorbent resin particles and/or the metal compound to a temperature of not lower than the melting point of the metal compound; and thereby fusing at least a part of the metal compound to surfaces of the water-absorbent resin particles; wherein the water-absorbent resin particles are obtained by polymerizing a monomer including acrylic acid and/or its salt.

In the present invention, the term "fusion" refers to a phenomenon such that at least a part of the metal compound melts by heat or becomes softer by heat than its solid state, thus adhering to another substance, and the term "fusion" is used in the same meaning as heat-fusion. However, there is also included a case where the metal compound is fused by melting it or making it softer than its solid state, by means other than heat.

That is to say, when it comes to the above process, there is no especial limitation. However, for example, there are the following processes (a) to (d):

(a) A process in which the water-absorbent resin particles, which have been heated to not lower than the melting point of the metal compound, and the metal compound are mixed together.

(b) A process in which the metal compound, which has been heated to not lower than the melting point of the metal compound, and the water-absorbent resin particles are mixed together.

(c) A process in which the water-absorbent resin particles and the metal compound are mixed together, and then the resultant mixture is heated to not lower than the melting point of the metal compound.

(d) A process in which the water-absorbent resin particles, which have been heated to not lower than the melting point of the metal compound, and the metal compound, which has been heated to not lower than the melting point of the metal compound, are mixed together.

These processes are favorable, but other processes may be used.

In the present invention, examples of means of heating the water-absorbent resin particles and/or the metal compound include heaters, microwaves, ultrasonic waves, and far infrared rays.

In the present invention, favorably, the water-absorbent resin particles are materials having been surface-crosslink-treated with a compound having at least two functional groups which make a dehydration reaction or transesterification reaction with a carboxyl group.

In the present invention, the metal compound is used favorably in the form of not such as an aqueous dispersion or solution, but a powder. However, the metal compound may be used in a melted state without adding such as water thereto.

In the present invention, the metal compound is used favorably in an amount of 0.001 to 10 mass %, more favorably 0.01 to 5 mass %, most favorably 0.1 to 3 mass %, relative to the mass of the water-absorbent resin particles. In the case where the amount of the metal compound being added is smaller than 0.001 mass %, it is difficult to obtain the effects of the present invention. Also, in the case of the addition amount larger than 10 mass %, not only are there economical disadvantages, but also there is a possibility that the performance deterioration of the water-absorbent resin composition may be brought about.

In the present invention, there is no especial limitation on the adding and mixing method. Publicly known methods for addition and mixing of powders may be used. In a favorable method, a predetermined amount of metal compound is added to the water-absorbent resin particles in a lump or divisionally or continuously.

In the present invention, favorably, the mixing of the water-absorbent resin particles and the metal compound is carried out under stirring. Also favorably under stirring, at least a part of the metal compound is fused to surfaces of the water-absorbent resin particles. Usable as stirring apparatuses are such as paddle blenders, ribbon mixers, rotary blenders, jar tumblers, plowshare mixers, and mortar mixers. These stirring apparatuses may be heatable apparatuses or may be apparatuses which cools the heated mixture.

In the present invention, when the water-absorbent resin particles and/or the metal compound is heated, the water-absorbent resin particles and/or the metal compound needs to be heated to not lower than the melting point of the metal compound. The temperature range to which the heating is carried out is favorably not higher than 250° C., more favorably the range of 30 to 250° C., most favorably 50 to 200° C. In addition, a state where the metal compound does not entirely melt is favorable. In the case where the metal compound has entirely melted, there is a possibility that the water-absorbent resin particles may be coated entirely with the metal compound, thus resulting in deterioration of properties.

In the present invention, the stirring duration of the water-absorbent resin particles and the metal compound is not especially limited. However, it is favorably not more than 60 minutes, more favorably not more than 30 minutes.

In the present invention, when at least a part of the metal compound is fused to surfaces of the water-absorbent resin particles, it is favorable to give pressure to a mixture of the water-absorbent resin particles and the metal compound. This pressurization promotes the fusion.

In the present invention, after at least a part of the metal compound has been fused to surfaces of the water-absorbent resin particles, it is favorable to regulate the particle diameter distribution of the resultant water-absorbent resin composition. As means for regulating the particle diameter distribution, it is enough to use publicly known means. However, a disintegrator and/or a classifier is favorably used.

In the present invention, when the water-absorbent resin particles and the metal compound are mixed together, addition of water and mixing of the metal compound in an aqueous solution state must be avoided. In the case where the addition of water or the mixing of the metal compound in an aqueous solution state is made, the metal compound component unfavorably permeates the inside of the water-absorbent resin particles, thus resulting in failure to sufficiently display the effects of the present invention. For example, in JP-A-523289/2001 (Kohyo) (WO 98/48857), there is disclosed a process for preparation of a super-water-absorbent polymer which process is characterized by including the steps of mixing a super-water-absorbent polymer with a polyvalent metal salt and then bringing the resultant mixture into close contact with a binder. Water or a water-soluble liquid is stated therein as the aforementioned binder. On the other hand, the present invention entirely differs from conventional processes in that, when the water-absorbent resin composition (2) according to the present invention is produced, an aqueous liquid (e.g. water, water-soluble liquid) does not need to be added after the mixing of the water-absorbent resin particles and the metal compound. Therefore, in the present invention, methods without using any binder are favorable. The use of the binder has a possibility of deteriorating the surface tension, the CSF, and other properties. In addition, as an example of methods without using the water or the water-soluble liquid, there can be considered a method in which the water-absorbent resin particles and the metal compound are mixed together in a dry manner. However, this method has a possibility of causing such as segregation or increase of dust. In addition, there are problems such that: even if the metal compound adheres to the water-absorbent resin particles, its binding force is so weak that the metal compound is unfavorably easily released merely by application of a little force. In the present invention, it is an important method to fuse at least a part of the metal compound to surfaces of the water-absorbent resin particles. By this method, it is possible to provide the water-absorbent resin composition which solves the aforementioned prior problems, and involves little segregation of the additive, and is excellent in the liquid permeability and the liquid diffusibility, and also, undergoes little deterioration of the absorption capacity under load, and further, surprisingly, is excellent also in the handling property during the moisture absorption, and further has a dust prevention effect.

[Water-Absorbent Structure]:

The water-absorbent resin composition (1) and/or (2), according to the present invention, can be combined with an appropriate material and thereby formed into the water-absorbent structure which is, for example, favorable as an absorbent layer for sanitary materials. Hereinafter, a description is made about the water-absorbent structure in the present invention.

The water-absorbent structure in the present invention refers to a molded composition which comprises a water-absorbent resin composition and another material and is used for sanitary materials (e.g. disposable diapers, sanitary napkins, incontinent pads, and medical pads) for absorption of such as blood, body fluids, and urine. Examples of the above other material include cellulose fibers. Specific examples of the cellulose fibers include: wood pulp fibers from wood, such as mechanical pulp, chemical pulp, semichemical pulp, and dissolving pulp; and synthetic cellulose fibers, such as rayon and acetate. Favorable cellulose fibers are the wood pulp fibers. These cellulose fibers may partially contain synthetic fibers such as nylon and polyester. When the water-absorbent resin composition (1) and/or (2) according to the present invention is used as a portion of the water-absorbent structure, the mass of the water-absorbent resin composition (1) and/or (2) according to the present invention as contained in the water-absorbent structure is favorably in the range of not smaller than 20 mass %. In the case where the mass of the water-absorbent resin composition (1) and/or (2) according to the present invention as contained in the water-absorbent structure is smaller than 20 mass %, there is a possibility that no sufficient effects can be obtained.

For the purpose of obtaining the water-absorbent structure from the water-absorbent resin composition (1) and/or (2) according to the present invention and the cellulose fibers, for example, publicly known means for obtaining water-absorbent structures can appropriate be selected from among such as: a method in which the water-absorbent resin composition (1) and/or (2) is spread onto paper or mat made of such as the cellulose fibers and is, if necessary, interposed therebetween; and a method in which the cellulose fibers and the water-absorbent resin composition (1) and/or (2) are uniformly blended together. A favorable method is a method in which the water-absorbent resin composition (1) and/or (2) and the cellulose fibers are mixed together in a dry manner and then compressed. This method can greatly prevent the water-absorbent resin composition (1) and/or (2) from falling off from the cellulose fibers. The compression is favorably carried out under heating, and its temperature range is, for example, the range of 50 to 200° C. In addition, for the purpose of obtaining the water-absorbent structure, methods as disclosed in JP-A-509591/1997 (Kohyo) and JP-A-290000/1997 (Kokai) are also favorably used.

In the case where used for water-absorbent structures, the water-absorbent resin composition (1) and/or (2) according to the present invention is so excellent in the properties as to give water-absorbent structures which are very excellent in that they quickly take liquids in and further in that the amount of the liquids remaining on their surface layers is small.

Because the water-absorbent resin compositions (1) and (2) according to the present invention have excellent water absorption properties, these water-absorbent resin compositions can be used as water-absorbing and water-retaining agents for various purposes. For example, these water-absorbent resin compositions can be used for such as: water-absorbing and water-retaining agents for absorbent articles (e.g. disposable diapers, sanitary napkins, incontinent pads, and medical pads); agricultural and horticultural water-retaining agents (e.g. substitutes for peat moss, soil-modifying-and-improving agents, water-retaining agents, and agents for duration of effects of agricultural chemicals); water-retaining agents for buildings (e.g. dew-condensation-preventing agents for interior wall materials, cement additives); release control agents; coldness-retaining agents; disposable portable body warmers; sludge-solidifying agents; freshness-retaining agents for foods; ion-exchange column materials; dehydrating agents for sludge or oil; desiccating agents; and humidity-adjusting materials. In addition, the water-absorbent resin compositions (1) and (2) according to the present invention can be used particularly favorably for sanitary materials for absorption of excrement, urine, or blood, such as disposable diapers and sanitary napkins.

In the case where the water-absorbent structure in the present invention is used for sanitary materials (e.g. disposable diapers, sanitary napkins, incontinent pads, and medical pads), this water-absorbent structure is used favorably with a constitution including: (a) a liquid-permeable top sheet placed so as to be adjacent to a wearer's body; (b) a liquid-impermeable back sheet placed so as to be adjacent to the wearer's clothes at a distance from the wearer's body; and (c) the water-absorbent structure placed between the top sheet and the back sheet. The water-absorbent structure may be in more than one layer or used along with such as a pulp layer.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to them. Hereinafter, for convenience, the units "mass part(s)" and "liter(s)" may be referred to simply as "part(s)" and "L" respectively. In addition, the unit "mass %" may be referred to as "wt %".

The measurement and evaluation methods in the Examples and the Comparative Examples are shown below.

Unless otherwise noted, the following measurement is stated as having been carried out under conditions of a room temperature (25° C.) and a humidity of 50 RH %.

Incidentally, in cases of water-absorbent resin compositions having been used for end products such as sanitary materials, the water-absorbent resin compositions have already absorbed moisture. Therefore, the measurement may be carried out after appropriately separating the water-absorbent resin compositions from the end products and then drying the separated water-absorbent resin compositions under a reduced pressure at a low temperature (e.g. under not higher than 1 mmHg at 60° C. for 12 hours). In addition, all the water-absorbent resin compositions as used in the Examples and Comparative Examples of the present invention had water contents of not higher than 6 mass %.

<Absorption Capacity Without Load (CRC)>:

An amount of 0.20 g of water-absorbent resin or water-absorbent resin composition was weighed out precisely to a level of 0.0001 g, and then uniformly placed and sealed into a bag (85 mm×60 mm or 60 mm×60 mm) made of nonwoven fabric (trade name: Heatron Paper, type: GSP-22, produced by Nangoku Pulp Kogyo Co., Ltd.).

A container of 1 L was charged with 1 L of 0.9 mass % aqueous sodium chloride solution (physiological saline solution), in which one evaluation sample per one container was then immersed for 1 hour. Incidentally, because the present invention is an invention made by directing attention to effects of ion migration, more than one sample per one container must not be immersed.

After 1 hour, the bag was pulled up and then drained of water by centrifugal force of 250 G with a centrifugal separator (produced by Kokusan Co., Ltd., centrifugal separator: model H-122) for 3 minutes, and then the mass W1 (g) of the bag was measured. In addition, the same procedure as the above was carried out without the water-absorbent resin or water-absorbent resin composition, and the resultant mass W0 (g) was measured. Then, the absorption capacity (g/g) without load was calculated from these W1 and W0 in accordance with the following equation:

$$CRC(g/g) = [(W1(g) - W0(g))/\text{mass } (g) \text{ of water-absorbent resin or water-absorbent resin composition}] - 1$$

<Absorption Capacity Under Load (AAP)>:

The AAP was measured by the following method A or B. The AAP may be measured by either of these methods, and the measured value is little influenced by the measurement method.

As to the AAP in the below-mentioned Referential Examples, Examples, and Comparative Examples, the AAP as shown in Table 1 is AAP as measured by the method A, and the other AAP is AAP as measured by the method B.

(Method A):

The absorption capacity under a load (AAP) was measured with an apparatus of FIG. 1.

There was prepared a load 21 as adjusted so as to give a pressure of 4.83 kPa (0.7 psi). Onto a metal gauze 18 of 400 meshes (mesh opening size of 38 μm) of a plastic cylinder 19 of 60 mm in diameter with the metal gauze stuck on its bottom, there was dispersed about 0.90 g (Wp2) of water-absorbent resin composition or water-absorbent resin, and further thereon the above load 21 (in the case of 0.7 psi) was put to prepare a liquid absorption instrument, which was then put on a filter paper 17 on a glass filter 13 of FIG. 1. After 60 minutes, there was measured a value (Wc) of the physiological saline solution (0.90 mass % aqueous NaCl solution) as absorbed by the water-absorbent resin composition or water-absorbent resin. The absorption capacity under the load was determined using the following equation.

$$AAP(g/g)=Wc/Wp2$$

Figure 2:
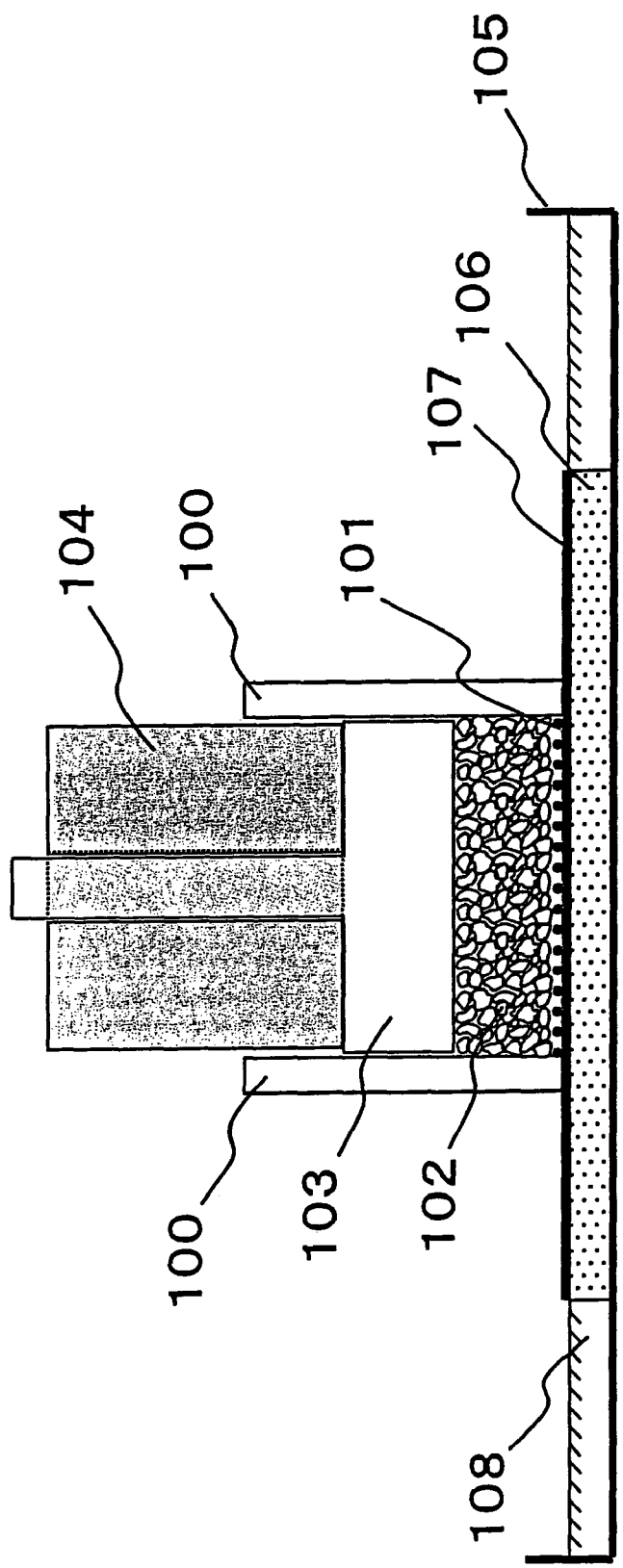
FIG. 2 is a schematic sectional view of a measurement apparatus as used for measuring the AAP (method B).

(Method B):

The measurement was carried out with an apparatus as shown in FIG. 2.

A stainless metal gauze 101, which was a screen of 400 meshes (mesh opening size: 38 μm), was attached by fusion to a bottom of a plastic supporting cylinder 100 having an inner diameter of 60 mm. Then, under conditions of a room temperature (20 to 25° C.) and a humidity of 50 RH %, onto the above metal gauze, there was uniformly spread 0.90 g of water-absorbent resin or water-absorbent resin composition 102, and further thereon, there were mounted a piston 103 and a load 104 in sequence, wherein the piston had an outer diameter of only a little smaller than 60 mm and made no gap with the inner wall surface of the supporting cylinder, but was not hindered from moving up and down, and wherein the piston and the load were adjusted so that a load of 4.83 kPa (0.7 psi) could uniformly be applied to the water-absorbent resin or water-absorbent resin composition. Then, the mass Wa (g) of the resultant one set of measurement apparatus was measured.

A glass filter plate 106 having a diameter of 90 mm (produced by Sogo Rikagaku Glass Seisakusho Co., Ltd., pore diameter: 100 to 120 μm) was mounted inside a Petri dish 105 having a diameter of 150 mm, and then a 0.90 mass % aqueous sodium chloride solution (physiological saline solution) 108 (20 to 25° C.) was added up to the same level as the top surface of the glass filter plate, on which a filter paper 107 having a diameter of 90 mm (produced by ADVANTEC Toyo Co., Ltd., trade name: (JIS P 3801, No. 2), thickness: 0.26 mm, diameter of captured particles: 5 μm) was then mounted so that its entire surface would be wetted, and further, an excess of liquid was removed.

The one set of measurement apparatus was mounted on the above wet filter paper, thereby getting the liquid absorbed under the load for a predetermined duration. This absorption duration was defined as 1 hour from the start of the measurement. Specifically, 1 hour later, the one set of measurement apparatus was removed by being lifted to measure its mass Wb (g). This measurement of the mass must be carried out as quickly as possible and so as not to give any vibration. Then, the absorption capacity under load (AAP) (g/g) was calculated from the Wa and Wb in accordance with the following equation:

$$AAP(g/g)=[Wb(g)-Wa(g)]/\text{mass }(g)\text{ of water-absorbent resin or water-absorbent resin composition}$$

<Saline Flow Conductivity (SFC)>:

The following test was carried out according to the saline flow conductivity (SFC) test as described in JP-A-509591/1997 (Kohyo).

Figure 3:
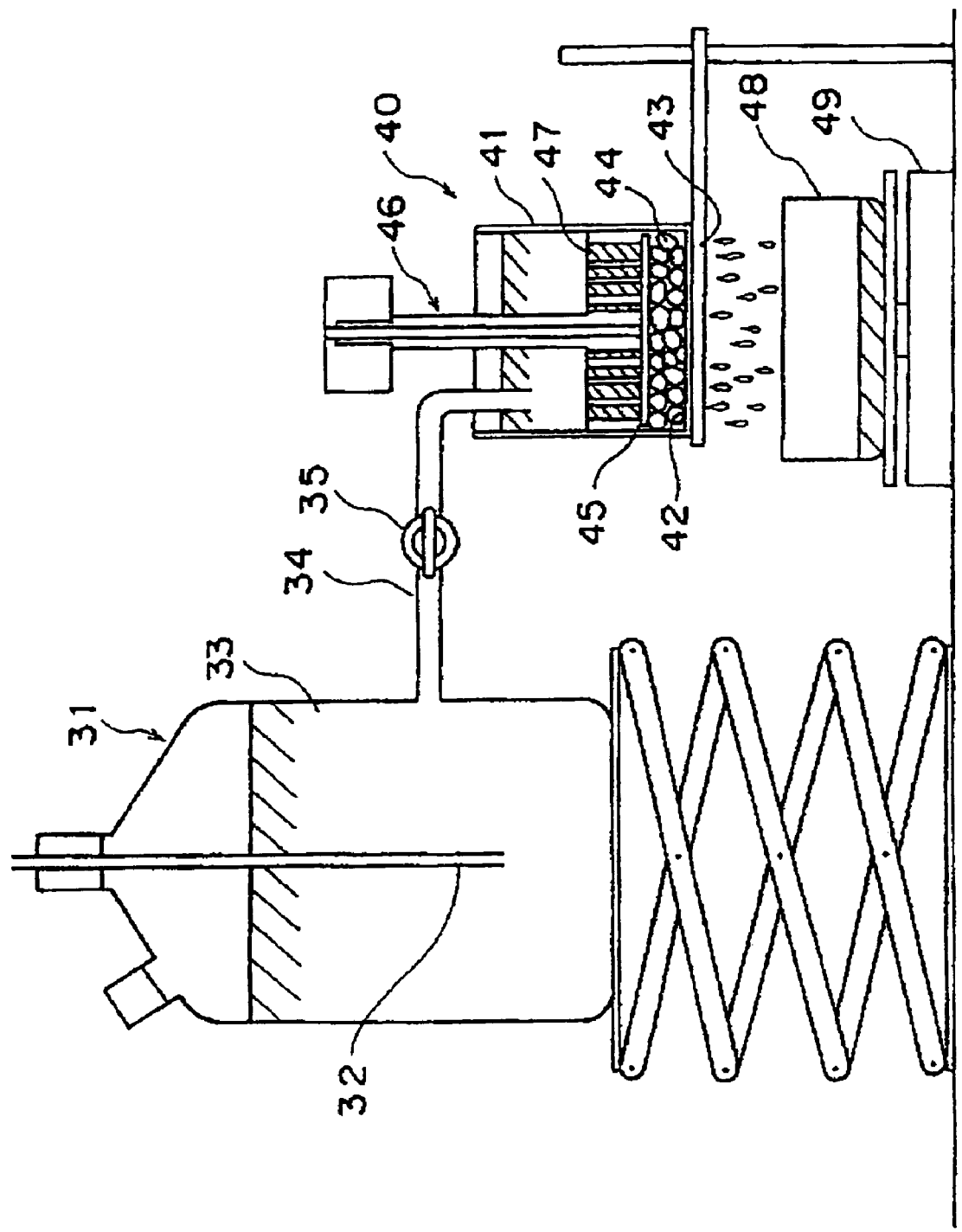
FIG. 3 is a schematic sectional view of a measurement apparatus as used for measuring the SFC.

An apparatus as shown in FIG. 3 was used, and a water-absorbent resin or water-absorbent resin composition (0.900 g) as uniformly placed in a receptacle 40 was swollen in synthetic urine (1) under a load of 0.3 psi (2.07 kPa) for 60 minutes (which was 120 minutes in the case of measuring the retention ratio of the saline flow conductivity (SFC)), and the gel layer height of the resultant gel 44 was recorded. Next, under the load of 0.3 psi (2.07 kPa), a 0.69 mass % aqueous sodium chloride solution 33 was passed through the swollen gel layer from a tank 31 under a constant hydrostatic pressure. This SFC test was carried out at room temperature (20 to 25° C.). The amount of the liquid passing through the gel layer was recorded as a function to time with a computer and a balance at twenty seconds' intervals for 10 minutes. The rate $F_s(t)$ of the flow passing through the swollen gel 44 (mainly between particles thereof) was determined in a unit of g/s by dividing the incremental mass (g) by the incremental time (s). The time when the constant hydrostatic pressure and the stable flow rate are obtained was represented by $t_s$, and only the data as obtained between $t_s$ and 10 minutes were used for the flow rate calculation. The $F_s(t=0)$ value, namely, the initial rate of the flow passing through the gel layer, was calculated from the flow rates as obtained between $t_s$ and 10 minutes. The $F_s(t=0)$ was calculated by extrapolating the results of a least-squares fit of $F_s(t)$ versus time to t=0.

$$SFC=(F_s(t=0)\times L_0)/(\rho\times A\times\Delta P)$$

$$=(F_s(t=0)\times L_0)/139{,}506$$

where:
$F_s(t=0)$: flow rate denoted by g/s;
$L_0$: initial thickness of gel layer denoted by cm;
$\rho$: density of NaCl solution (1.003 g/cm$^3$);
A: area of top of gel layer in cell 41 (28.27 cm$^2$);
$\Delta P$: hydrostatic pressure applied to gel layer (4,920 dyne/cm$^2$); and
the unit of the SFC is: $(\times 10^{-7}\cdot\text{cm}^3\cdot\text{s}\cdot\text{g}^{-1})$.

As to the apparatus as shown in FIG. 3, a glass tube 32 was inserted in the tank 31, and the lower end of the glass tube 32 was placed so that the 0.69 mass % aqueous sodium chloride solution 33 could be maintained at a height of 5 cm from the bottom of the swollen gel 44 in the cell 41. The 0.69 mass % aqueous sodium chloride solution 33 in the tank 31 was supplied to the cell 41 through an L-tube 34 having a cock. A receptacle 48 to collect the passed liquid was placed under the cell 41, and this collecting receptacle 48 was set on a balance 49. The inner diameter of the cell 41 was 6 cm, and a No. 400 stainless metal gauze (mesh opening size: 38 μm) 42 was set at the bottom thereof. Holes 47 sufficient for the liquid to pass through were opened in the lower portion of a piston 46, and its bottom portion was equipped with a well-permeable glass filter 45 so that the water-absorbent resin or water-absorbent resin composition or their swollen gels would not enter the holes 47. The cell 41 was placed on a stand to put the cell thereon. The face, contacting with the cell, of the stand was set on a stainless metal gauze 43 that did not inhibit the liquid permeation.

The synthetic urine (1) as used was obtained by mixing together the following: 0.25 g of calcium chloride dihydrate; 2.0 g of potassium chloride; 0.50 g of magnesium chloride hexahydrate; 2.0 g of sodium sulfate; 0.85 g of ammonium dihydrogenphosphate; 0.15 g of diammonium hydrogenphosphate; and 994.25 g of pure water.

<Saline Flow Conductivity (SFC) after Paint Shaker Test (SFC after PS)>:

The following measurement was carried out on the basis of the apparatus as disclosed in JP-A-235378/1997 (Kokai).

A glass bottle of 6 cm in diameter and 11 cm in height having a lid was charged with 30 g of water-absorbent resin or water-absorbent resin composition and about 10 g of glass beads (diameter: 6 mm), and then attached to a TOYOSEIKI PAINT SHAKER (for 100 V, 60 HZ), and then shaken for 30 minutes. The glass beads and the water-absorbent resin or water-absorbent resin composition were sieved with a metal gauze having a mesh opening size of about 2 mm, thus obtaining a water-absorbent resin or water-absorbent resin composition after the paint shaker test.

The saline flow conductivity of the obtained water-absorbent resin or water-absorbent resin composition was measured by the aforementioned method.

Incidentally, the CRC and AAP after PS can also be measured by the same method.

<Mass-Average Particle Diameter (D50) and Logarithmic Standard Deviation (σζ) of Particle Diameter Distribution>:

Water-absorbent resins or water-soluble polyvalent metal salt particles or water-absorbent resin compositions were classified with JIS standard sieves having mesh opening sizes of such as 850 µm, 710 µm, 600 µm, 500 µm, 425 µm, 300 µm, 212 µm, 150 µm, and 45 µm. Then, the percentages R of the residues on these sieves were plotted on a logarithmic probability paper. Therefrom, a particle diameter corresponding to R=50 mass % was read as the mass-average particle diameter (D50). In addition, the logarithmic standard deviation (σζ) of the particle diameter distribution is shown by the following equation. The smaller σζ value shows the narrower particle diameter distribution.

$$\sigma\zeta = 0.5 \times \ln(X2/X1)$$

(wherein: X1 is a particle diameter when R=84.1 mass %, and X2 is a particle diameter when R=15.9 mass %)

As to the classification method for measuring the mass-average particle diameter (D50) and the logarithmic standard deviation (σζ) of the particle diameter distribution, 10.0 g of water-absorbent resin or water-soluble polyvalent metal salt particles or water-absorbent resin composition was placed onto JIS standard sieves (having mesh opening sizes of 850 µm, 710 µm, 600 µm, 500 µm, 425 µm, 300 µm, 212 µm, 150 µm, and 45 µm) (THE IIDA TESTING SIEVE: diameter=8 cm) under conditions of a room temperature (20 to 25° C.) and a humidity of 50 RH %, and then classified with a shaking classifier (IIDA SIEVE SHAKER, TYPE: ES-65 type, SER. No. 0501) for 5 minutes.

<Dust Generation Degree>:

The water-absorbent resin or water-absorbent resin composition was placed into a PE bag (No. 13) as beforehand coated with an antistatic agent. This bag was shaken 30 times and then opened to carry out the measurement with DIGITAL DUST INDICATOR P-5L (produced by SHIBATA) for 1 minute. This measurement was carried out 10 times, and its average value was determined.

<Capillary Absorption Capacity (CSF)>:

The CSF is an index showing the capillary suction force of the water-absorbent resin or water-absorbent resin composition.

The capillary absorption capacity is determined by measuring the ability of the absorbent structure to absorb a liquid against a negative pressure gradient of the water column of 20 cm under a load of 0.06 psi within a predetermined time.

Figure 4:
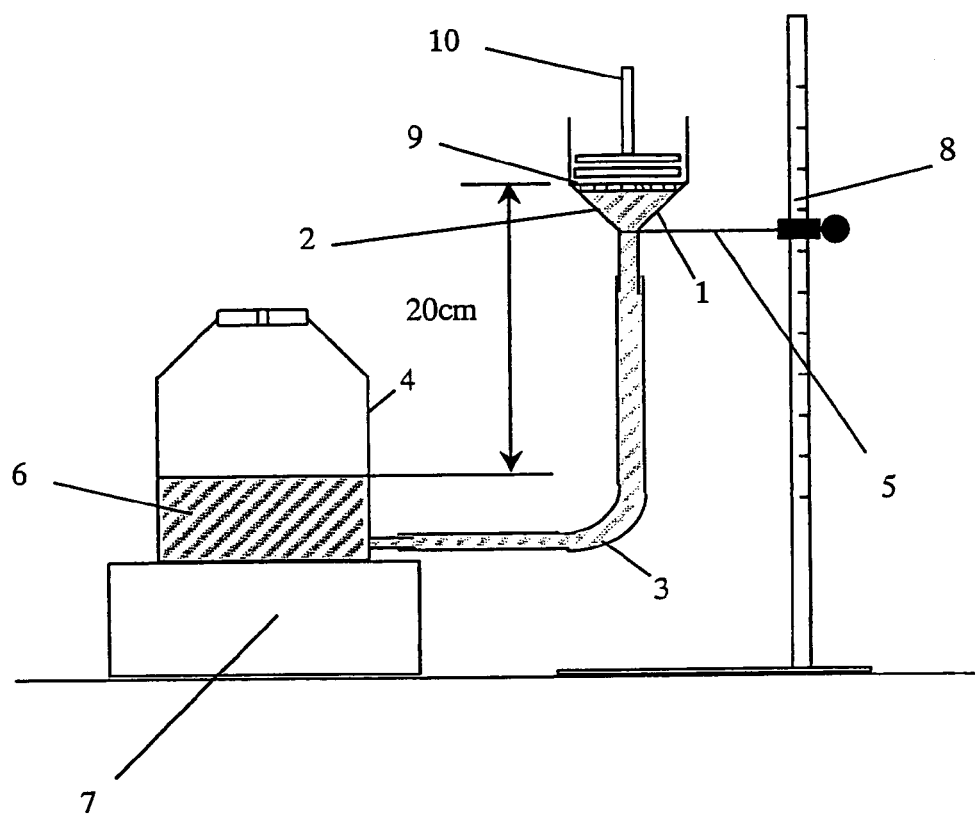
FIG. 4 is a schematic sectional view of a measurement apparatus as used for measuring the CSF.

While referring to FIG. 4, an apparatus and method for measuring the capillary absorption capacity are described.

A conduit 3 was connected to a lower portion of a glass filter 2 of 60 mm in diameter having a liquid-absorbing surface of a porous glass plate 1 (glass filter particle No. #3: Buchner type filter TOP 17G-3 (code no. 1175-03) produced by Sogo Rikagaku Glass Seisakusho Co., Ltd.), and this conduit 3 was connected to an opening as provided to a lower portion of a liquid storage container 4 of 10 cm in diameter. The porous glass plate of the aforementioned glass filter has an average pore diameter of 20 to 30 µm, and can retain water in the porous glass plate by its capillary force against the negative pressure of the water column even in a state where a difference of 60 cm between heights of liquid surfaces is made, so that a state of no introduction of air can be kept. A supporting ring 5 was fitted to the glass filter 2 in order to let up and down its height, and the system was filled with a 0.90 mass % physiological saline solution (0.90 mass % aqueous NaCl solution) (0.90% NaCl solution) 6, and the liquid storage container was put on a balance 7. After it had been confirmed that there was no air in the conduit and under the porous glass plate of the glass filter, the difference in height between a liquid surface level of the top of the physiological saline solution (0.90 mass % aqueous NaCl solution) 6 in the liquid storage container 4 and a level of the upside of the porous glass plate 1 was adjusted to 20 cm, and then the glass filter was fixed to a stand 8.

An amount of 0.44 g of specimen to be measured 9 (water-absorbent resin composition) was quickly dispersed uniformly onto the glass filter (porous glass plate 1) in the funnel, and further thereon a load 10 (0.06 psi) having a diameter of 59 mm was put, and then, 30 minutes later, there was measured a value (W20) of the 0.90 mass % physiological saline solution (0.90 mass % aqueous NaCl solution) as absorbed by the specimen to be measured 9.

The capillary absorption capacity is determined from the following equation.

Capillary absorption capacity (CSF) (g/g)=absorption amount ($W20$) (g)/0.44 (g)

<Retention Ratio of Saline Flow Conductivity (SFC) (Retention Ratio of SFC)>:

In the aforementioned method for measurement of the saline flow conductivity (SFC), the swelling time under the load of 0.3 psi (2.07 kPa) was changed from 60 minutes to 120 minutes, and thereafter the measurement was carried out in the same way. The saline flow conductivity (SFC) as measured after the swelling time of 60 minutes is herein referred to as SFC (1 hr), and the saline flow conductivity (SFC) as measured after the swelling time of 120 minutes is herein referred to as SFC (2 hr). The retention ratio of the SFC is represented by the following equation:

Retention ratio (%) of SFC=[SFC(2 hr)/SFC(1 hr)]×100

<Retention Ratio of Saline Flow Conductivity (SFC) After Paint Shaker Test (Retention Ratio After PS)>:

The following measurement was carried out on the basis of the apparatus as disclosed in JP-A-235378/1997 (Kokai).

A glass bottle of 6 cm in diameter and about 11 cm in height having a lid was charged with 30 g of water-absorbent resin composition and about 10 g of glass beads (diameter: 6 mm), and then attached to a TOYOSEIKI PAINT SHAKER (for 100 V, 60 HZ), and then shaken for 30 minutes. The glass beads and the water-absorbent resin composition were sieved with a metal gauze having a mesh opening size of about 2 mm, thus obtaining a water-absorbent resin composition after the paint shaker test. The liquid permeation rate under load of the obtained water-absorbent resin composition was measured by the aforementioned method. When the liquid permeation rate under load of the water-absorbent resin composition after the paint shaker test is represented by SFC (after PS) and when the liquid permeation rate under load of the water-absorbent resin composition before the paint shaker test is represented by SFC (before PS), then the retention ratio after PS is represented by the following equation:

Retention ratio (%) after PS=[SFC(after PS)/SFC(before PS)]×100

<Contact Angle>:

A double-coated pressure-sensitive adhesive tape was stuck onto an SUS sheet, and then the water-absorbent resin or water-absorbent resin composition was closely and uniformly spread onto this double-coated tape, and then the water-absorbent resin or water-absorbent resin composition which had not adhered to the double-coated tape was scraped off to prepare a specimen sheet of which the surface was covered with the water-absorbent resin or water-absorbent resin composition. When a physiological saline solution (0.90 mass %) was made to contact with the above specimen sheet, the contact angle was measured by the sessile drop method with a contact angle meter (FACE CA-X model, produced by Kyowa Kaimen Kagaku K.K.) under conditions of 20° C. and 60% RH. The contact angle at 1 second later than dropping a liquid drop of the physiological saline solution onto the specimen sheet was measured 5 times per one specimen. Its average value was determined and taken as the contact angle of the water-absorbent resin or water-absorbent resin composition.

<Extractable (Water-Extractable) Component Content>:

Into a plastic receptacle of 250 ml in capacity having a lid, 184.3 g of 0.90 mass % physiological saline solution was weighed out. Then, 1.00 g of water-absorbent resin particles or water-absorbent resin composition was added to this aqueous solution, and they were stirred for 16 hours, thereby the extractable component content in the resin was extracted. This extract liquid was filtrated with a filter paper (produced by ADVANTEC Toyo Co., Ltd., trade name: (JIS P 3801, No. 2), thickness: 0.26 mm, diameter of captured particles: 5 µm), and then 50.0 g of the resultant filtrate was weighed out and used as a measuring solution.

To begin with, only the 0.90 mass % physiological saline solution was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).

The same titration procedure was carried out for the measuring solution, thus obtaining titration amounts ([NaOH] ml and [HCl] ml).

For example, if the water-absorbent resin or water-absorbent resin particles or water-absorbent resin composition comprises acrylic acid and its sodium salt in known amounts, the extractable component content of the water-absorbent resin can be calculated from the average molecular weight of the monomers and the titration amounts, as obtained from the above procedures, in accordance with the following equation. In the case of unknown amounts, the average molecular weight of the monomers is calculated from the neutralization degree as determined by the titration.

Extractable component content (mass %)=0.1×(average molecular weight)×184.3×10×([HCl]−[bHCl])/1,000/1.0/50.0

Neutralization degree (mol %)=(1−([NaOH]−[bNaOH])/([HCl]−[bHCl]))×100

<Quantification of Metal Compound>:

Appropriate publicly known methods are used for the quantification of the metal compound. For example, the quantification is carried out by such as atomic absorption photometry, plasma emission spectrometry, and absorption photometry which uses color reaction reagents. When it comes to the water-soluble metal compounds, the plasma emission spectrometry is favorably used. Hereinafter an example of the measurement methods is cited.

An amount of 1.0 g of water-absorbent resin composition was weighed out into a polypropylene-made beaker of 260 ml in capacity, and then thereto 190.0 g of 0.90 mass % physiological saline solution and 10.0 g of 2N hydrochloric acid were added, and then they were stirred at room temperature for 30 minutes. After the stirring, the resultant supernatant was filtered with a chromatodisk (GL Chromatodisk 25A of GL Science). The filtrate was analyzed by plasma emission spectrometry (with ULTIMA, produced by Horiba Seisakusho) to determine the metal salt concentration. Incidentally, the calibration curve was prepared from a 0.90 mass % physiological saline solution containing a known amount of polyvalent metal. Based on the determined polyvalent metal concentration, the polyvalent metal concentration in the water-absorbent resin composition is shown by the following equation:

Polyvalent metal concentration (mass %) in water-absorbent resin composition=(polyvalent metal concentration (mass %) in solution)×200

<Metal Compound Segregation Index>:

This is a numerical value indicating the tendency for the segregation of the metal compound to occur and is measured by the following method.

The metal compound as contained in the water-absorbent resin composition is quantified by the aforementioned method and calculated from the following equation:

Metal compound segregation index=$W71$ (ppm)/$W72$ (ppm)

The W71 represents a concentration (ppm) of a metal component which is, for example, contained in a water-absorbent resin composition having passed through a JIS standard sieve of 300 µm in mesh opening size (a portion having particle diameters of not larger than 300 µm) by carrying out the classification operation in the same way as of the aforementioned measurement of the mass-average particle diameter. In addition, the W72 represents a concentration (ppm) of the metal component which is contained in a water-absorbent resin composition before the classification operation. The mesh opening size of the sieve in the present measurement method is changed appropriately for the mass-average particle diameter of the water-absorbent resin composition. Concretely, it is specified as follows: when the mass-average particle diameter is not larger than 150 µm, a JIS standard sieve of 45 µm in mesh opening size should be used; when the mass-average particle diameter is in the range of 150 to 300 µm, a JIS standard sieve of 150 µm in mesh opening size should be used; when the mass-average particle diameter is in the range of 300 to 500 µm, a JIS standard sieve of 300 µm in mesh opening size should be used; and, when the mass-average particle diameter is not smaller than 500 µm, a JIS standard sieve of 500 µm in mesh opening size should be used.

<Blocking Ratio (BR)>:

This refers to a blocking ratio when having been put at 25° C. and a relative humidity of 70% for 1 hour.

An amount of 2 g of water-absorbent resin particles (or water-absorbent resin composition) is uniformly spread onto a bottom of a polypropylene-made cup of 50 mm in inner diameter of the bottom and 10 mm in height and then quickly placed into a thermohumidistatic incubator (PLATIOOUS LUCIFER PL-2G, produced by Tabai Espec Co., Ltd.) (which had beforehand been adjusted to 25° C. and the relative humidity of 70%) and then left alone for 60 minutes. Thereafter, the water-absorbent resin particles having absorbed the moisture were transferred onto a JIS standard sieve of 7.5 cm in diameter and 2,000 μm in mesh opening size and then sieved with a shaking classifier (IIDA SIEVE SHAKER, TYPE: ES-65 type, SER. No. 0501) for 5 minutes. Then, mass W4 (g) of water-absorbent resin particles remaining on the sieve and mass W5 (g) of water-absorbent resin particles having passed through the sieve were measured.

The moisture absorption blocking ratio (%) was calculated from the following equation:

Moisture absorption blocking ratio (%)=mass $W4$ (g)/
(mass $W4$ (g)+mass $W5$ (g))×100

The lower the moisture absorption blocking ratio is, the more excellent the moisture absorption flowability is.

As to the below-mentioned experiments for demonstrating the effects of adding the metal compound, it is favorable that the same precursor is used to compare the above effects. For example, if the particle diameter distribution of the precursor varies, there is a possibility that the parameters depending on the particle diameter distribution, such as SFC, cannot precisely be evaluated. For example, when the performance, as indicated by the SFC, of water-absorbent resin particles is compared, it is favorable to compare the SFC using water-absorbent resin particles having almost the same CRC and particle diameter distributions.

REFERENTIAL EXAMPLE 1

In a reactor as prepared by lidding a jacketed stainless twin-arm kneader of 10 liters in capacity having two sigma-type blades, there was prepared a reaction liquid by dissolving 11.7 g (0.10 mol %) of polyethylene glycol diacrylate into 5,438 g of aqueous solution of sodium acrylate having a neutralization degree of 71.3 mol % (monomer concentration: 39 mass %). Next, this reaction liquid was deaerated under an atmosphere of nitrogen gas for 30 minutes. Subsequently, 29.34 g of 10 mass % aqueous sodium persulfate solution and 24.45 g of 0.1 mass % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer was taken out after 30 minutes from the start of the polymerization. The crosslinked hydrogel polymer as obtained above was in the form of finely divided pieces having diameters of not larger than about 5 mm. This finely divided crosslinked hydrogel polymer was spread onto a metal gauze of 50 meshes (mesh opening size: 300 μm) and then hot-air-dried at 180° C. for 50 minutes, thus obtaining a water-absorbent resin (1) which was of the irregular shape and easy to pulverize, such as in the form of particles, a powder, or a particulate dried material agglomerate.

The resultant water-absorbent resin (1) was pulverized with a roll mill and then further classified with a JIS standard sieve having a mesh opening size of 850 μm. Next, particles having passed through the 850 μm in the aforementioned operation were classified with a JIS standard sieve having a mesh opening size of 150 μm, whereby a water-absorbent resin (1aF) passing through the JIS standard sieve having the mesh opening size of 150 μm was removed, thus obtaining a particulate water-absorbent resin (1a).

The resultant water-absorbent resin (1aF) was agglomerated according to the method of Granulation Example 1 as disclosed in U.S. Pat. No. 6,228,930. The resultant agglomerated material was pulverized and classified by the same procedure as the aforementioned, thus obtaining an agglomerated water-absorbent resin (1aA).

An amount of 90 mass parts of the water-absorbent resin (1a) and 10 mass parts of the water-absorbent resin (1aA), as obtained in the above way, were uniformly mixed together to obtain a water-absorbent resin (A).

In addition, similarly, the resultant water-absorbent resin (1) was pulverized with a roll mill and then further classified with a JIS standard sieve having a mesh opening size of 710 μm. Next, particles having passed through the 710 μm in the aforementioned operation were classified with a JIS standard sieve having a mesh opening size of 150 μm, whereby water-absorbent resin particles (1bF) passing through the JIS standard sieve having the mesh opening size of 150 μm were removed, thus obtaining a particulate water-absorbent resin (1b).

The resultant water-absorbent resin (1bF) was agglomerated according to the method of Granulation Example 1 as disclosed in U.S. Pat. No. 6,228,930. The resultant agglomerated material was pulverized and classified by the same procedure as the aforementioned, thus obtaining an agglomerated water-absorbent resin (1bA).

An amount of 85 mass parts of the water-absorbent resin (1b) and 15 mass parts of the water-absorbent resin (1bA), as obtained in the above way, were uniformly mixed together to obtain a water-absorbent resin (B).

In addition, similarly, the resultant water-absorbent resin (1) was pulverized with a roll mill and then further classified with a JIS standard sieve having a mesh opening size of 600 μm. Next, particles having passed through the 600 μm in the aforementioned operation were classified with a JIS standard sieve having a mesh opening size of 150 μm, whereby water-absorbent resin particles (1cF) passing through the JIS standard sieve having the mesh opening size of 150 μm were removed, thus obtaining a particulate water-absorbent resin (1c).

The resultant water-absorbent resin (1cF) was agglomerated according to the method of Granulation Example 1 as disclosed in U.S. Pat. No. 6,228,930. The resultant agglomerated material was pulverized and classified by the same procedure as the aforementioned, thus obtaining an agglomerated water-absorbent resin (1cA).

An amount of 80 mass parts of the water-absorbent resin (1c) and 20 mass parts of the water-absorbent resin (1cA), as obtained in the above way, were uniformly mixed together to obtain a water-absorbent resin (C).

REFERENTIAL EXAMPLE 2

An amount of 100 g of the water-absorbent resin (C) as obtained from the aforementioned Referential Example 1 was mixed with a surface-treating agent comprising a mixed liquid of 0.5 g of 1,4-butanediol, 1.0 g of propylene glycol, and 3.0 g of pure water, and then the resultant mixture was heat-treated at 210° C. for 30 minutes. Furthermore, the resultant particles were disintegrated to such a degree that they could pass through a JIS standard sieve having a mesh opening size of 600 μm. As a result, a surface-crosslink-treated water-absorbent resin (C1) was obtained.

The results of having measured the properties of the water-absorbent resin (C1) are shown in Table 1.

REFERENTIAL EXAMPLE 3

An amount of 100 g of the water-absorbent resin (A) as obtained from the aforementioned Referential Example 1 was mixed with a surface-treating agent comprising a mixed liquid of 0.1 g of 2-ethyloxetane, 3.0 g of pure water, and 0.3 g of 24 mass % aqueous sodium hydroxide solution, and then the resultant mixture was heat-treated at 200° C. for 30 minutes. Furthermore, the resultant particles were disintegrated to such a degree that they could pass through a JIS standard sieve having a mesh opening size of 850 μm. As a result, a surface-crosslink-treated water-absorbent resin (A1) was obtained.

The results of having measured the properties of the water-absorbent resin (A1) are shown in Table 1.

REFERENTIAL EXAMPLE 4

An amount of 100 g of the water-absorbent resin (B) as obtained from the aforementioned Referential Example 1 was mixed with a surface-treating agent comprising a mixed liquid of 0.5 g of 2-oxazolidinone, 1.0 g of propylene glycol, and 4.0 g of pure water, and then the resultant mixture was heat-treated at 190° C. for 30 minutes. Furthermore, the resultant particles were disintegrated to such a degree that they could pass through a JIS standard sieve having a mesh opening size of 710 μm. As a result, a surface-crosslink-treated water-absorbent resin (B1) was obtained.

The results of having measured the properties of the water-absorbent resin (B1) are shown in Table 1.

REFERENTIAL EXAMPLE 5

An amount of 100 g of the water-absorbent resin (C) as obtained from the aforementioned Referential Example 1 was mixed with a surface-treating agent comprising a mixed liquid of 0.5 g of ethylene carbonate, 1.0 g of propylene glycol, and 4.0 g of pure water, and then the resultant mixture was heat-treated at 195° C. for 30 minutes. Furthermore, the resultant particles were disintegrated to such a degree that they could pass through a JIS standard sieve having a mesh opening size of 600 μm. As a result, a surface-crosslink-treated water-absorbent resin (C2) was obtained.

The results of having measured the properties of the water-absorbent resin (C2) are shown in Table 1.

REFERENTIAL EXAMPLE 6

An amount of 100 g of the water-absorbent resin (A) as obtained from the aforementioned Referential Example 1 was mixed with a surface-treating agent comprising a mixed liquid of 0.5 g of ethylene carbonate, 6.0 g of pure water, and 0.5 g of aluminum sulfate tetradeca- to octadecahydrates (obtained from Kanto Chemical Co., Inc.), and then the resultant mixture was heat-treated at 195° C. for 30 minutes. Furthermore, the resultant particles were disintegrated to such a degree that they could pass through a JIS standard sieve having a mesh opening size of 850 μm. As a result, a surface-crosslink-treated water-absorbent resin (A2) was obtained.

The results of having measured the properties of the water-absorbent resin (A2) are shown in Table 1.

REFERENTIAL EXAMPLE 7

Aluminum sulfate tetradeca- to octadecahydrates (obtained from Kanto Chemical Co., Inc.) were classified with JIS standard sieves having mesh opening sizes of 600 μm, 300 μm, and 150 μm, thus obtaining aluminum sulfate tetradeca- to octadecahydrates (1) having particle diameters of substantially not larger than 150 μm, aluminum sulfate tetradeca- to octadecahydrates (2) having particle diameters of substantially 300 to 150 μm, and aluminum sulfate tetradeca- to octadecahydrates (3) having particle diameters of substantially 600 to 300 μm. The mass-average particle diameter of the aluminum sulfate tetradeca- to octadecahydrates (1) was 95 μm, the mass-average particle diameter of the aluminum sulfate tetradeca- to octadecahydrates (2) was 203 μm, and the mass-average particle diameter of the aluminum sulfate tetradeca- to octadecahydrates (3) was 401 μm.

EXAMPLE 1

An amount of 100 mass parts of the water-absorbent resin (C1), as obtained from Referential Example 2, was uniformly mixed with 0.5 mass part of aluminum sulfate hydrates (trideca- to tetradecahydrates, obtained from Sumitomo Chemical Co., Ltd., mass-average particle diameter: 165 μm, bulk density: 0.86 g/cm$^3$, solubility into pure water of 0° C.: 46.4 mass %), thus obtaining a water-absorbent resin composition (1).

The results of having measured the properties of the resultant water-absorbent resin composition (1) are shown in Table 1. In addition, the result of having further measured the CSF is shown in Table 4.

EXAMPLE 2

An amount of 100 mass parts of the water-absorbent resin (C1), as obtained from Referential Example 2, was uniformly mixed with 1.0 mass part of aluminum sulfate tetradeca- to octadecahydrates (obtained from Kanto Chemical Co., Inc., mass-average particle diameter: 182 μm, bulk density: 0.60 g/cm$^3$), thus obtaining a water-absorbent resin composition (2).

The results of having measured the properties of the resultant water-absorbent resin composition (2) are shown in Table 1. In addition, the result of having further measured the retention ratio of the saline flow conductivity (SFC) is shown in Table 2, and the result of having further measured the CSF is shown in Table 4.

EXAMPLE 3

An amount of 100 mass parts of the water-absorbent resin (A1), as obtained from Referential Example 3, was uniformly mixed with 1.0 mass part of aluminum sulfate hydrates (trideca- to tetradecahydrates, obtained from Sumitomo Chemical Co., Ltd., mass-average particle diameter: 165 μm, bulk density: 0.86 g/cm$^3$), thus obtaining a water-absorbent resin composition (3).

The results of having measured the properties of the resultant water-absorbent resin composition (3) are shown in Table 1.

EXAMPLE 4

An amount of 100 mass parts of the water-absorbent resin (B1), as obtained from Referential Example 4, was uniformly mixed with 0.1 mass part of aluminum sulfate hydrates (trideca- to tetradecahydrates, obtained from Sumitomo Chemical Co., Ltd., mass-average particle diameter: 165 μm, bulk density: 0.86 g/cm³), thus obtaining a water-absorbent resin composition (4).

The results of having measured the properties of the resultant water-absorbent resin composition (4) are shown in Table 1.

EXAMPLE 5

An amount of 100 mass parts of the water-absorbent resin (C2), as obtained from Referential Example 5, was uniformly mixed with 0.5 mass part of aluminum sulfate hydrates (trideca- to tetradecahydrates, obtained from Sumitomo Chemical Co., Ltd., mass-average particle diameter: 165 μm, bulk density: 0.86 g/cm³), thus obtaining a water-absorbent resin composition (5).

The results of having measured the properties of the resultant water-absorbent resin composition (5) are shown in Table 1.

EXAMPLE 6

An amount of 100 mass parts of the water-absorbent resin (C1), as obtained from Referential Example 2, was uniformly mixed with 0.5 mass part of the aluminum sulfate tetradeca- to octadecahydrates (1) as obtained from Referential Example 7, thus obtaining a water-absorbent resin composition (6).

The results of having measured the properties of the resultant water-absorbent resin composition (6) are shown in Table 1.

EXAMPLE 7

An amount of 100 mass parts of the water-absorbent resin (C1), as obtained from Referential Example 2, was uniformly mixed with 0.5 mass part of the aluminum sulfate tetradeca- to octadecahydrates (2) as obtained from Referential Example 7, thus obtaining a water-absorbent resin composition (7).

The results of having measured the properties of the resultant water-absorbent resin composition (7) are shown in Table 1.

EXAMPLE 8

An amount of 100 mass parts of the water-absorbent resin (C1), as obtained from Referential Example 2, was uniformly mixed with 0.5 mass part of the aluminum sulfate tetradeca- to octadecahydrates (3) as obtained from Referential Example 7, thus obtaining a water-absorbent resin composition (8).

The results of having measured the properties of the resultant water-absorbent resin composition (8) are shown in Table 1.

EXAMPLE 9

The wettability to a physiological saline solution was evaluated by the contact angle as to water-absorbent resin compositions.

The contact angle with the physiological saline solution was measured by the aforementioned method as to the water-absorbent resin composition (1) as obtained from Example 1 (aluminum sulfate-added material) (before the PS) and as to a water-absorbent resin composition as obtained in the same way as of Example 1 except the aluminum sulfate was replaced with Aerosil R-972 (produced by Nippon Aerosil Co., Ltd.).

The results of having measured the contact angle are shown in Table 3.

COMPARATIVE EXAMPLE 1

The water-absorbent resin (C1), as obtained from Referential Example 2, was taken as a comparative water-absorbent resin (1).

The results of having measured the properties of the resultant comparative water-absorbent resin (1) are shown in Table 1.

COMPARATIVE EXAMPLE 2

An amount of 100 mass parts of the water-absorbent resin (A), as obtained from Referential Example 1, was uniformly mixed with 0.5 mass part of aluminum sulfate tetradeca- to octadecahydrates (obtained from Kanto Chemical Co., Inc., mass-average particle diameter: 182 μm, bulk density: 0.60 g/cm³), thus obtaining a comparative water-absorbent resin composition (2).

The results of having measured the properties of the resultant comparative water-absorbent resin composition (2) are shown in Table 1. In addition, the result of having further measured the CSF is shown in Table 4.

COMPARATIVE EXAMPLE 3

An amount of 100 mass parts of the water-absorbent resin (A), as obtained from Referential Example 1, was uniformly mixed with 5 mass parts of 10 mass % aqueous solution of aluminum sulfate tetradeca- to octadecahydrates (obtained from Kanto Chemical Co., Inc., mass-average particle diameter: 182 μm, bulk density: 0.60 g/cm³, solubility into pure water of 23° C.: 37.5 mass %), thus obtaining a comparative water-absorbent resin composition (3).

The results of having measured the properties of the resultant comparative water-absorbent resin composition (3) are shown in Table 1. In addition, the result of having further measured the CSF is shown in Table 4.

COMPARATIVE EXAMPLE 4

An amount of 100 mass parts of the water-absorbent resin (C1), as obtained from Referential Example 2, was uniformly mixed with 5 mass parts of 10 mass % aqueous solution of aluminum sulfate tetradeca- to octadecahydrates (obtained from Kanto Chemical Co., Inc., mass-average particle diameter: 182 μm, bulk density: 0.60 g/cm³), thus obtaining a comparative water-absorbent resin composition (4).

The results of having measured the properties of the resultant comparative water-absorbent resin composition (4) are shown in Table 1. In addition, the result of having further measured the retention ratio of the saline flow conductivity (SFC) is shown in Table 2.

COMPARATIVE EXAMPLE 5

The water-absorbent resin (A2), as obtained from Referential Example 6, was taken as a comparative water-absorbent resin (5).

The results of having measured the properties of the resultant comparative water-absorbent resin (5) are shown in Table 1. In addition, the result of having further measured the CSF is shown in Table 4.

COMPARATIVE EXAMPLE 6

An amount of 100 mass parts of the water-absorbent resin (C2), as obtained from Referential Example 5, was uniformly mixed with 0.5 mass part of aluminum sulfate hydrates (trideca- to tetradecahydrates, obtained from Sumitomo Chemical Co., Ltd., mass-average particle diameter: 165 μm, bulk density: 0.86 g/cm$^3$), and then adding 5 mass parts of pure water to the resultant mixture, thus obtaining a comparative water-absorbent resin composition (6).

The results of having measured the properties of the resultant comparative water-absorbent resin composition (6) are shown in Table 1.

EXAMPLE 10

Examinations with electron photomicrographs were made about the states of the aluminum sulfates in the water-absorbent resin composition (2) as obtained from Example 2, the comparative water-absorbent resin composition (4) as obtained from Comparative Example 4, and the comparative water-absorbent resin composition (6) as obtained from Comparative Example 6.

In the water-absorbent resin composition (2), the aluminum sulfate was present in the form of particles. However, in the comparative water-absorbent resin compositions (4) and (6), the aluminum sulfate was partially or entirely dissolved and was therefore not present in the form of particles. Incidentally, the presence of the aluminum sulfate was confirmed by EPMA analysis into aluminum.

TABLE 1

| | Water-absorbent resin as precursor | | Mass-average particle diameter μm | CRC g/g | AAP g/g | SFC (before PS) (×10$^{-7}$·cm$^3$·s·g$^{-1}$) | SFC (after PS) (×10$^{-7}$·cm$^3$·s·g$^{-1}$) | Retention ratio after PS % |
|---|---|---|---|---|---|---|---|---|
| Referential Example 2 | C (600-150 μm) | Water-absorbent resin (C1) | 302 | 26 | 25 | 72 | — | — |
| Referential Example 3 | A (850-150 μm) | Water-absorbent resin (A1) | 435 | 30 | 26 | 42 | — | — |
| Referential Example 4 | B (710-150 μm) | Water-absorbent resin (B1) | 362 | 24 | 23 | 121 | — | — |
| Referential Example 5 | C (600-150 μm) | Water-absorbent resin (C2) | 301 | 28 | 25 | 54 | — | — |
| Referential Example 6 | A (850-150 μm) | Water-absorbent resin (A2) | 437 | 29 | 23 | 50 | — | — |
| Example 1 | C1 | Water-absorbent resin composition (1) | 300 | 26 | 24 | 150 | 121 | 81 |
| Example 2 | C1 | Water-absorbent resin composition (2) | 304 | 26 | 24 | 168 | 132 | 79 |
| Example 3 | A1 | Water-absorbent resin composition (3) | 432 | 30 | 25 | 63 | 45 | 71 |
| Example 4 | B1 | Water-absorbent resin composition (4) | 359 | 24 | 22 | 186 | 135 | 73 |
| Example 5 | C2 | Water-absorbent resin composition (5) | 297 | 28 | 24 | 102 | 73 | 72 |
| Example 6 | C1 | Water-absorbent resin composition (6) | 298 | 26 | 24 | 156 | 128 | 82 |
| Example 7 | C1 | Water-absorbent resin composition (7) | 301 | 26 | 24 | 140 | 134 | 96 |

TABLE 1-continued

| | Water-absorbent resin as precursor | | Mass-average particle diameter μm | CRC g/g | AAP g/g | SFC (before PS) (×10⁻⁷·cm³·s·g⁻¹) | SFC (after PS) (×10⁻⁷·cm³·s·g⁻¹) | Retention ratio after PS % |
|---|---|---|---|---|---|---|---|---|
| Example 8 | C1 | Water-absorbent resin composition (8) | 305 | 26 | 24 | 128 | 131 | 102 |
| Comparative Example 1 | C1 | Comparative water-absorbent resin (1) | 302 | 26 | 25 | 72 | 42 | 58 |
| Comparative Example 2 | A | Comparative water-absorbent resin composition (2) | 431 | 33 | 11 | 3 | — | — |
| Comparative Example 3 | A | Comparative water-absorbent resin composition (3) | 430 | 33 | 10 | 2 | — | — |
| Comparative Example 4 | C1 | Comparative water-absorbent resin composition (4) | 301 | 25 | 21 | 112 | 46 | 41 |
| Comparative Example 5 | A2 | Comparative water-absorbent resin (5) | 437 | 29 | 22 | 50 | 23 | 46 |
| Comparative Example 6 | C2 | Comparative water-absorbent resin composition (6) | 314 | 27 | 23 | 98 | 43 | 44 |

TABLE 2

| | Water-absorbent resin | | SFC (1 hr) (×10⁻⁷·cm³·s·g⁻¹) | SFC (2 hr) (×10⁻⁷·cm³·s·g⁻¹) | Retention ratio of SFC % |
|---|---|---|---|---|---|
| Example 2 | C1 | Water-absorbent resin composition (2) | 168 | 112 | 67 |
| Comparative Example 4 | C1 | Comparative water-absorbent resin composition (4) | 112 | 43 | 38 |

TABLE 3

| Inorganic compound added | Contact angle (degrees) |
|---|---|
| Aluminum sulfate tetradeca- to octadecahydrates | 16.9 |
| Aerosil R-972 | 87.7 |

Note)
Aerosil R-972: hydrophobic silica, produced by Nippon Aerosil Co., Ltd. in dry manner

TABLE 4

| | | CSF g/g |
|---|---|---|
| Example 1 | Water-absorbent resin composition (1) | 23 |
| Example 2 | Water-absorbent resin composition (2) | 22 |
| Comparative Example 2 | Comparative water-absorbent resin composition (2) | 7 |
| Comparative Example 3 | Comparative water-absorbent resin composition (3) | 5 |
| Comparative Example 5 | Comparative water-absorbent resin (5) | 18 |

REFERENTIAL EXAMPLE 8

In a reactor as prepared by lidding a jacketed stainless twin-arm kneader of 10 liters in capacity having two sigma-type blades, there was prepared a reaction liquid by dissolving 11.7 g (0.10 mol %) of polyethylene glycol diacrylate into 5,438 g of aqueous solution of sodium acrylate having a neutralization degree of 71.3 mol % (monomer concentration: 39 mass %). Next, this reaction liquid was deaerated under an atmosphere of nitrogen gas for 30 minutes. Subsequently, 29.34 g of 10 mass % aqueous sodium persulfate solution and 24.45 g of 0.1 mass % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer was taken out after 30 minutes from the start of the polymerization. The crosslinked hydrogel polymer as obtained above was in the form of finely divided pieces having diameters of not larger than about 5 mm. This finely divided crosslinked hydrogel polymer was spread onto a metal gauze of 50 meshes (mesh opening size: 300 μm) and then hot-air-dried at 180° C. for 50 minutes, thus obtaining a water-absorbent resin (1) which was of the irregular shape and easy to pulverize, such as in the form of a particulate dried material agglomerate.

The resultant water-absorbent resin (1) was pulverized with a roll mill and then further classified with a JIS standard sieve having a mesh opening size of 850 μm. Next, particles having passed through the 850 μm in the aforementioned operation were classified with a JIS standard sieve having a mesh opening size of 150 μm, whereby a water-absorbent resin (1aF) passing through the JIS standard sieve having the mesh opening size of 150 μm was removed, thus obtaining a particulate water-absorbent resin (1a).

The removed water-absorbent resin (1aF) was agglomerated according to the method of Granulation Example 1 as disclosed in U.S. Pat. No. 6,228,930. The resultant agglomerated material was pulverized and classified by the same procedure as the aforementioned, thus obtaining an agglomerated water-absorbent resin (1aA).

An amount of 80 mass parts of the water-absorbent resin (1a) and 20 mass parts of the water-absorbent resin (1aA), as obtained in the above way, were uniformly mixed together to obtain a water-absorbent resin (1C).

Next, 500 g of the water-absorbent resin (1C) and a surface-treating agent comprising a mixed liquid of 2.5 g of 1,4-butanediol, 5.0 g of propylene glycol, and 15.0 g of pure water were mixed together, and then the resultant mixture was heat-treated at 210° C. for 30 minutes. The heat-treated water-absorbent resin was disintegrated to such a degree that it could pass through a JIS standard sieve having a mesh opening size of 600 μm. As a result, a surface-crosslinked water-absorbent resin (1D) was obtained.

Various properties of the surface-crosslinked water-absorbent resin (1D) are shown in Table 5.

The dust generation degree of the surface-crosslinked water-absorbent resin (1D) is shown in Table 6.

EXAMPLE 11

An amount of 300 g of the surface-crosslinked water-absorbent resin (1D), as obtained from Referential Example 8, was preheated to 60° C., and then spraywise mixed with 1.5 g of water under stirring by a Lödige mixer. Subsequently, 3 g of aluminum sulfate tetradeca- to octadecahydrates was added thereto to mix them together under stirring by the Lödige mixer, and then the resultant mixture was left alone at room temperature for 30 minutes. The resultant mixture was disintegrated to such a degree that it could pass through a JIS standard sieve having a mesh opening size of 600 μm. As a result, a water-absorbent resin composition (11) was obtained.

Various properties of the water-absorbent resin composition (11) are shown in Table 5.

The dust generation degree of the water-absorbent resin composition (11) is shown in Table 6.

EXAMPLES 12 TO 14

Water-absorbent resin compositions (12) to (14) were obtained in the same way as of Example 11 except that the amount of water being used was changed to 3 g, 4.5 g, and 6 g respectively.

Various properties of the water-absorbent resin compositions (12) to (14) are shown in Table 5.

The dust generation degrees of the water-absorbent resin compositions (12) to (14) are shown in Table 6.

EXAMPLE 15

A water-absorbent resin composition (15) was obtained in the same way as of Example 11 except that the 1.5 g of water was replaced with 6 g of aqueous solution of water/glycerol=50/50 (wt/wt).

Various properties of the water-absorbent resin composition (15) are shown in Table 5.

EXAMPLE 16

A water-absorbent resin composition (16) was obtained in the same way as of Example 11 except that the 1.5 g of water was replaced with 6 g of aqueous solution of water/propylene glycol=50/50 (wt/wt).

Various properties of the water-absorbent resin composition (16) are shown in Table 5.

EXAMPLE 17

A water-absorbent resin composition (17) was obtained in the same way as of Example 11 except that the 1.5 g of water was replaced with 6 g of aqueous solution of water/polyethylene glycol (average molecular weight: 600)=50/50 (wt/wt).

Various properties of the water-absorbent resin composition (17) are shown in Table 5.

COMPARATIVE EXAMPLE 7

An amount of 300 g of the surface-crosslinked water-absorbent resin (1D), as obtained from Referential Example 8, and 3 g of aluminum sulfate tetradeca- to octadecahydrates were mixed (dry-blended) together under stirring by a Lödige mixer, thus obtaining a comparative water-absorbent resin composition (7).

Various properties of the comparative water-absorbent resin composition (7) are shown in Table 5.

EXAMPLE 18

An amount of 500 g of the not yet surface-crosslinked water-absorbent resin (1C), as obtained from Referential Example 8, was preheated to 50° C., and then mixed with a surface-treating agent comprising a mixed liquid of 2.5 g of 1,4-butanediol, 5.0 g of propylene glycol, and 15.0 g of pure water by a Lödige mixer. Subsequently, 3 g of aluminum sulfate tetradeca- to octadecahydrates was added thereto to mix them together under stirring by the Lödige mixer. The resultant mixture was heat-treated at 210° C. for 30 minutes and then disintegrated to such a degree that it could pass through a JIS standard sieve having a mesh opening size of 600 μm. As a result, a water-absorbent resin composition (18) was obtained.

Various properties of the water-absorbent resin composition (18) are shown in Table 5.

COMPARATIVE EXAMPLE 8

An amount of 500 g of the not yet surface-crosslinked water-absorbent resin (1C), as obtained from Referential Example 8, and a surface-treating agent comprising a mixed liquid of 2.5 g of 1,4-butanediol, 5.0 g of propylene glycol, 3 g of aluminum sulfate tetradeca- to octadecahydrates, and 15.0 g of pure water were mixed together by a Lödige mixer. The resultant mixture was heat-treated at 210° C. for 30 minutes and then disintegrated to such a degree that it could pass through a JIS standard sieve having a mesh opening size of 600 μm. As a result, a comparative water-absorbent resin composition (8) was obtained.

Various properties of the comparative water-absorbent resin composition (8) are shown in Table 5.

COMPARATIVE EXAMPLE 9

An amount of 500 g of the surface-crosslinked water-absorbent resin (1D), as obtained from Referential Example 8, was spraywise mixed with 50 g of 12 mass % aqueous solution of aluminum sulfate tetradeca- to octadecahydrates under stirring by a Lödige mixer. Next, the resultant mixture was dried at 80° C. for 30 minutes. The resultant dried material was disintegrated to such a degree that it could pass through a JIS standard sieve having a mesh opening size of 600 μm. As a result, a comparative water-absorbent resin composition (9) was obtained.

Various properties of the comparative water-absorbent resin composition (9) are shown in Table 5.

COMPARATIVE EXAMPLE 10

An amount of 500 g of the comparative water-absorbent resin composition (7), as obtained from Comparative Example 7, was spraywise mixed with 10 g of water by a Lödige mixer and then left alone at room temperature for 30 minutes. The resultant mixture was disintegrated to such a degree that it could pass through a JIS standard sieve having a mesh opening size of 600 μm. As a result, a comparative water-absorbent resin composition (10) was obtained.

Various properties of the comparative water-absorbent resin composition (10) are shown in Table 5.

EXAMPLE 19

A water-absorbent resin composition (19) was obtained in the same way as of Example 13 except that aluminum sulfate tetradeca- to octadecahydrates having passed through a JIS standard sieve having a mesh opening size of 105 μm was used.

Various properties of the water-absorbent resin composition (19) are shown in Table 5.

REFERENTIAL EXAMPLE 9

First of all, a water-absorbent resin (2), which was of the irregular shape and easy to pulverize, such as in the form of a particulate dried material agglomerate, was obtained in the same way as of Referential Example 8 except that the polyethylene glycol diacrylate was used in an amount of 7.6 g.

Specifically, in a reactor as prepared by lidding a jacketed stainless twin-arm kneader of 10 liters in capacity having two sigma-type blades, there was prepared a reaction liquid by dissolving 7.6 g (0.065 mol %) of polyethylene glycol diacrylate into 5,438 g of aqueous solution of sodium acrylate having a neutralization degree of 71.3 mol % (monomer concentration: 39 mass %). Next, this reaction liquid was deaerated under an atmosphere of nitrogen gas for 30 minutes. Subsequently, 29.34 g of 10 mass % aqueous sodium persulfate solution and 24.45 g of 0.1 mass % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer was taken out after 30 minutes from the start of the polymerization. The crosslinked hydrogel polymer as obtained above was in the form of finely divided pieces having diameters of not larger than about 5 mm. This finely divided crosslinked hydrogel polymer was spread onto a metal gauze of 50 meshes (mesh opening size: 300 μm) and then hot-air-dried at 180° C. for 50 minutes, thus obtaining the water-absorbent resin (2) which was of the irregular shape and easy to pulverize, such as in the form of a particulate dried material agglomerate.

The resultant water-absorbent resin (2) was pulverized with a roll mill and then further classified with a JIS standard sieve having a mesh opening size of 850 μm. Next, particles having passed through the 850 μm in the aforementioned operation were classified with a JIS standard sieve having a mesh opening size of 150 μm, whereby a water-absorbent resin (2aF) passing through the JIS standard sieve having the mesh opening size of 150 μm was removed, thus obtaining a particulate water-absorbent resin (2a).

The removed water-absorbent resin (2aF) was agglomerated according to the method of Granulation Example 1 as disclosed in U.S. Pat. No. 6,228,930. The resultant agglomerated material was pulverized and classified by the same procedure as the aforementioned, thus obtaining an agglomerated water-absorbent resin (2aA).

An amount of 90 mass parts of the water-absorbent resin (2a) and 10 mass parts of the water-absorbent resin (2aA), as obtained in the above way, were uniformly mixed together to obtain a water-absorbent resin (2C).

Next, 500 g of the water-absorbent resin (2C) and a surface-treating agent comprising a mixed liquid of 2.5 g of 1,4-butanediol, 5.0 g of propylene glycol, and 15.0 g of pure water were mixed together, and then the resultant mixture was heat-treated at 210° C. for 30 minutes. The heat-treated water-absorbent resin was disintegrated to such a degree that it could pass through a JIS standard sieve having a mesh opening size of 850 μm. As a result, a surface-crosslinked water-absorbent resin (2D) was obtained.

Various properties of the surface-crosslinked water-absorbent resin (2D) are shown in Table 5.

EXAMPLE 20

A water-absorbent resin composition (20) was obtained in the same way as of Example 13 except that the surface-crosslinked water-absorbent resin (1D) was replaced with the surface-crosslinked water-absorbent resin (2D) as obtained from Referential Example 9.

Various properties of the water-absorbent resin composition (20) are shown in Table 5.

EXAMPLE 21

The distribution of the aluminum sulfate, which was contained every particle diameter range in the water-absorbent resin compositions (11) to (17) as obtained from Examples 11 to 17 and in the comparative water-absorbent resin composition (7) as obtained from Comparative Example 7, was determined in the following way. The results are shown in Table 7.

(i) The water-absorbent resin composition was sieved with JIS standard sieves having mesh opening sizes of 600 μm, 425 μm, and 300 μm to determine the distribution into the particle diameter ranges of 600/425 μm, 425/300 μm, and 300 μm-pass.

(ii) An amount of 1 g of the water-absorbent resin composition, as classified into each particle diameter range in the above step (i), was precisely weighed out.

(iii) A Teflon (registered trademark) rotator of 35 mm was placed into a polypropylene-made beaker of 260 ml., and then thereto 1 g of the water-absorbent resin composition, as weighed out in the above step (ii), 190 g of 0.9 mass % aqueous sodium chloride solution, and 10 g of 2N hydrochloric acid were added, and then they were stirred with a magnetic stirrer for 5 minutes.

(iv) After the stirring, the resultant supernatant was sucked up with a polypropylene-made syringe and then filtered with a chromatodisk (GL Chromatodisk 25A, produced by GL Science).

(v) The filtrate was analyzed by ICP (plasma emission spectrometry) to quantify the amount (%) of the aluminum sulfate which was contained every particle diameter range in the water-absorbent resin composition as classified into each particle diameter range.

(vi) The distribution of the aluminum sulfate every particle diameter range was determined in accordance with the following equation:

Distribution (%) of aluminum sulfate every particle diameter range=[amount (%) of aluminum sulfate every particle diameter range×particle diameter distribution (%)]×100/Σ[amount (%) of aluminum sulfate every particle diameter range× particle diameter distribution (%)]

For example, when the particle diameter distribution in the range of 600/425 μm is 13% and the amount of the aluminum sulfate in the range of 600/425 μm is 0.20%, and when the particle diameter distribution in the range of 425/300 μm is 45% and the amount of the aluminum sulfate in the range of 425/300 μm is 0.17%, and when the particle diameter distribution in the range of 300 μm-pass is 42% and the amount of the aluminum sulfate in the range of 300 μm-pass is 0.89%, then the distribution (%) of the aluminum sulfate in the range of 600/425 μm is determined as follows:

Distribution (%) of aluminum sulfate in the range of 600/425 μm=[0.20×0.13]×100/(0.20×0.13+0.17× 0.45+0.89×0.42)=5(%)

TABLE 5

| | Mass-average particle diameter (μm) | CRC (g/g) | AAP (g/g) | SFC after PS ($\times 10^{-7} \cdot cm^3 \cdot s \cdot g^{-1}$) |
|---|---|---|---|---|
| Water-absorbent resin (1D) | 320 | 26 | 25 | 45 |
| Water-absorbent resin (2D) | 430 | 29 | 24 | 35 |
| Water-absorbent resin composition (11) | 325 | 26 | 24 | 130 |
| Water-absorbent resin composition (12) | 323 | 26 | 24 | 120 |
| Water-absorbent resin composition (13) | 328 | 26 | 24 | 128 |
| Water-absorbent resin composition (14) | 321 | 26 | 24 | 125 |
| Water-absorbent resin composition (15) | 335 | 26 | 24 | 123 |
| Water-absorbent resin composition (16) | 336 | 26 | 24 | 121 |
| Water-absorbent resin composition (17) | 340 | 26 | 24 | 122 |
| Water-absorbent resin composition (18) | 320 | 25 | 23 | 118 |
| Water-absorbent resin composition (19) | 326 | 26 | 24 | 160 |
| Water-absorbent resin composition (20) | 435 | 29 | 24 | 85 |
| Comparative water-absorbent resin composition (7) | 320 | 26 | 25 | 120 |
| Comparative water-absorbent resin composition (8) | 316 | 26 | 22 | 100 |
| Comparative water-absorbent resin composition (9) | 335 | 26 | 21 | 45 |
| Comparative water-absorbent resin composition (10) | 340 | 27 | 21 | 40 |

TABLE 6

| | Dust generation degree (mg/m$^3$) |
|---|---|
| Water-absorbent resin composition (11) | 0.19 |
| Water-absorbent resin composition (12) | 0.14 |
| Water-absorbent resin composition (13) | 0.14 |
| Water-absorbent resin composition (14) | 0.12 |
| Water-absorbent resin (1D) | 0.29 |

TABLE 7

| | Distribution of aluminum sulfate every particle diameter range | | |
|---|---|---|---|
| | 600/425 μm (%) | 425/300 μm (%) | 300 μm-pass (%) |
| Water-absorbent resin composition (11) | 4 | 9 | 87 |
| Water-absorbent resin composition (12) | 5 | 15 | 80 |
| Water-absorbent resin composition (13) | 5 | 15 | 80 |
| Water-absorbent resin composition (14) | 5 | 16 | 79 |
| Water-absorbent resin composition (15) | 6 | 23 | 71 |
| Water-absorbent resin composition (16) | 7 | 20 | 73 |
| Water-absorbent resin composition (17) | 11 | 23 | 66 |
| Comparative water-absorbent resin composition (7) | 2 | 10 | 88 |

REFERENTIAL EXAMPLE 10

In a reactor as prepared by lidding a jacketed stainless twin-arm kneader of 10 liters in capacity having two sigma-type blades, there was prepared a reaction liquid by dissolving 7.14 g (0.06 mol %) of polyethylene glycol diacrylate into 5,438 g of aqueous solution of sodium acrylate having a neutralization degree of 71.3 mol % (monomer concentration: 39 mass %). Next, this reaction liquid was deaerated under an atmosphere of nitrogen gas for 30 minutes. Subsequently, 29.34 g of 10 mass % aqueous sodium persulfate solution and 24.45 g of 0.1 mass % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer was taken out after 30 minutes from the start of the polymerization.

The crosslinked hydrogel polymer as obtained above was in the form of finely divided pieces having diameters of not larger than about 5 mm. This finely divided crosslinked hydrogel polymer was spread onto a metal gauze of 50 meshes (mesh opening size: 300 μm) and then hot-air-dried at 180° C. for 50 minutes. The resultant water-absorbent resin was pulverized with a roll mill and then further classified with JIS standard sieves having mesh opening sizes of 850 μm and 150 μm, thus obtaining water-absorbent resin particles (a).

REFERENTIAL EXAMPLE 11

The same polymerization operation as of Referential Example 10 was carried out except that the reaction liquid was replaced with a reaction liquid as prepared by dissolving 4.02 g (0.035 mol %) of polyethylene glycol diacrylate into 5,444 g of aqueous solution of sodium acrylate having a neutralization degree of 75 mol % (monomer concentration: 38 mass %).

The resultant water-absorbent resin was pulverized with a roll mill and then further classified with JIS standard sieves having mesh opening sizes of 710 μm and 150 μm, thus obtaining water-absorbent resin particles (b).

REFERENTIAL EXAMPLE 12

The same polymerization operation as of Referential Example 10 was carried out except that the reaction liquid was replaced with a reaction liquid as prepared by dissolving 11.7 g (0.1 mol %) of polyethylene glycol diacrylate into 5,438 g of aqueous solution of sodium acrylate having a neutralization degree of 71 mol % (monomer concentration: 38 mass %).

The resultant water-absorbent resin was pulverized with a roll mill and then further classified with JIS standard sieves having mesh opening sizes of 600 μm and 150 μm, thus obtaining water-absorbent resin particles (c).

REFERENTIAL EXAMPLE 13

An amount of 100 g of the water-absorbent resin (a) as obtained from the aforementioned Referential Example 10 was uniformly mixed with a surface-treating agent comprising a mixed liquid of 1.0 g of ethylene carbonate and 3.0 g of pure water, and then the resultant mixture was heat-treated at 180° C. for 30 minutes. Furthermore, the resultant particles were disintegrated to such a degree that they could pass through a JIS standard sieve having a mesh opening size of 850 μm. As a result, water-absorbent resin particles (a1) were obtained.

REFERENTIAL EXAMPLE 14

An amount of 100 g of the water-absorbent resin (b) as obtained from the aforementioned Referential Example 11 was uniformly mixed with a surface-treating agent comprising a mixed liquid of 1.0 g of 2-oxazolidone and 3.0 g of pure water, and then the resultant mixture was heat-treated at 185° C. for 30 minutes. Furthermore, the resultant particles were disintegrated to such a degree that they could pass through a JIS standard sieve having a mesh opening size of 710 μm. As a result, water-absorbent resin particles (b1) were obtained.

REFERENTIAL EXAMPLE 15

An amount of 100 g of the water-absorbent resin particles (c) as obtained from the aforementioned Referential Example 12 were uniformly mixed with a surface-treating agent comprising a mixed liquid of 1.0 g of 1,4-butanediol and 3.0 g of pure water, and then the resultant mixture was heat-treated at 190° C. for 30 minutes. Furthermore, the resultant particles were disintegrated to such a degree that they could pass through a JIS standard sieve having a mesh opening size of 600 μm. As a result, water-absorbent resin particles (c1) were obtained.

EXAMPLE 22

An amount of 100 g of the water-absorbent resin particles (c1) as obtained from the aforementioned Referential Example 15 were heated to 140° C., and then mixed with 2 g of potassium alum (potassium aluminum sulfate dodecahydrate) under stirring, and then the stirring was continued for 10 minutes, thus obtaining a water-absorbent resin composition (22).

COMPARATIVE EXAMPLE 11

An amount of 100 g of the water-absorbent resin particles (c1) as obtained from the aforementioned Referential Example 15 were mixed with an aqueous solution comprising 2 g of potassium alum (potassium aluminum sulfate dodecahydrate) and 8 g of water under stirring, thus obtaining a comparative water-absorbent resin composition (11).

COMPARATIVE EXAMPLE 12

An amount of 100 g of the water-absorbent resin particles (c1) as obtained from the aforementioned Referential Example 15 were mixed with 2 g of potassium alum (potassium aluminum sulfate dodecahydrate), and then thereto 3 g of water was added under stirring, thus obtaining a comparative water-absorbent resin composition (12).

EXAMPLE 23

An amount of 100 g of the water-absorbent resin particles (b1) as obtained from the aforementioned Referential Example 14 were mixed with 1.5 g of ammonium alum (ammonium aluminum sulfate dodecahydrate) under stirring, and then the resultant mixture was heated to 130° C., and then the stirring was continued for 15 minutes, thus obtaining a water-absorbent resin composition (23).

COMPARATIVE EXAMPLE 13

An amount of 100 g of the water-absorbent resin particles (b1) as obtained from the aforementioned Referential Example 14 were mixed with an aqueous solution comprising 1.5 g of ammonium alum (ammonium aluminum sulfate dodecahydrate) and 8.5 g of water under stirring, thus obtaining a comparative water-absorbent resin composition (13).

COMPARATIVE EXAMPLE 14

An amount of 100 g of the water-absorbent resin particles (b1) as obtained from the aforementioned Referential Example 14 were mixed with 1.5 g of ammonium alum (ammonium aluminum sulfate dodecahydrate), and then thereto 3 g of water was added under stirring, thus obtaining a comparative water-absorbent resin composition (14).

[As to Water-Absorbent Resin Compositions (22) to (23) and Comparative Water-Absorbent Resin Compositions (11) to (14) as Obtained from Examples 22 to 23 and Comparative Examples 11 to 14]:

Shown in Table 8 are the CRC, AAP, and SFC of the water-absorbent resin compositions (22) to (23) and comparative water-absorbent resin compositions (11) to (14) as obtained from Examples 22 to 23 and Comparative Examples 11 to 14.

Figure 5:
FIG. 5 is a view (FIG. 5-(a)) obtained by taking an electron photomicrograph of the water-absorbent resin composition (22) and, as to this photomicrograph, a view (FIG. 5-(b)) obtained by taking an X-ray image photomicrograph of the sulfur element by an SEM-EDS.
Figure 5:
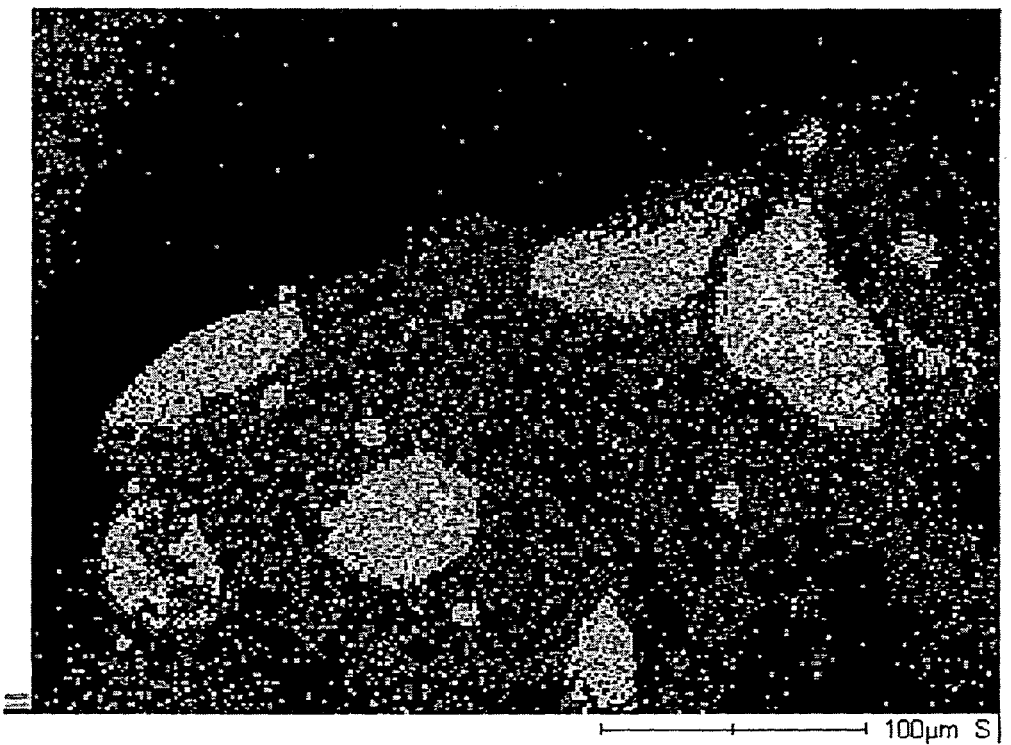
Figure 6:
FIG. 6 is a view (FIG. 6-(a)) obtained by taking an electron photomicrograph of the water-absorbent resin composition (22) and, as to this photomicrograph, a view (FIG. 6-(b)) obtained by taking an X-ray image photomicrograph of the sulfur element by an SEM-EDS.
Figure 6:
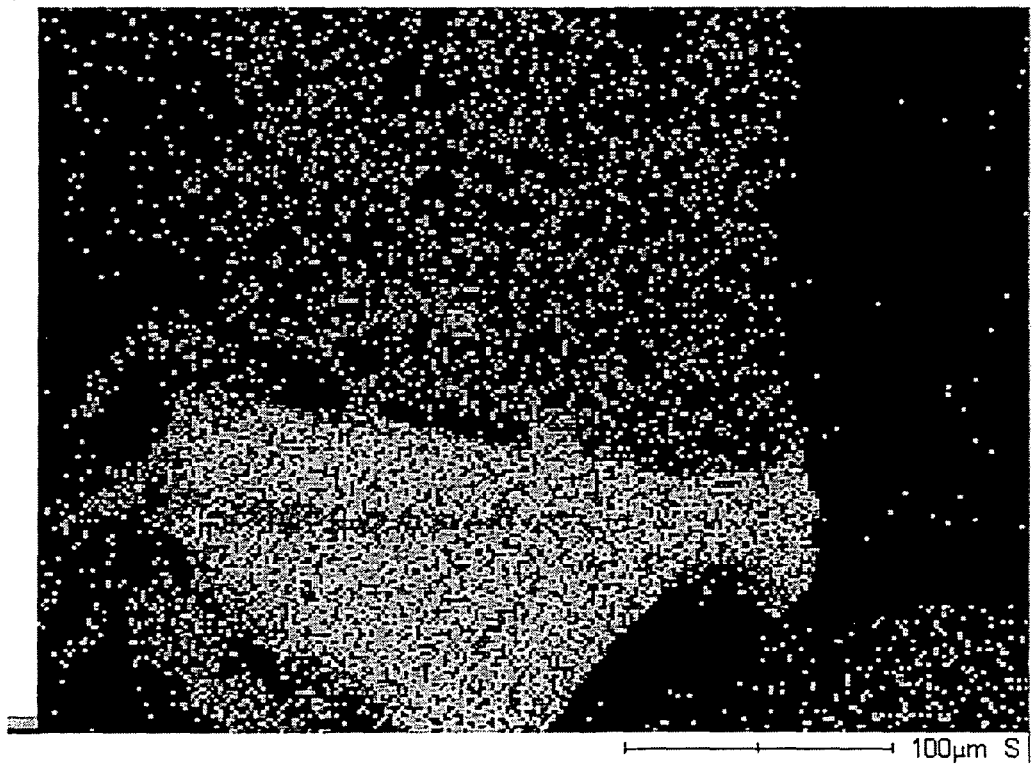

In addition, shown in FIGS. 5 and 6 are: views (FIG. 5-(a) and FIG. 6-(a)) obtained by taking electron photomicrographs of the water-absorbent resin composition (22) as obtained from Example 22; and, as to these photomicrographs, views (FIG. 5-(b) and FIG. 6-(b)) obtained by taking X-ray image photomicrographs of the sulfur element by an SEM-EDS (Energy Dispersive X-ray Spectrometer), wherein the sulfur element is originated from the sulfate ion as contained in the potassium alum. The views obtained by taking the X-ray image photomicrographs of the sulfur element are more sensitive and easier to see than X-ray images of the aluminum element, and thus have been used (the X-ray images of the aluminum element also display the same distributions as of the sulfur element).

TABLE 8

| Example No. | Water-absorbent resin particles or water-absorbent resin composition | Metal compound | Addition method | CRC (g/g) | AAP (g/g) | SFC ($\times 10^{-7} \cdot cm^3 \cdot s \cdot g^{-1}$) |
|---|---|---|---|---|---|---|
| Referential Example 15 | Water-absorbent resin particles (c1) | — | — | 26.3 | 23.7 | 73 |
| Example 22 | Water-absorbent resin composition (22) | Potassium alum | Heat-fusion | 26.4 | 23.6 | 164 |
| Comparative Example 11 | Comparative water-absorbent resin composition (11) | Potassium alum | Aqueous solution addition | 25.3 | 20.0 | 101 |
| Comparative Example 12 | Comparative water-absorbent resin composition (12) | Potassium alum | Dry mixing + addition of water | 25.8 | 22.9 | 120 |
| Referential Example 14 | Water-absorbent resin particles (b1) | — | — | 31.2 | 25.1 | 25 |
| Example 23 | Water-absorbent resin composition (23) | Ammonium alum | Heat-fusion | 31.5 | 24.7 | 56 |
| Comparative Example 13 | Comparative water-absorbent resin composition (13) | Ammonium alum | Aqueous solution addition | 30.1 | 21.1 | 32 |
| Comparative Example 14 | Comparative water-absorbent resin composition (14) | Ammonium alum | Dry mixing + addition of water | 30.5 | 24.1 | 36 |

From Table 8, it can be understood that: even in the case where the same amount of metal compound is added to the same water-absorbent resin particles, the water-absorbent resin compositions according to the present invention have excellent liquid permeability and liquid diffusibility, and also are water-absorbent resin compositions excellent in point of little deterioration of the CRC and AAP.

From FIGS. 5 and 6, there can be well seen a state where the metal compound is fused to surfaces of the water-absorbent resin particles. As is illustrated by FIG. 5, in the water-absorbent resin composition according to the present invention, favorably, at least a part of the metal compound is fused in the form of coating at least a part of surfaces of the water-absorbent resin particles in a layered state. In addition, as is illustrated by FIG. 6, there is also preferred a form such that inter-particular binding between the water-absorbent resin particles and particles of the metal compound is formed by the fusion.

EXAMPLE 24

An amount of 100 g of the water-absorbent resin particles (c1) as obtained from the aforementioned Referential Example 15 were heated to 170° C., and then mixed with 1 g of aluminum sulfate tetradeca- to octadecahydrates (mass-average particle diameter: 150 μm) under stirring for 5 minutes, thus obtaining a water-absorbent resin composition (24).

COMPARATIVE EXAMPLE 15

An amount of 100 g of the water-absorbent resin particles (c1) as obtained from the aforementioned Referential Example 15 were heated to 70° C., and then mixed with 1 g of aluminum sulfate tetradeca- to octadecahydrates (mass-average particle diameter: 150 μm) under stirring for 5 minutes, thus obtaining a comparative water-absorbent resin composition (15).

COMPARATIVE EXAMPLE 16

An amount of 100 g of the water-absorbent resin particles (c1) as obtained from the aforementioned Referential Example 15 were mixed with 1 g of aluminum sulfate tetradeca- to octadecahydrates (mass-average particle diameter: 150 μm) under stirring for 5 minutes, thus obtaining a comparative water-absorbent resin composition (16).

COMPARATIVE EXAMPLE 17

An amount of 100 g of the water-absorbent resin particles (c1) as obtained from the aforementioned Referential Example 15 were mixed with 1 g of aluminum sulfate tetradeca- to octadecahydrates (mass-average particle diameter: 150 μm), and then thereto 3 g of water was added under stirring, thus obtaining a comparative water-absorbent resin composition (17).

COMPARATIVE EXAMPLE 18

An amount of 100 g of the water-absorbent resin particles (c1) as obtained from the aforementioned Referential Example 15 were mixed with an aqueous solution comprising 1 g of aluminum sulfate tetradeca- to octadecahydrates (mass-average particle diameter: 150 μm) and 4 g of water under stirring, thus obtaining a comparative water-absorbent resin composition (18).

[As to Water-Absorbent Resin Composition (24) and Comparative Water-Absorbent Resin Compositions (15) to (18) as Obtained from Example 24 and Comparative Examples 15 to 18]:

Shown in Table 9 are the results of having measured the content of the aluminum sulfate tetradeca- to octadecahydrates (hereinafter abbreviated to ASH) every particle diameter range in the water-absorbent resin compositions (22) and (24) and comparative water-absorbent resin compositions (15) to (18) as obtained from Examples 22 and 24 and Comparative Examples 15 to 18. Incidentally, the results were calculated from the aluminum contents as measured by the aforementioned plasma emission spectrometry.

TABLE 9

| Example No. | Water-absorbent resin particles or water-absorbent resin composition | Addition method | AL ppm | AL (<300 μm) ppm | Metal compound segregation index |
|---|---|---|---|---|---|
| Referential Example 15 | Water-absorbent resin particles (c1) | — | — | — | — |
| Example 22 | Water-absorbent resin composition (22) | Heat-fusion | 114 | 104 | 0.91 |
| Example 24 | Water-absorbent resin composition (24) | Heat-fusion | 91 | 137 | 1.51 |
| Comparative Example 15 | Comparative water-absorbent resin composition (15) | Heating to lower than melting point | 90 | 218 | 2.42 |
| Comparative Example 16 | Comparative water-absorbent resin composition (16) | Dry mixing | 91 | 228 | 2.51 |
| Comparative Example 17 | Comparative water-absorbent resin composition (17) | Dry mixing + addition of water | 92 | 204 | 2.22 |
| Comparative Example 18 | Comparative water-absorbent resin composition (18) | Aqueous solution addition | 90 | 143 | 1.59 |

AL: aluminum content (ppm) of the water-absorbent resin composition or comparative water-absorbent resin composition AL (<300 μm): aluminum content (ppm) of particles passing through a mesh having a mesh opening size of 300 μm in the water-absorbent resin composition or comparative water-absorbent resin composition As can be understood from Table 9, because the ASH which is contained in the water-absorbent resin composition (24) as obtained from Example 24 is fused and entirely fixed to surfaces of water-absorbent resin particles, the ASH content of the particles passing through the mesh having a mesh opening size of 300 μm is low and almost the same as that in the case where the ASH is added in the form of an aqueous solution (comparative water-absorbent resin composition (18)). In comparison, in the cases of other methods such as dry mixing (comparative water-absorbent resin compositions (15) to (17)), because the ASH having fine particle diameters is not sufficiently fixed, the ASH content of the particles passing through the mesh having a mesh opening size of 300 μm is unfavorably high. From these results, it can be understood that the water-absorbent resin compositions according to the present invention are water-absorbent resin compositions excellent in that the segregation of the contained metal compound occurs very little. In addition, the process in which the aqueous solution of the metal compound is added may be effective for the prevention of the segregation of the metal compound similarly to the process according to the present invention, but, as shown in Table 8, has demerits in that the SFC-enhancing effect is low and in that the deterioration of the AAP is large.

under stirring, thus obtaining a comparative water-absorbent resin composition (19).

Comparative Example 20

An amount of 100 g of the water-absorbent resin particles (a1) as obtained from the aforementioned Referential Example 13 were mixed with 0.8 g of aluminum nitrate nonahydrate, and then thereto an aqueous solution comprising 3 g of water and 1 g of polyethylene glycol (average molecular weight: 300) was added under stirring, thus obtaining a comparative water-absorbent resin composition (20).

[As to Water-Absorbent Resin Composition (25) and Comparative Water-Absorbent Resin Compositions (19) to (20) as Obtained from Example 25 and Comparative Examples 19 to 20]:

Shown in Table 10 are the results of having measured the CRC, AAP, and BR of the water-absorbent resin composition (25) and comparative water-absorbent resin compositions (19) to (20) as obtained from Example 25 and Comparative Examples 19 to 20.

TABLE 10

| Example No. | Water-absorbent resin particles or water-absorbent resin composition | Metal compound | Addition method | CRC (g/g) | AAP (g/g) | BR % |
|---|---|---|---|---|---|---|
| Referential Example 13 | Water-absorbent resin particles (a1) | — | — | 36.1 | 25.9 | 35.5 |
| Example 25 | Water-absorbent resin composition (25) | ANH | Heat-fusion | 36.3 | 25.5 | 13.2 |
| Comparative Example 19 | Comparative water-absorbent resin composition (19) | ANH | Aqueous solution addition | 35.2 | 22.0 | 33.1 |
| Comparative Example 20 | Comparative water-absorbent resin composition (20) | ANH | Dry mixing + addition of water | 35.6 | 24.1 | 21.7 |

ANH: aluminum nitrate nonahydrate

EXAMPLE 25

An amount of 100 g of the water-absorbent resin particles (a1) as obtained from the aforementioned Referential Example 13 were mixed with 0.8 g of aluminum nitrate nonahydrate under stirring, and then the resultant mixture was heated to 110° C., and then the stirring was continued for 10 minutes, thus obtaining a water-absorbent resin composition (25).

COMPARATIVE EXAMPLE 19

An amount of 100 g of the water-absorbent resin particles (a1) as obtained from the aforementioned Referential Example 13 were mixed with an aqueous solution comprising 0.8 g of aluminum nitrate nonahydrate and 7.2 g of water From Table 10, it can be understood that: even in the case where the same amount of metal compound is added to the same water-absorbent resin particles, the water-absorbent resin composition according to the present invention is a water-absorbent resin composition which undergoes little deterioration of the CRC and AAP and is excellent in the BR.

EXAMPLE 26

An amount of 100 g of the water-absorbent resin particles (b1) as obtained from the aforementioned Referential Example 14 were heated to 120° C., and then mixed with 1 g of aluminum chloride hexahydrate under stirring for 5 minutes, thus obtaining a water-absorbent resin composition (26).

EXAMPLE 27

An amount of 100 g of the water-absorbent resin particles (c1) as obtained from the aforementioned Referential Example 15 were heated to 100° C., and then mixed with 2 g of sodium aluminum sulfate dodecahydrate under stirring for 5 minutes, thus obtaining a water-absorbent resin composition (27).

COMPARATIVE EXAMPLE 21

An amount of 100 g of the water-absorbent resin particles (b1) as obtained from the aforementioned Referential Example 14 were heated to 120° C., and then mixed with 1 g of paraffin wax (melting point: 83° C.) under stirring for 5 minutes, thus obtaining a comparative water-absorbent resin composition (21).

COMPARATIVE EXAMPLE 22

An amount of 100 g of the water-absorbent resin particles (c1) as obtained from the aforementioned Referential Example 15 were heated to 160° C., and then mixed with 1 g of zinc caprylate under stirring for 5 minutes, thus obtaining a comparative water-absorbent resin composition (22).

COMPARATIVE EXAMPLE 23

An amount of 100 g of the water-absorbent resin particles (c1) as obtained from the aforementioned Referential Example 15 were uniformly mixed with 5 g of TRICLOSAN, and then the resultant mixture was heated to 80° C., and then the mixing was continued under stirring for 1 hour, thus obtaining a comparative water-absorbent resin composition (23).

[As to Water-Absorbent Resin Compositions (26) to (27) and Comparative Water-Absorbent Resin Compositions (21) to (23) as Obtained from Examples 26 to 27 and Comparative Examples 21 to 23]:

Shown in Table 11 are the CRC, SFC, and CSF of the water-absorbent resin compositions (26) to (27) and comparative water-absorbent resin compositions (21) to (23) as obtained from Examples 26 to 27 and Comparative Examples 21 to 23.

TABLE 11

| Example No. | Particulate water-absorbent resin or water-absorbent resin composition | Metal compound | Addition method | CRC (g/g) | SFC ($\times 10^{-7} \cdot cm^3 \cdot s \cdot g^{-1}$) | CSF (g/g) |
|---|---|---|---|---|---|---|
| Referential Example 14 | Water-absorbent resin particles (b1) | — | — | 31.2 | 25 | 24.1 |
| Example 23 | Water-absorbent resin composition (23) | Ammonium alum | Heat-fusion | 31.5 | 56 | 23.6 |
| Example 26 | Water-absorbent resin composition (26) | ACH | Heat-fusion | 31.2 | 51 | 23.5 |
| Comparative Example 21 | Comparative water-absorbent resin composition (21) | Paraffin wax | Heat-fusion | 31.0 | 24 | 12.1 |
| Referential Example 15 | Water-absorbent resin particles (c1) | — | — | 26.3 | 73 | 25.1 |
| Example 22 | Water-absorbent resin composition (22) | Potassium alum | Heat-fusion | 26.4 | 164 | 22.4 |
| Example 27 | Water-absorbent resin composition (27) | ASSH | Heat-fusion | 26.3 | 157 | 22.1 |
| Comparative Example 22 | Comparative water-absorbent resin composition (22) | Zinc caprylate | Heat-fusion | 26.2 | 81 | 9.8 |
| Comparative Example 23 | Comparative water-absorbent resin composition (23) | TRICLOSAN | Heat-fusion | 26.1 | 71 | 13.1 |

ACH: aluminum chloride hexahydrate
ASSH: sodium aluminum sulfate dodecahydrate
Zinc caprylate: $(CH_3(CH_2)_6COO)_2Zn$
TRICLOSAN: 2',4',4-trichloro-2-hydroxydiphenyl ether From Table 11, it can be understood that the water-absorbent resin compositions according to the present invention have excellent SFC and CSF and are excellent in the liquid permeability and liquid diffusibility and in the capillary suction force. As to such as heat-fusible resins like the comparative water-absorbent resin composition (21), the effects of the present invention are not obtained, and, on the contrary, such as deterioration of the CSF is brought about. In the case where the polyvalent metal salt of the organic acid having not fewer than 7 carbon atoms per molecule is used like the case of the comparative water-absorbent resin composition (22), great deterioration of the CSF is caused. Also in the case of using the organic substance like the case of the comparative water-absorbent resin composition (23), the effects of the present invention are not obtained, and, on the contrary, such as deterioration of the CSF is brought about.

COMPARATIVE EXAMPLE 24

An amount of 100 g of the water-absorbent resin particles (c1) as obtained from the aforementioned Referential Example 15 were mixed with 2 g of potassium alum (potassium aluminum sulfate dodecahydrate) under stirring, and then the stirring was continued for 10 minutes, thus obtaining a comparative water-absorbent resin composition (24).

[As to Comparative Water-Absorbent Resin Composition (24) as Obtained from Comparative Example 24]:

Shown in Table 12 are the BR of the water-absorbent resin composition (22) and comparative water-absorbent resin compositions (11), (12) and (24) as obtained from Example 22 and Comparative Examples 11, 12 and 24.

TABLE 12

| Example No. | Water-absorbent resin particles or water-absorbent resin composition | Metal compound | Addition method | BR % |
|---|---|---|---|---|
| Referential Example 15 | Water-absorbent resin particles (c1) | — | — | 28.9 |
| Example 22 | Water-absorbent resin composition (22) | Potassium alum | Heat-fusion | 4.7 |
| Comparative Example 11 | Comparative water-absorbent resin composition (11) | Potassium alum | Aqueous solution addition | 25.1 |
| Comparative Example 12 | Comparative water-absorbent resin composition (12) | Potassium alum | Dry mixing + addition of water | 15.6 |
| Comparative Example 24 | Comparative water-absorbent resin composition (24) | Potassium alum | Dry mixing | 10.3 |

From Table 12, it can be understood that the water-absorbent resin composition according to the present invention has a more excellent BR and is more excellent in the handling property during the moisture absorption when compared with other addition methods.

Shown in Table 13 are the particle diameter distributions of the water-absorbent resin particles (a1), (b1) and (c1) as obtained from Referential Examples 13 to 15 and the water-absorbent resin compositions (22) to (27) as obtained from Examples 22 to 27.

TABLE 13

| | Referential Example No. and Example No. | | | | | | | | |
|---|---|---|---|---|---|---|---|---|---|
| | Referential Example 13 | Referential Example 14 | Referential Example 15 | Example 22 | Example 23 | Example 24 | Example 25 | Example 26 | Example 27 |
| Water-absorbent resin particles | (a1) | (b1) | (c1) | — | — | — | — | — | — |
| Water-absorbent resin composition | — | — | — | (22) | (23) | (24) | (25) | (26) | (27) |
| ≧850 μm (mass %) | 0.0 | 0.0 | 0.0 | 0.0 | 0.0 | 0.0 | 0.0 | 0.0 | 0.0 |
| 850-710 μm (mass %) | 2.9 | 0.0 | 0.0 | 0.0 | 0.1 | 0.0 | 3.1 | 0.1 | 0.0 |
| 710-600 μm (mass %) | 28.0 | 6.5 | 0.0 | 0.1 | 6.8 | 0.1 | 28.4 | 6.6 | 0.0 |
| 600-500 μm (mass %) | 17.1 | 8.9 | 3.1 | 3.4 | 9.3 | 3.3 | 17.5 | 9.2 | 3.3 |
| 500-425 μm (mass %) | 13.7 | 18.3 | 17.1 | 18.4 | 19.2 | 17.6 | 14.1 | 18.7 | 17.5 |
| 425-300 μm (mass %) | 20.7 | 37.3 | 35.4 | 35.8 | 37.1 | 34.4 | 21.5 | 37.4 | 35.3 |
| 300-212 μm (mass %) | 10.9 | 16.8 | 27.4 | 26.3 | 16.5 | 27.2 | 9.8 | 16.6 | 27.8 |
| 212-150 μm (mass %) | 4.2 | 7.3 | 13.1 | 12.5 | 6.9 | 13.2 | 3.5 | 7.1 | 12.9 |
| 150-45 μm (mass %) | 2.3 | 4.8 | 3.8 | 3.5 | 4.1 | 4.1 | 2.1 | 4.3 | 3.2 |
| ≦45 μm (mass %) | 0.2 | 0.1 | 0.1 | 0.0 | 0.0 | 0.1 | 0.0 | 0.0 | 0.0 |
| Total (mass %) | 100.0 | 100.0 | 100.0 | 100.0 | 100.0 | 100.0 | 100.0 | 100.0 | 100.0 |

TABLE 13-continued

| | Referential Example No. and Example No. | | | | | | | |
|---|---|---|---|---|---|---|---|---|
| | Referential Example 13 | Referential Example 14 | Referential Example 15 | Example 22 | Example 23 | Example 24 | Example 25 | Example 26 | Example 27 |
| D50 (μm) | 488 | 366 | 315 | 322 | 372 | 315 | 494 | 369 | 317 |
| σζ | 0.40 | 0.38 | 0.37 | 0.37 | 0.37 | 0.38 | 0.37 | 0.37 | 0.36 |

(≧A μm) represents water-absorbent resin particles or a water-absorbent resin composition remaining on a sieve of A in mesh opening size as a result of the classification operation.
(≦B μm) represents water-absorbent resin particles or a water-absorbent resin composition having passed through a sieve of B in mesh opening size as a result of the classification operation.
(A-B μm) represents water-absorbent resin particles or a water-absorbent resin composition having passed through the sieve of A in mesh opening size and remaining on the sieve of B in mesh opening size as a result of the classification operation.

INDUSTRIAL APPLICATION

Because the water-absorbent resin compositions (1) and (2) according to the present invention have excellent water absorption properties, these water-absorbent resin compositions can be used as water-absorbing and water-retaining agents for various purposes. For example, these water-absorbent resin compositions can be used for such as: water-absorbing and water-retaining agents for absorbent articles (e.g. disposable diapers, sanitary napkins, incontinent pads, and medical pads); agricultural and horticultural water-retaining agents (e.g. substitutes for peat moss, soil-modifying-and-improving agents, water-retaining agents, and agents for duration of effects of agricultural chemicals); water-retaining agents for buildings (e.g. dew-condensation-preventing agents for interior wall materials, cement additives); release control agents; coldness-retaining agents; disposable portable body warmers; sludge-solidifying agents; freshness-retaining agents for foods; ion-exchange column materials; dehydrating agents for sludge or oil; desiccating agents; and humidity-adjusting materials. In addition, the water-absorbent resin compositions (1) and (2) according to the present invention can be used particularly favorably for sanitary materials for absorption of excrement, urine, or blood, such as disposable diapers and sanitary napkins.

The invention claimed is:

1. A water-absorbent resin composition, which is a water-absorbent resin composition comprising water-absorbent resin particles obtained by polymerizing a monomer including acrylic acid and/or its salt,
with the composition having a mass-average particle diameter of 100 to 600 μm and comprising water-soluble polyvalent metal salt particles and the water-absorbent resin particles that have been surface-crosslinked, and where at least a part of the water-absorbent resin particles are agglomerates, and at least a part of the water-soluble polyvalent metal salt particles are fused to surfaces of the water-absorbent resin particles.

2. A water-absorbent resin composition according to claim 1, wherein the water-soluble polyvalent metal salt particles are particles of an aluminum salt having water of crystallization.

3. A water-absorbent resin composition according to claim 1, wherein the water-absorbent resin particles are those which have been surface-crosslinked with a polyhydric alcohol.

4. A water-absorbent resin composition, which is a water-absorbent resin composition having a mass-average particle diameter of 100 to 600 μM comprising water-absorbent resin particles and water-soluble polyvalent metal salt particles, wherein the water-absorbent resin particles are obtained by polymerizing a monomer including acrylic acid and/or its salt, with the composition having a saline flow conductivity of at least 50 ($\times 10^{-7} \cdot cm^3 \cdot s \cdot g^{-1}$) and a retention ratio of the saline flow conductivity of not less than 40%, and where at least a part of the water-absorbent resin particles are agglomerates, and at least a part of the water-soluble polyvalent metal salt particles are fused to surfaces of the water-absorbent resin particles.

5. A water-absorbent resin composition according to claim 4, wherein the retention ratio of the saline flow conductivity after a paint shaker test is not less than 70%.

6. A process for production of a water-absorbent resin composition, which is characterized by comprising the steps of:
adding a binder to water-absorbent resin particles obtained by polymerizing a monomer including acrylic acid and/or its salt; and then
mixing the binder and the water-absorbent resin particles with water-soluble polyvalent metal salt particles to produce the water-absorbent resin composition having a mass-average particle diameter of 100 to 600 μm, and where at least a part of the water-absorbent resin particles are agglomerates, and at least a part of the water-soluble polyvalent metal salt particles are fused to surfaces of the water-absorbent resin particles.

7. A process for production of a water-absorbent resin composition according to claim 6, wherein the water-absorbent resin particles are surface-crosslinked ones.

8. A process for production of a water-absorbent resin composition according to claim 6, wherein the binder contains a surface-crosslinking agent.

9. A process for production of a water-absorbent resin composition according to claim 6, wherein the binder includes water and/or a polyhydric alcohol.

10. A process for production of a water-absorbent resin composition according to claim 6, wherein, when the binder is added to the water-absorbent resin particles, the temperature of the water-absorbent resin particles is in the range of 40 to 100° C.

11. A water-absorbent resin composition according to claim 5, wherein the water-absorbent resin particles have a mass-average particle diameter of not larger than 500 μm; and the water-soluble polyvalent metal salt has a mass-average particle diameter of not larger than 500 μm.

12. A water-absorbent resin composition according to claim 1, 4 or 5, wherein the water-absorbent resin particles have been surface-crosslinked with an organic surface-crosslinking agent.

13. A water-absorbent resin composition according to claim 12, wherein the organic surface-crosslinking agent is a polyhydric alcohol.

14. A process for production of a water-absorbent resin composition according to claim 6, 7 or 8, wherein the water-absorbent resin particles have a mass-average particle diameter of not larger than 500 μm; and the water-soluble polyvalent metal salt particles have a mass-average particle diameter of not larger than 500 μm.

15. A water-absorbent resin composition according to claim 4, wherein the composition is prepared by dry mixing the water-soluble polyvalent metal salt and the water-absorbent resin particles.

16. A water-absorbent resin composition according to claim 1 or claim 4, wherein the water-soluble polyvalent metal salt particles are a powder having a mass-average particle diameter of not larger than 1,000 μm.

17. A water-absorbent resin composition according to claim 1, wherein the fusion is heat-fusion.

18. A water-absorbent resin composition according to claim 4, which has a saline flow conductivity of not less than $100 \times 10^{-7} \cdot cm^3 \cdot s/g$.

19. The process for production of a water-absorbent resin composition according to claim 6, wherein the water-soluble polyvalent metal salt particles comprise one or more members selected from the group consisting of alkaline metal salts and polyvalent metal salts (except polyvalent metal salts of organic acids having not fewer than 7 carbon atoms per molecule); with the process comprising the steps of:

heating the water-absorbent resin particles and/or the water-soluble polyvalent metal salt particles to a temperature of not lower than the melting point of the water-soluble polyvalent metal salt particles; and thereby fusing at least a part of the water-soluble polyvalent metal salt particles to surfaces of the water-absorbent resin particles.

20. The water-absorbent resin composition of claim 1, wherein the amount of the agglomerates is not smaller than 5 mass %.

21. The water-absorbent resin composition of claim 4, wherein the amount of the agglomerates is not smaller than 5 mass %.

22. The process for the production of a water-absorbent composition of claim 6, wherein the amount of the agglomerates is not smaller than 5 mass %.

23. The water-absorbent resin composition of claim 4, wherein the fusion is heat-fusion.

24. The process of claim 6, wherein the fusion is heat-fusion.

* * * * *